United States Patent
Nelson et al.

(10) Patent No.: US 8,522,790 B2
(45) Date of Patent: *Sep. 3, 2013

(54) STABILIZED MAGNETIC FORCE DEVICES, SYSTEMS AND METHODS

(75) Inventors: Lionel M. Nelson, Los Altos, CA (US); Octavian Iancea, Sunnyvale, CA (US); Brian K. McCollum, Redwood City, CA (US); Andres D. Tomas, Union City, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1581 days.

This patent is subject to a terminal disclaimer.

(21) Appl. No.: 11/592,529

(22) Filed: Nov. 3, 2006

(65) Prior Publication Data

US 2007/0144533 A1   Jun. 28, 2007

Related U.S. Application Data

(63) Continuation-in-part of application No. 10/718,254, filed on Nov. 20, 2003, now Pat. No. 7,360,542, which is a continuation-in-part of application No. 10/656,861, filed on Sep. 6, 2003, now Pat. No. 7,188,627, and a continuation-in-part of application No. 10/236,455, filed on Sep. 6, 2002, now Pat. No. 7,216,648.

(60) Provisional application No. 60/441,639, filed on Jan. 22, 2003, provisional application No. 60/456,164, filed on Mar. 20, 2003.

(51) Int. Cl.
*A61F 5/56* (2006.01)

(52) U.S. Cl.
USPC .......................................... 128/848; 602/902

(58) Field of Classification Search
USPC ................... 128/848, 846; 600/12; 602/902; 433/6

See application file for complete search history.

(56) References Cited

U.S. PATENT DOCUMENTS

| | | | |
|---|---|---|---|
| 4,304,227 A | 12/1981 | Samelson |
| 4,978,323 A | 12/1990 | Freedman |
| 5,019,372 A | 5/1991 | Folkman et al. |
| 5,176,618 A | 1/1993 | Freedman |
| 5,220,918 A | 6/1993 | Heide et al. |
| 5,373,859 A | 12/1994 | Forney |
| 5,465,734 A | 11/1995 | Alvarez et al. |
| 5,649,540 A | 7/1997 | Alvarez et al. |
| 5,792,067 A | 8/1998 | Karell |
| RE36,120 E | 3/1999 | Karell |
| 5,979,456 A | 11/1999 | Magovern |
| 5,988,171 A | 11/1999 | Sohn et al. |
| 6,231,496 B1 | 5/2001 | Wilk et al. |
| 6,244,865 B1 | 6/2001 | Nelson et al. |
| 6,250,307 B1 | 6/2001 | Conrad et al. |
| 6,390,096 B1 | 5/2002 | Conrad et al. |
| 6,401,717 B1 | 6/2002 | Conrad et al. |
| 6,408,851 B1 | 6/2002 | Karell |

(Continued)

*Primary Examiner* — Michael A. Brown

(57) ABSTRACT

Devices, systems, and methods employ at least one ferromagnetic structure sized and configured for placement in a tissue region. A component is attached to the structure to stabilize its placement in the tissue region. An anchoring structure holds the component in a state of tension. The anchoring structure can, e.g., take the from of an anchoring body that expands in situ. The anchoring structure can be adjustable for adjusting the state of tension. The component can be elastic, to deflect under load in a prescribed manner and to recover an initial shape when unloaded.

8 Claims, 39 Drawing Sheets

(56) References Cited

U.S. PATENT DOCUMENTS

| | | |
|---|---|---|
| 6,415,796 B1 | 7/2002 | Conrad et al. |
| 6,450,169 B1 | 9/2002 | Conrad et al. |
| 6,490,885 B1 | 12/2002 | Wilkinson |
| 6,523,541 B2 | 2/2003 | Knudson et al. |
| 6,523,542 B2 | 2/2003 | Knudson et al. |
| 6,636,767 B1 | 10/2003 | Knudson et al. |
| 6,742,524 B2 | 6/2004 | Knudson et al. |
| 6,955,172 B2 | 10/2005 | Nelson et al. |
| 7,073,505 B2 | 7/2006 | Nelson et al. |
| 7,077,143 B2 | 7/2006 | Knudson et al. |
| 7,077,144 B2 | 7/2006 | Knudson et al. |
| 7,188,627 B2 | 3/2007 | Nelson et al. |
| 2001/0047805 A1 | 12/2001 | Scarberry et al. |
| 2002/0066702 A1 | 6/2002 | Liu |
| 2004/0112390 A1 | 6/2004 | Brooks et al. |
| 2005/0092332 A1 | 5/2005 | Conrad et al. |
| 2005/0092334 A1 | 5/2005 | Conrad et al. |
| 2006/0266369 A1 * | 11/2006 | Atkinson et al. ............... 128/848 |

* cited by examiner

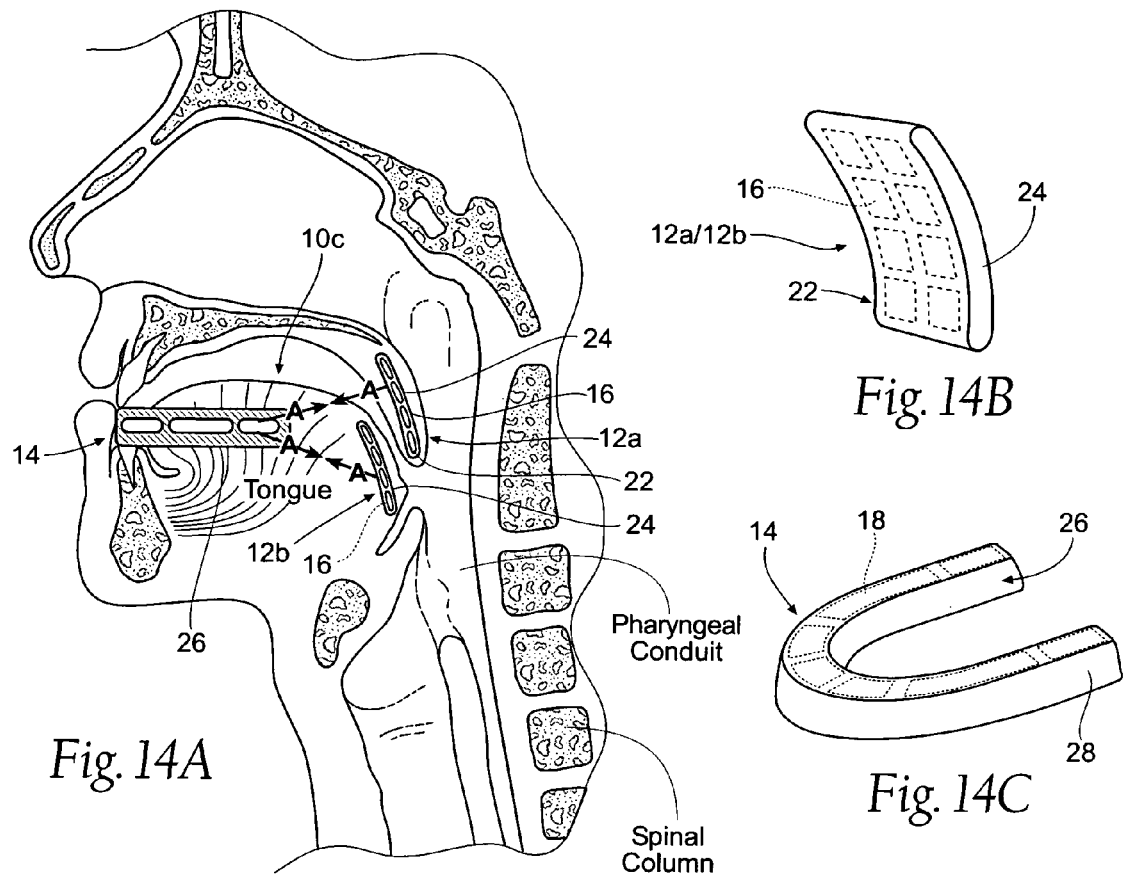
Fig. 14A
Fig. 14B
Fig. 14C
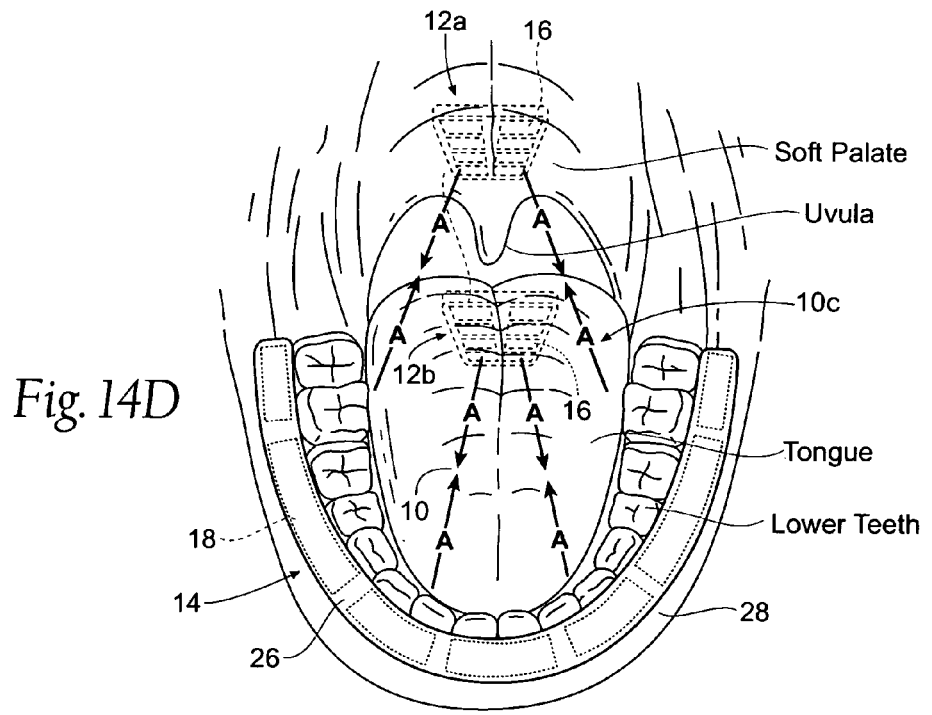
Fig. 14D

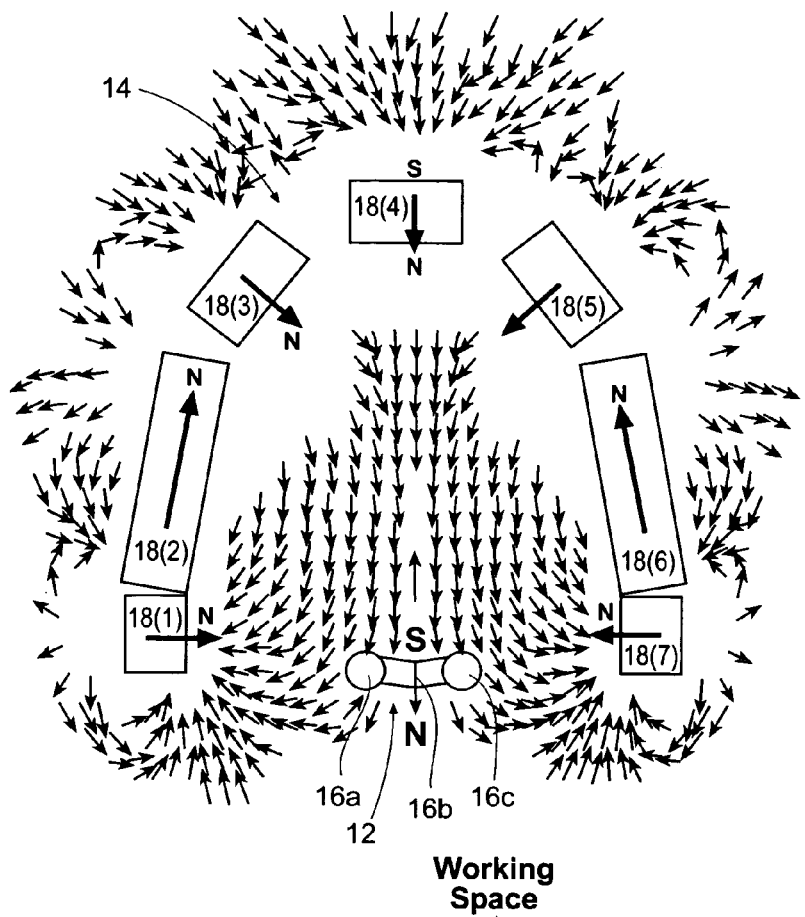
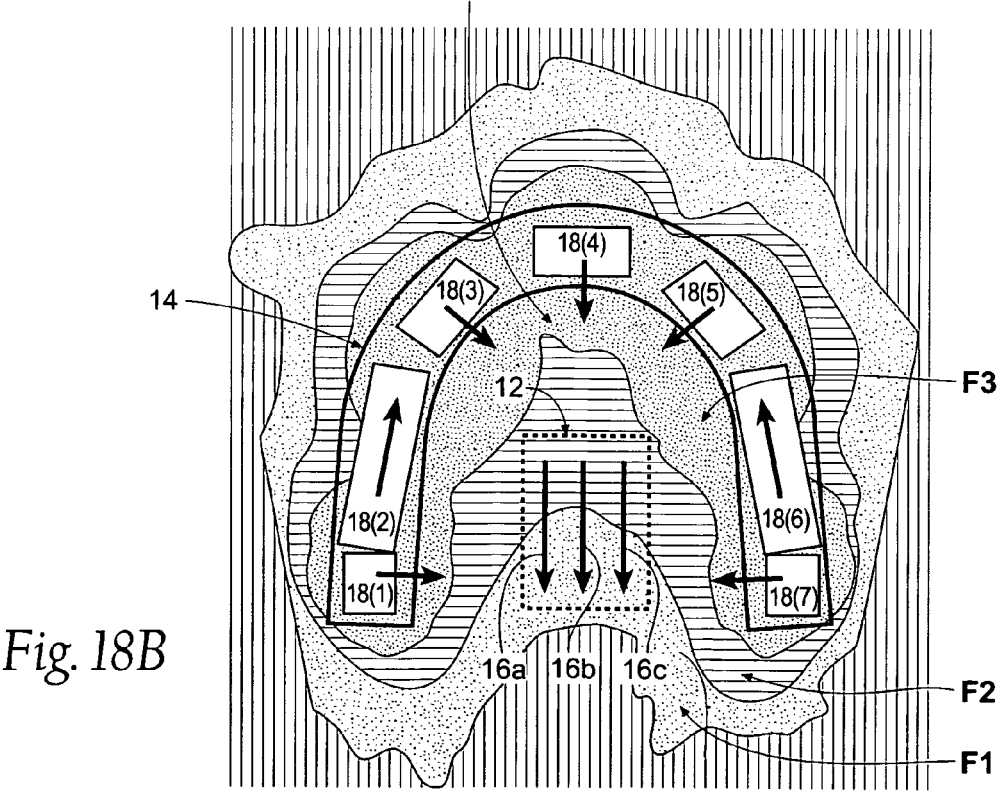
Fig. 18A
Fig. 18B

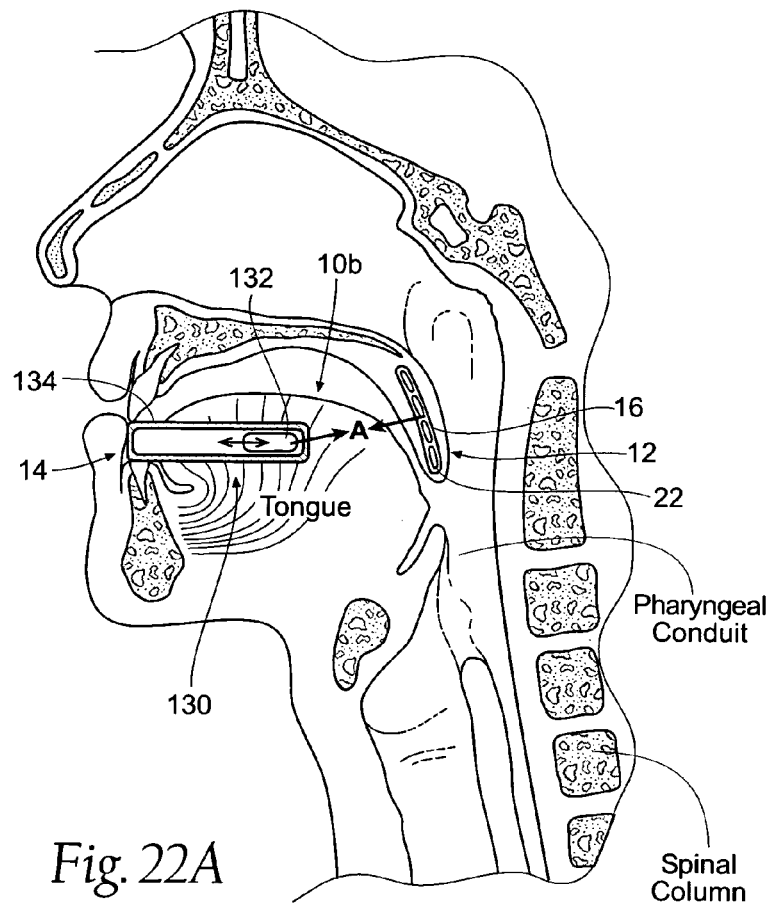
Fig. 22A
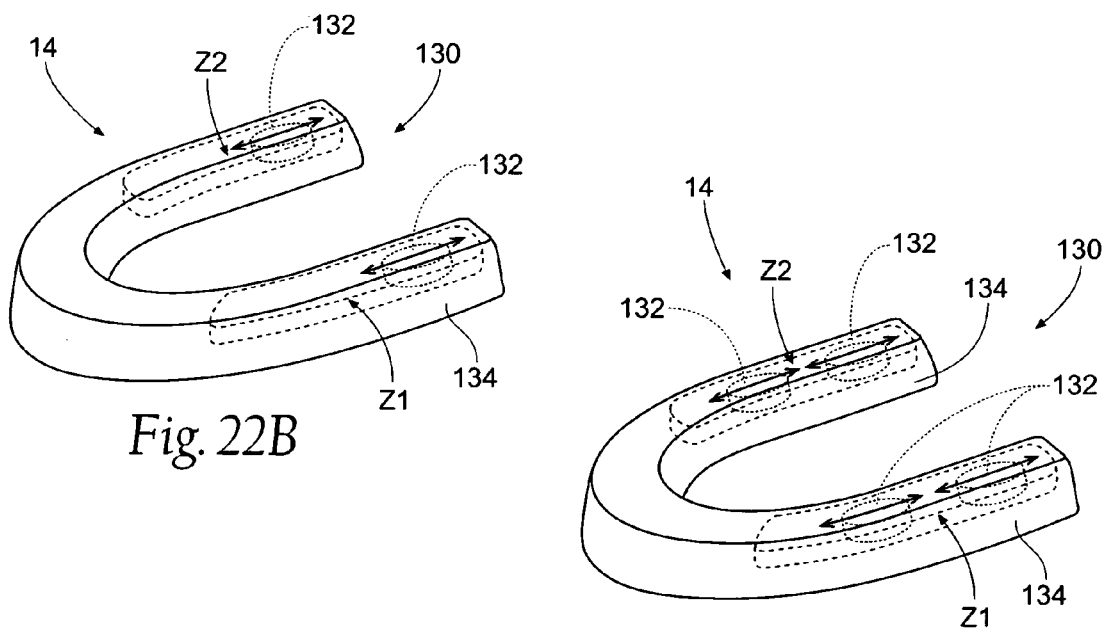
Fig. 22B
Fig. 22C

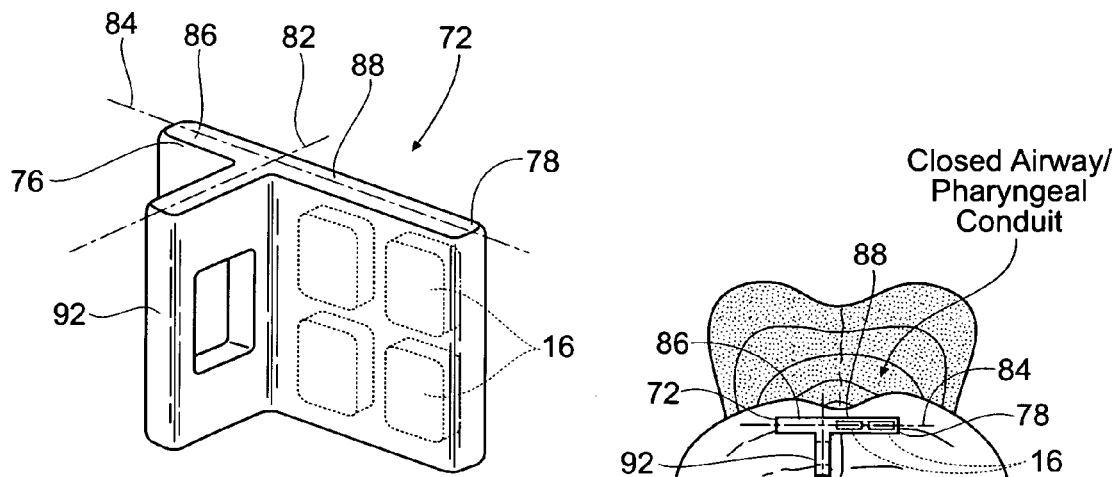
Fig. 31A
Fig. 31C
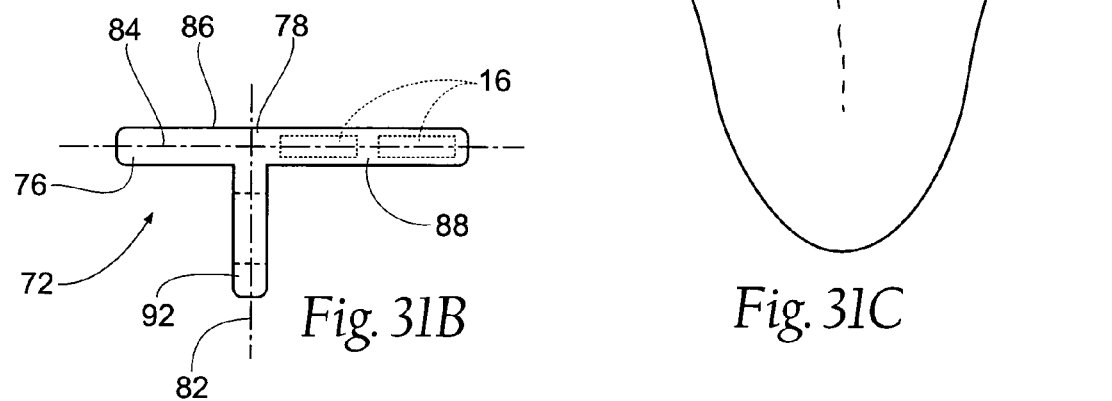
Fig. 31B
Fig. 31D

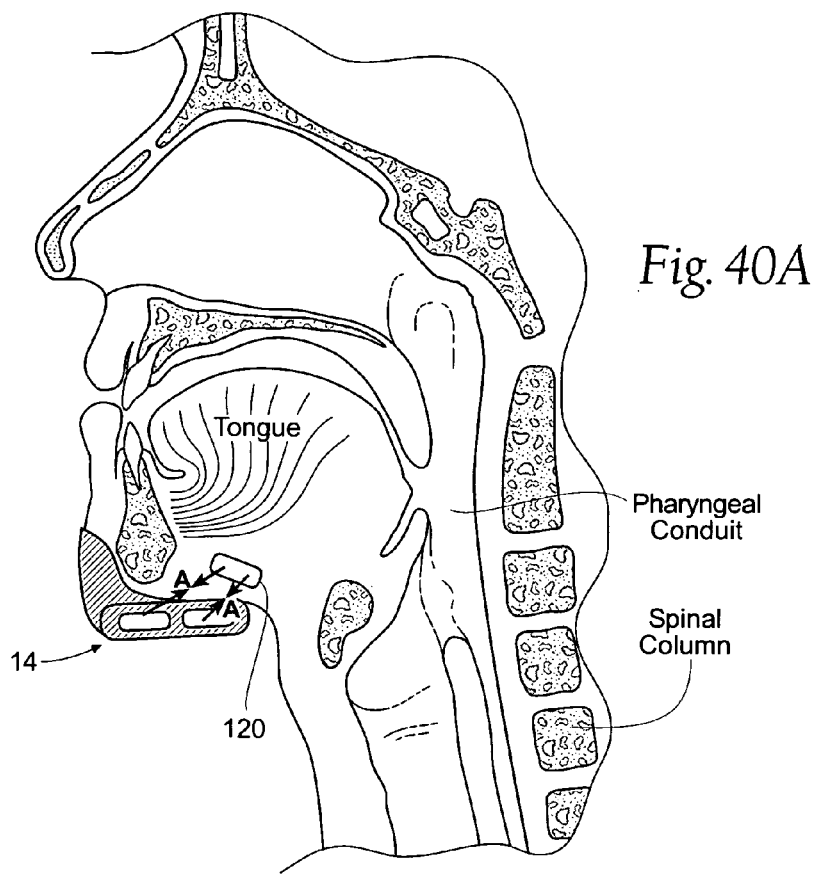
Fig. 40A
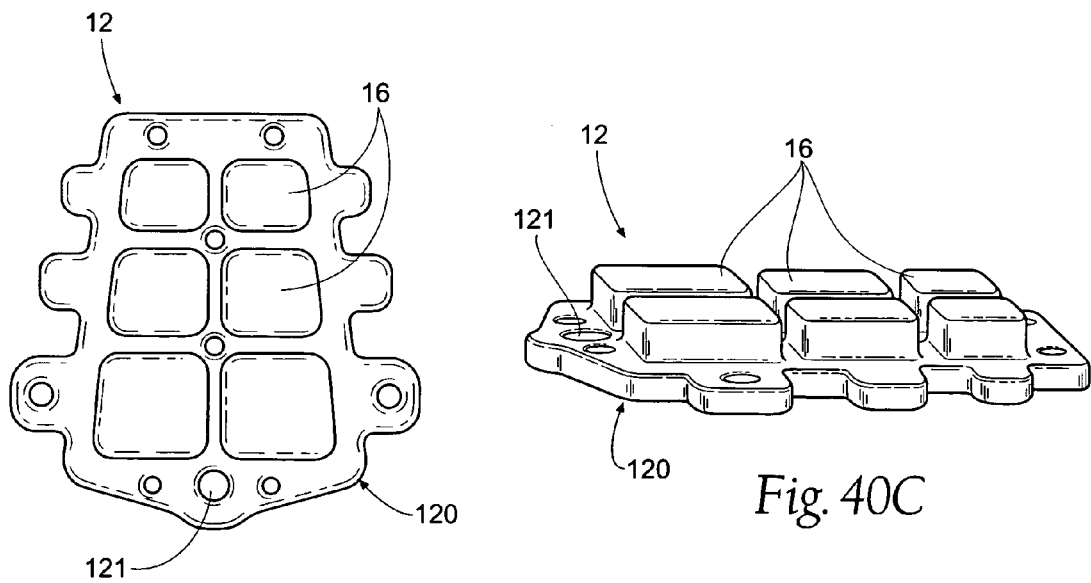
Fig. 40B
Fig. 40C

STABILIZED MAGNETIC FORCE DEVICES, SYSTEMS AND METHODS

RELATED APPLICATIONS

This application is a continuation-in-part of U.S. patent application Ser. No. 10/718,254, filed Nov. 20, 2003 entitled "Devices, Systems, and Methods to Fixate Tissue Within the Regions of the Body, Such as the Pharyngeal Conduit" (now U.S. Pat. No. 7,360,542), which is a continuation-in-part of U.S. patent application Ser. No. 10/656,861, filed Sep. 6, 2003 entitled "Magnetic Force Devices, Systems, and Methods for Resisting Tissue Collapse within the Pharyngeal Conduit" now U.S. Pat. No. 7,188,627), which further claims the benefit of U.S. Provisional Patent Application Ser. No. 60/441,639, filed Jan. 22, 2003 and U.S. Provisional Patent Application Ser. No. 60/456,164, filed Mar. 20, 2003, and which is a continuation-in-part of U.S. patent application Ser. No. 10/236,455, filed Sep. 6, 2002 and entitled "System and Method for Moving and/or Restraining Tissue in the Upper Respiratory System" (now U.S. Pat. No. 7,216,648).

FIELD OF THE INVENTION

The invention is directed to devices, systems, and methods for the treatment of sleep disordered breathing including obstructive sleep apnea and snoring.

BACKGROUND OF THE INVENTION

I. Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans.

There are two types of sleep apnea: central and obstructive. Central sleep apnea, which is relatively rare, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. Normally, the muscles of the upper part of the throat keep the airway open to permit air flow into the lungs. When the muscles of the soft palate, the base of the tongue, and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored, or even stopping it altogether. In a given night, the number of involuntary breathing pauses or "apneic events" may be as high as 20 to 30 or more per hour. These breathing pauses are almost always accompanied by snoring between apnea episodes, although not everyone who snores has the condition. Sleep apnea can also be characterized by choking sensations.

Lack of air intake into the lungs results in lower levels of oxygen and increased levels of carbon dioxide in the blood. Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Although some apneic events are normal in all persons and mammals, the frequency of blockages will determine the seriousness of the disease and potential for health damage. When the incidence of blockage is frequent, corrective action should be taken.

II. The Anatomy of the Upper Airway

As FIG. 1 shows, the upper airway consists of a conduit that begins at the nasal valve, situated in the tip of the nose, and extends to the larynx, which is also called the voice box because it houses the vocal cords. The pharynx (which, in Greek, means "throat") is a cone-shaped passageway in the upper airway that leads from the oral and nasal cavities in the head to the esophagus and larynx. The pharynx serves both respiratory and digestive functions. Both circular and longitudinal muscles are present in the walls of this organ, which are called the pharyngeal walls. The circular muscles form constrictions that help push food to the esophagus and prevent air from being swallowed, while the longitudinal muscles lift the walls of the pharynx during swallowing.

The pharynx consists of three main divisions. The anterior portion is the nasal pharynx, the back section of the nasal cavity. The nasal pharynx connects to the second region, the oral pharynx, by means of a passage called an isthmus. The oral pharynx begins at the back of the mouth cavity and continues down the throat to the epiglottis, a flap of tissue that covers the air passage to the lungs and that channels food to the esophagus. The isthmus connecting the oral and nasal regions allows humans to breathe through either the nose or the mouth. The third region is the laryngeal pharynx, which begins at the epiglottis and leads down to the esophagus. Its function is to regulate the passage of air to the lungs and food to the esophagus. Air from the nasal cavity flows into the larynx, and food from the oral cavity is routed to the esophagus directly behind the larynx. The epiglottis, a cartilaginous, leaf-shaped flap, functions as a lid to the larynx and, during the act of swallowing, controls the traffic of air and food.

The mouth cavity marks the start of the digestive tube. Oval in shape, it consists of two parts: the vestibule and the mouth cavity proper.

The vestibule is the smaller outer portion, delimited externally by the lips and cheeks and internally by the gums and teeth. It connects with the body surface through the rima or orifice of the mouth. The vestibule receives the secretion of the parotid salivary glands and connects when the jaws are closed with the mouth cavity proper by an aperture on both sides behind the wisdom teeth, and by narrow clefts between opposing teeth.

The mouth cavity proper contains the tongue and is delimited laterally and in the front by the alveolar arches with the teeth therein contained. It receives the secretion from the submaxillary and sublingual salivary glands. The mouth cavity proper connects with the pharynx by a constricted aperture called isthmus faucium.

The tongue is a mobile muscular organ that can assume a variety of shapes and positions. The tongue has a relatively fixed inferior part that is attached to the hyoid bone and mandible. The rest of the tongue is called the body of the tongue. It is essentially a mass of muscles that is mostly covered by mucous membrane. The muscles in the tongue do not act in isolation. Some muscles perform multiple actions with parts of one muscle acting independently producing different, sometimes antagonistic, actions.

The tongue is partly in the mouth or oral cavity and partly in the pharynx. At rest, it occupies essentially all of the oral cavity. The posterior part of the tongue demarcates the posterior boundary of the oral cavity. Its mucous membrane is thick and freely movable.

The tongue is involved with mastication, taste, articulation, and oral cleansing. Its two main functions are forming words during speaking and squeezing food into the pharynx when swallowing.

The palate forms the arched roof of the oral or mouth cavity (the mouth) and the floor of the nasal cavities (the nose). It separates the oral cavity from the nasal cavities and the nasal pharynx. The palate consists of two regions—the hard palate anteriorly and the soft palate posteriorly.

The hard palate is vaulted and defines the space filled by the tongue when it is at rest. The hard palate has a hard bony skeleton, hence its name.

The soft palate has no bony skeleton, hence its name. The soft palate is suspended from the posterior border of the hard palate. It extends posteriorly and inferiorly as a curved free margin from which hangs a conical process, called the uvula. Muscles arise from the base of the cranium and descend into the soft palate. The muscles allow the soft palate to be elevated during swallowing into contact with the posterior pharyngeal wall. The muscles also allow the soft palate to be drawn inferiorly during swallowing into contact with the posterior part of the tongue.

The soft palate is thereby very dynamic and movable. When a person swallows, the soft palate initially is tensed to allow the tongue to press against it, to squeeze the bolus of food to the back of the mouth. The soft palate is then elevated posteriorly and superiorly against the pharyngeal wall, acting as a valve which closes and prevents passage of food into the nasal cavity.

III. Sleep and the Anatomy of the Upper Airway

Although all tissue along this conduit is dynamic and responsive to the respiratory cycle, only the pharynx, in particular the nasopharynx (the area at the soft palate and the pharyngeal walls) and the oropharynx (the area at the tongue base and the pharyngeal walls), is totally collapsible. The pharyngeal structures and individual anatomic components within this region include the pharyngeal walls, the base of the tongue, the soft palate with uvula, and the epiglottis.

The cross sectional area of the upper airway varies with the phases of the respiratory cycle. At the initiation of inspiration (Phase I), the airway begins to dilate and then to remain relatively constant through the remainder of inspiration (Phase II). At the onset of expiration (Phase III) the airway begins to dilate, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration [ref: Schwab R J, Goldberg A N. Upper airway assessment: radiographic and other imaging techniques. Otolaryngol Clin North Am 1998: 31:931-968].

Sleep is characterized by a reduction in upper airway dilator muscle activity. For the individual with obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx [ref: Isono S. Remmers J, Tanaka A Sho Y, Sato J, Nishino T. Anatomy of pharynx in patients with obstructive sleep apnea and in normal subjects. J Appl Physiol 1997:82:1319-1326.] Although this phenomenon is often accentuated at specific sites, such as the velopharyngeal level [Isono], studies of closing pressures [Isono] supports dynamic fast MRI imaging that shows narrowing and collapse usually occurs along the entire length of the pharynx [ref: Shellock F G, Schatz C J, Julien P, Silverman J M, Steinberg F, Foo T K F, Hopp M L, Westbrook P R. Occlusion and narrowing of the pharyngeal airway in obstructive sleep apnea: evaluation by ultrafast spoiled GRASS MR imaging. Am J of Roentgenology 1992:158:1019-1024].

IV. Treatment Options

To date, the only modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months.

Other current treatments for OSA include genioglossal advancement (GA) and maxillomandibular advancement (MMA). These treatments involve highly invasive surgical procedures and a long recovery time, and therefore have relatively low patient appeal.

The need remains for simple, cost-effective devices, systems, and methods for reducing or preventing sleep disordered breathing events.

SUMMARY OF THE INVENTION

The present invention provides devices, systems, and methods that employ at least one ferromagnetic structure sized and configured for placement in a tissue region. An attachment component is attached to the structure, which is held in tension to stabilize placement of the structure in the tissue region.

One aspect of the invention provides at least one anchoring structure that is sized and configured for placement in a tissue region spaced from the at least one ferromagnetic structure. According to this aspect of the invention, the anchoring structure includes an expandable structure capable of movement between a collapsed condition and an expanded condition within tissue. The attachment component couples the anchoring structure to the ferromagnetic structure to stabilize the ferromagnetic structure in the tissue region.

Another aspect of the invention provides at least one anchoring structure that is sized and configured for placement in a tissue region spaced from the at least one ferromagnetic structure. In this arrangement, the attachment component includes an attachment assembly that couples the anchoring structure to the ferromagnetic structure. The attachment assembly includes a first end coupled to the ferromagnetic structure and a second end coupled to the anchoring structure to hold the attachment component in a state of tension. According to this aspect of the invention, the second end includes a member for adjusting the state of tension.

Another aspect of the invention provides at least one elastic component coupled to the ferromagnetic material. The elastic component is sized and configured to deflect under load in a prescribed manner and to recover an initial shape when unloaded. In one embodiment, the elastic component comprises a spring-form.

Another aspect of the invention provides a system that includes the stabilized ferromagnetic structure as above described in association with at least one additional ferromagnetic structure sized and configured for placement in a desired relationship with the ferromagnetic structure to magnetically interact with the stabilized ferromagnetic structure.

Another aspect of the invention provides a method for stabilizing a desired tissue orientation by magnetic interaction between the stabilized ferromagnetic structure and the additional ferromagnetic structure. The method can be used, e.g., for reducing or preventing sleep disordered breathing events.

BRIEF DESCRIPTION OF THE DRAWINGS

FIG. 14A is an anatomic side section view of the upper airway of a human, showing the nasal and oral cavities, tongue, hard palate, soft palate, oral pharynx, chin and neck, and further showing a representative magnetic force system of a type shown in FIG. 6B comprising ferromagnetic structures implanted in a region of a tongue and soft palate/uvula that interact with a magnetic structure carried inside an airway (e.g., in an oral cavity), to resist occurrence of the tissue condition shown in FIG. 3, involving the collapse of a tongue and soft palate/uvula against the pharyngeal wall.

FIG. 14B is a perspective view of a ferromagnetic structure sized and configured to be implanted in a region of a tongue and a soft palate/uvula, and forming a part of the system shown in FIG. 14A.

FIG. 14C is a perspective view of a magnetic structure sized and configured to be worn within an airway, e.g., on teeth within an oral cavity, and forming a part of the system shown in FIG. 14A.

FIG. 14D is an anatomical anterior view of the oral cavity, showing the tongue and the hard and soft palates, and further showing the magnetic force system as shown in FIG. 14A, in which the ferromagnetic structures in the tongue and soft palate/uvula extend generally symmetrically across the centerline of the tongue and soft palate and the magnetic structure worn on teeth within an oral cavity includes magnets on both lateral sides of the oral cavity, and further showing in this arrangement the magnetic attracting forces that resist occurrence of the tissue condition shown in FIG. 3, involving the collapse of a tongue against the pharyngeal wall.

FIGS. 18A and 18B are diagrammatic representations of a finite element analysis showing the flux lines for the titrated magnetic structures of the type shown in FIGS. 16A/16B and 17A/17B, demonstrating how the magnetic attracting forces have been moderated by titration to the sensitivity of the force-distance relationship with a prescribed working space defined during normal anatomic functions of a tongue and soft palate/uvula.

FIG. 22A is an anatomic side section view of the upper airway of a human, showing the nasal and oral cavities, tongue, hard palate, soft palate, oral pharynx, chin and neck, and further showing a representative magnetic force system of a type shown in FIG. 5B, in which a ferromagnetic structure implanted in a region of a soft palate/uvula interacts with a magnetic structure that includes mobile magnetic material carried inside an airway (e.g., on teeth within an oral cavity), to resist the occurrence of the tissue condition shown in FIG. 3, involving the collapse of a tongue and soft palate/uvula against the pharyngeal wall.

FIGS. 22B and 22C are perspective views of representative embodiments of a magnetic structure sized and configured to be worn within an airway, e.g., on teeth within an oral cavity, that includes mobile magnetic material, forming a part of the system shown in FIG. 22A.

FIGS. 20A and 20B; FIGS. 21A to 21F; FIGS. 22A to 22C; or FIGS. 23A to 23C.

FIGS. 31A and 31B are, respectively, a perspective view and a top view of a representative embodiment of an asymmetric ferromagnetic structure having a non-ferromagnetic appendage that includes a non-ferromagnetic rudder-type structure to further stabilize the structure and move more tissue in response to magnetic interaction of a magnetic structure wither inside or outside the airway, or both.

FIG. 31C is an anatomical superior view of the oral cavity, showing the tongue and pharyngeal conduit, and further showing the ferromagnetic structure shown in FIGS. 31A and 31B implanted in a tongue, the view also showing a tissue condition as shown in FIG. 3, involving the collapse of a tongue against the pharyngeal wall.

FIG. 31D is an anatomical superior view of the oral cavity, like that shown in FIG. 31C, in which the ferromagnetic structure shown in FIG. 31C interacts with a magnetic structure inside an airway (e.g., on teeth within an oral cavity) having magnets only on one lateral side of the oral cavity opposite to the asymmetric ferromagnetic structure in the tongue, and further showing in this arrangement the magnetic attracting forces that resist occurrence of the tissue condition shown in FIG. 3, involving the collapse of a tongue against the pharyngeal wall.

FIGS. 40A to 40C show representative embodiments of a ferromagnetic structure implanted in an anterior or caudal anterior region of a tongue, or in the myohyoid muscle, in proximity to external magnetic structures, e.g., a mouthpiece carried within the oral cavity or an external carrier placed on or under the chin or about the neck.

DETAILED DESCRIPTION

This Specification discloses various magnetic implants and external devices, systems, and methods for the use of attracting magnetic force to maintain a patent airway. For example, the various aspects of the invention have application in procedures requiring the restriction of tissue collapse in and/or around the body, such as a passageway within the body. The devices, systems, and methods that embody features of the invention are also adaptable for use with devices, systems, and methods that are not restricted to tissue based applications.

The devices, systems, and methods are particularly well suited for treating sleep disordered breathing, including sleep apnea. For this reason, the devices, systems, and methods will be described in this context. Still, it should be appreciated that the disclosed devices, systems, and methods are applicable for use in treating other dysfunctions elsewhere in the body, which are not necessarily sleep disorder related.

I. The Tongue and the Soft Palate

A. Anatomy

Figure 1:
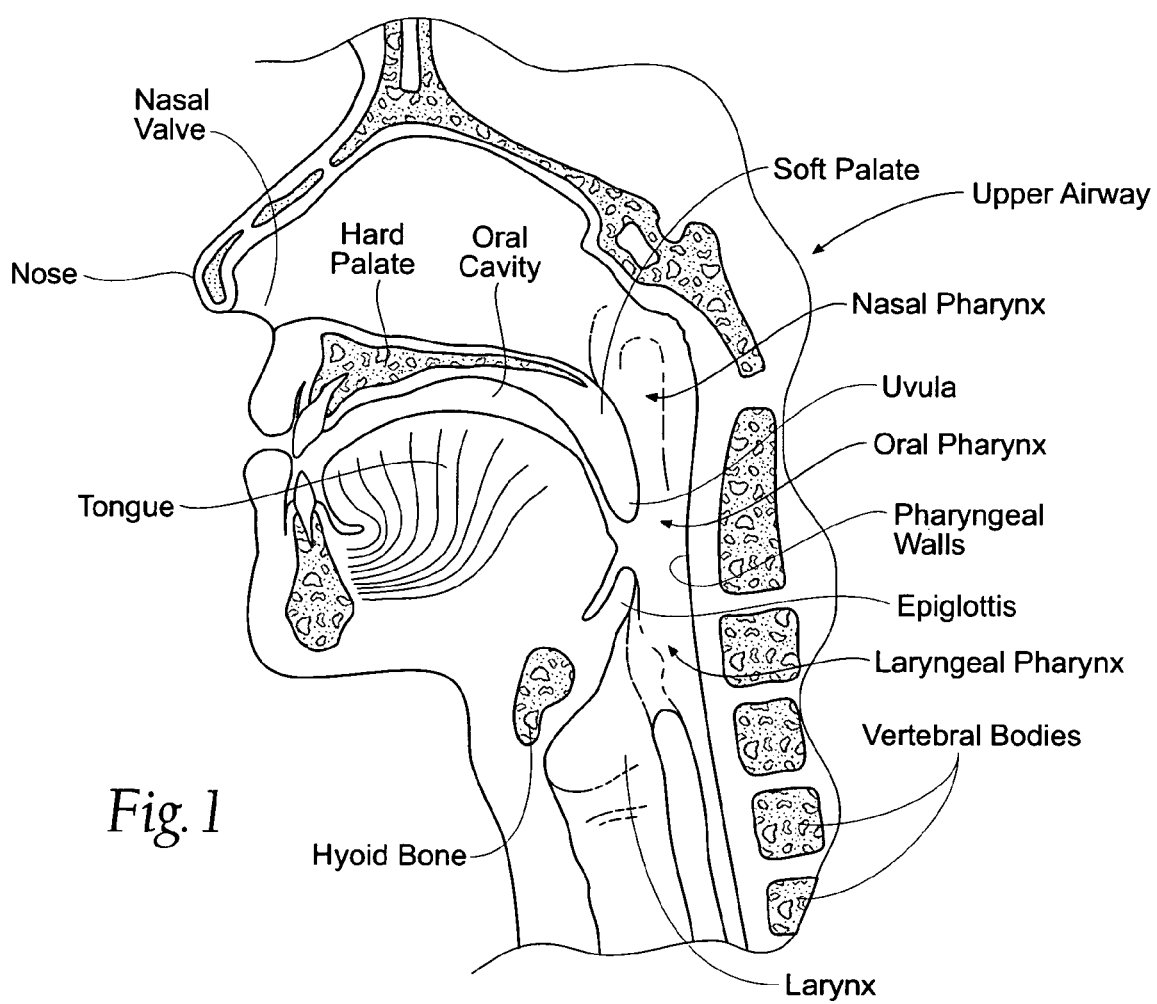
FIG. 1 is an anatomic side section view of the upper airway of a human, showing the nasal and oral cavities, tongue, hard palate, soft palate, oral pharynx, chin and neck.
Figure 2:
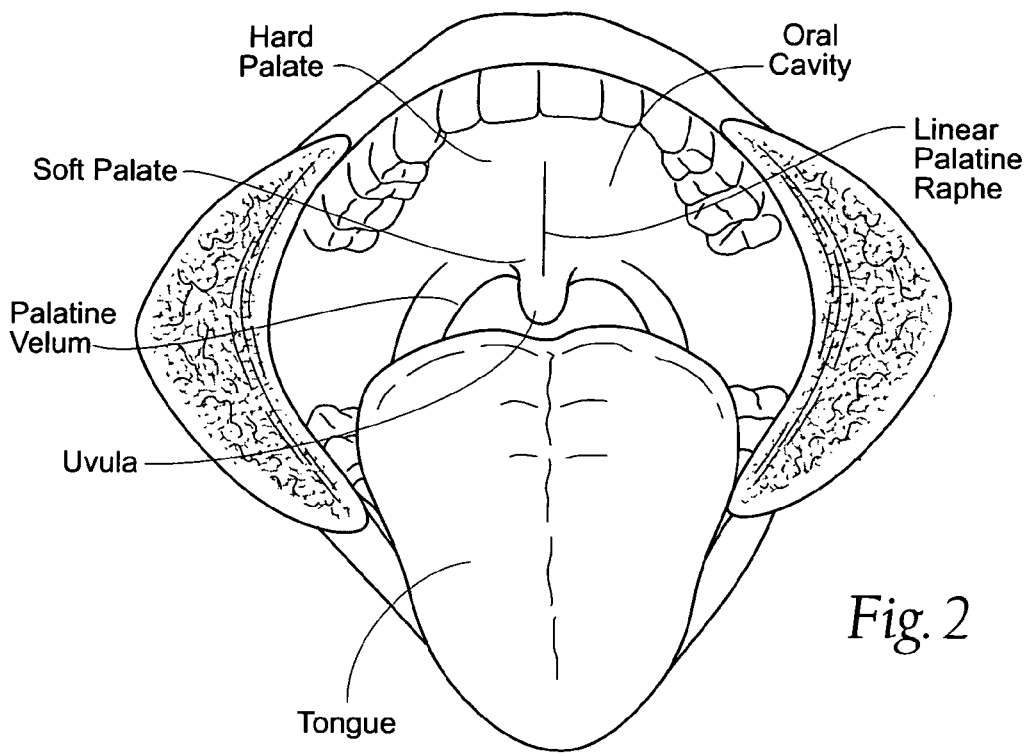
FIG. 2 is an anatomical anterior view of the oral cavity, where the tongue has been pulled towards the front to show the roof of the mouth comprising the hard palate (in the front) and the soft palate (in the back).

FIG. 2 shows an anatomical view of the oral cavity, where the tongue has been pulled towards the front. FIG. 2 shows the tongue and the roof of the mouth, i.e., the palate, as previously described and as also shown in FIG. 1. FIG. 2 shows the two parts of the palate which have also been previously described: namely, the hard palate (in the front) and the soft palate (in the back).

The hard palate is bounded in the front and laterally by the alveolar arches and gums and in the back by the soft palate. A dense structure made up by the periosteum and the mucous membrane of the mouth covers the hard palate. The linear raphé lies along the middle line of the hard palate.

The soft palate is a movable fold, suspended from the posterior border of the hard palate and forms an incomplete dividing line (septum) between the mouth and the pharynx. The soft palate comprises a mucous membrane that envelops muscular fibers, an aponeurosis, vessels, nerves, adenoid tissue, and mucous glands.

When the soft palate is relaxed and hanging, the anterior surface is concave and follows the same line as the roof of the mouth. The posterior surface of the soft palate is convex and is a continuance of the mucous membrane that covers the bottom part of the nasal cavities. The upper boundary of the soft palate attaches to the hard palate; the sides become part of the pharynx; and the lower boundary is free. The lower boundary which hangs down, separating the mouth and the pharynx is known as the palatine velum. In the middle of the lower boundary, the small, fleshy cone-shaped protuberance is called the uvula. The arches are located laterally and downwardly from the uvula. These arches are called the glossopalatine arch (the anterior arch) and the pharyngopalatine arch (the posterior arch). The palatine aponeurosis is a thin, firm fiber-filled lamella which gives support to the muscles and makes the soft palate strong.

The tongue is located over the floor of the oral cavity. In human beings the tongue is an organ that undergoes a wide variety of movements, partly because it is involved in a broad range of activities, including speech, eating and swallowing. When a human is awake, the tongue normally moves in an up and forward position. When a human is asleep, the muscles of the tongue relax and the tongue is able to move in an even broader range of directions. This movement can occur laterally, posteriorly, anteriorly, cranially, caudally, in a rolling manner, or any combinations thereof.

During the process of eating and swallowing, the uvula prevents the food from entering the nasopharynx and the muscles of the soft palate push the food down into the pharynx. The tongue can move in conjunction with other structures (i.e. with the tongue and pharyngeal wall coming together, or with the tongue and palate coming together) or independently of other structures (i.e. tongue movement without palate, pharyngeal wall, or epiglottis movement).

B. The Tongue/Soft Palate and Sleep Apnea

Sleep apnea occurs when the airway becomes obstructed; hypopnea occurs when the airway is partially obstructed. Sleep apnea takes many forms; closure of the airway can occur at any number of anatomical structures along the airway, including any combination of the tongue, soft palate, epiglottis, and pharyngeal wall. For example, the tongue may collapse with respect to the pharyngeal wall, or both the base of the tongue and the pharyngeal wall may collapse at the same time. Likewise, the soft palate/uvula may collapse with respect to the pharyngeal wall and/or tongue, or both the soft palate/uvula and/or tongue and/or the pharyngeal wall may collapse at the same time. Thus, sleep apnea may be treated by either preventing the collapse of the tongue, pharyngeal wall, soft palate/uvula independently, and/or one or more of the tongue base, the pharyngeal wall, and/or the soft palate/uvula at the same time.

Figure 3:
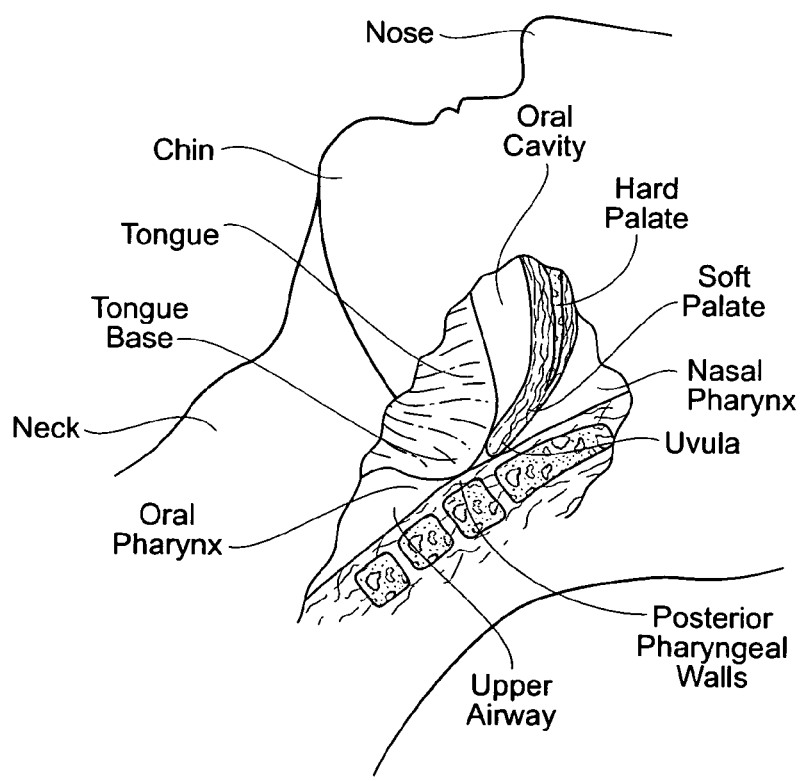
FIG. 3 is an anatomical side view, with sections partly broken away and in section, of a human suffering from one form of sleep apnea involving the soft palate, showing how the tongue base, the soft palate, and the uvula lean against the pharyngeal wall, effectively closing off the airway, resulting in an apneic event.

FIG. 1 is an anatomical side view of the upper airway system in a normal patient, showing the nasal and oral cavities, tongue, hard palate, soft palate, oropharynx, chin and neck. FIG. 3 shows an anatomical side view of a patient suffering from one form of sleep apnea involving at the same time the tongue, the pharyngeal wall, and the soft palate/uvula. As shown in FIG. 3, the tongue base, the soft palate, and the uvula lean against the pharyngeal wall, effectively closing off the airway. An apneic episode can occur as a result.

II. Attracting Magnetic Force Systems

A. Overview

1. Resisting Collapse of the Tongue
(The Tongue System)

FIGS. 4A to 4D show in a diagrammatic way representative embodiments of a magnetic force system 10a that resists, at least in part, the tissue condition shown in FIG. 3, involving the collapse of the tongue against the pharyngeal wall. This system 10a in its various embodiments will be in shorthand called the Tongue System. The Tongue System 10a includes one magnetic structure 12 and one magnetic structure 14 to create an attracting magnetic force between the two structures, which maintains the tongue in a position spaced away from the posterior pharyngeal wall, as FIGS. 4A, 4B, 4C, and 4D show. The magnetic force field resists posterior movement of the tongue during sleep, keeping the airway open. An apneic episode is avoided.

Figure 4A:
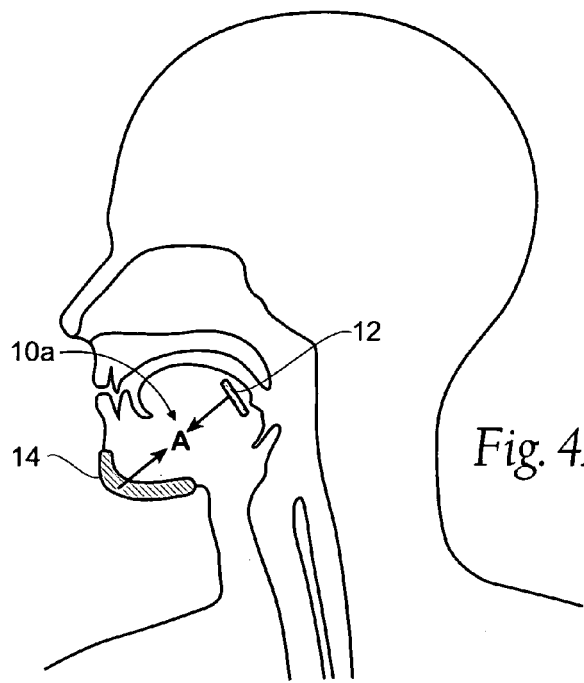
FIGS. 4A to 4D show in a diagrammatic way representative embodiments of a magnetic force system that resists occurrence of the tissue condition shown in FIG. 3, involving the collapse of a tongue against the pharyngeal wall, with FIGS. 4A and 4C showing magnetic interaction of a ferromagnetic structure implanted in regions of a tongue with a magnetic structure carried outside an airway (e.g., on a chin and/or jaw), and with FIGS. 4B and 4D showing magnetic interaction of a ferromagnetic structure implanted in regions of a tongue with a magnetic structure carried inside an airway (e.g., in an oral cavity).
Figure 4B:
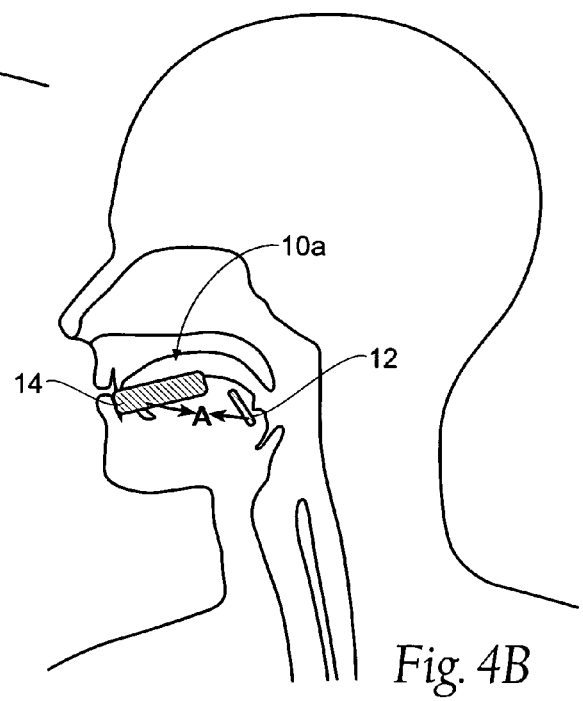

In the representative embodiments shown in FIGS. 4A and 4B, the magnetic structure 12 is positioned in or on the tongue. More specifically, magnetic structure 12 can be positioned either in the anterior or in the posterior region of the tongue. In FIG. 4A, the magnetic structure 14, which the magnetic structure 12 interacts with, is positioned outside the airway (e.g., on the chin), whereas in FIG. 4B, the magnetic structure 14 is positioned within the airway (e.g., in the oral cavity).

Figure 4C:
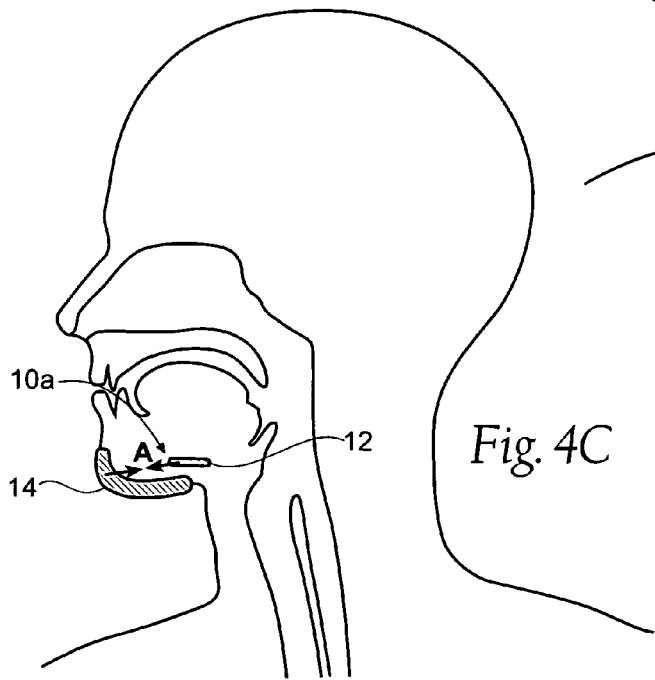
Figure 4D:
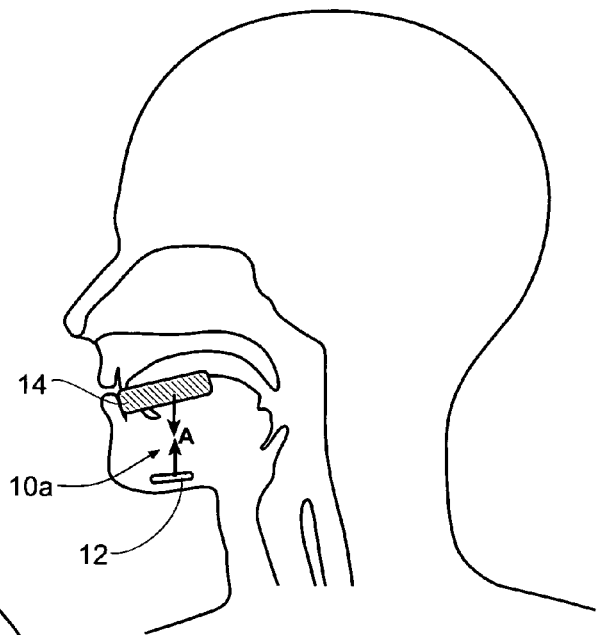

In the representative embodiments shown in FIGS. 4C and 4D, the magnetic structure 12 is positioned in the general area between the mandible and the hyoid bone, either in or on the hyoid muscles (e.g. one or more of the suprahyoid muscles such as the mylohyoid muscles, the geniohyoid muscles, or the stylohyoid muscles, or the digastric muscles), or under the skin. In FIG. 4C, the magnetic structure 14, which the magnetic structure 12 interacts with, is positioned outside the airway (e.g., on the chin), whereas in FIG. 4D, the magnetic structure 14 is positioned within the airway (e.g., in the oral cavity).

2. Resisting Collapse of the Soft Palate
(The Soft Palate System)

Figure 5A:
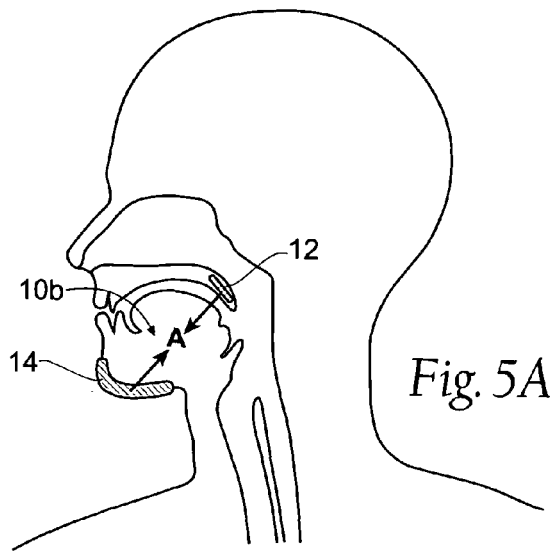
FIGS. 5A and 5B show in a diagrammatic way representative embodiments of a magnetic force system that resists occurrence of the tissue condition shown in FIG. 3, involving the collapse of a soft palate/uvula against the pharyngeal wall, with FIG. 5A showing magnetic interaction of a ferromagnetic structure implanted in a soft palate/uvula with a magnetic structure carried outside an airway (e.g., on a chin and/or jaw), and with FIG. 5B showing magnetic interaction of a ferromagnetic structure implanted in a soft palate/uvula with a magnetic structure carried inside an airway (e.g., in an oral cavity).
Figure 5B:
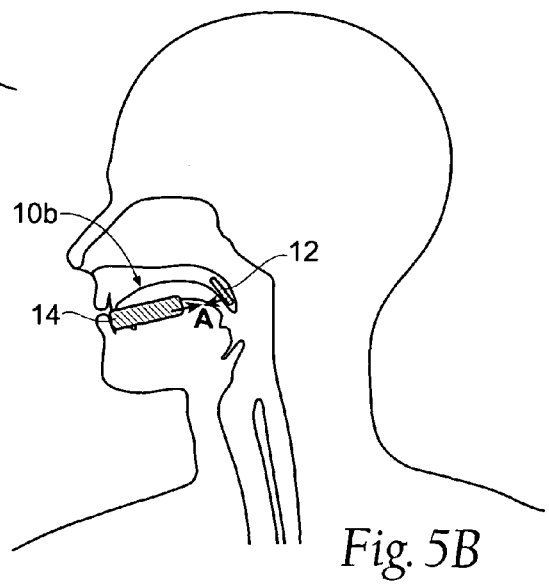

FIGS. 5A and 5B show in a diagrammatic way representative embodiments of a magnetic force system 10b that resists, at least in part, the tissue condition shown in FIG. 3, involving the collapse of the soft palate/uvula against the pharyngeal wall. This system 10b in its various embodiments will be in shorthand called the Soft Palate System. The Soft Palate System 10b includes one magnetic structure 12 and one magnetic structure 14 to create a magnetic force field, which maintains the soft palate/uvula in a position spaced away from the posterior pharyngeal wall, as FIGS. 5A and 5B show. The magnetic force field resists posterior movement of the soft palate/uvula during sleep, keeping the airway open. An apneic episode is avoided.

In the representative embodiments shown in FIGS. 5A and 5B, the magnetic structure 12 is positioned in or on the soft palate/uvula. In FIG. 5A, the magnetic structure 14, which the magnetic structure 12 interacts with, is positioned outside the airway (e.g., on the chin), whereas in FIG. 5B, the magnetic structure 14 is positioned within the airway (e.g., in the oral cavity).

3. Resisting Collapse of the Tongue and the Soft Palate (The Combined System)

Figure 6A:
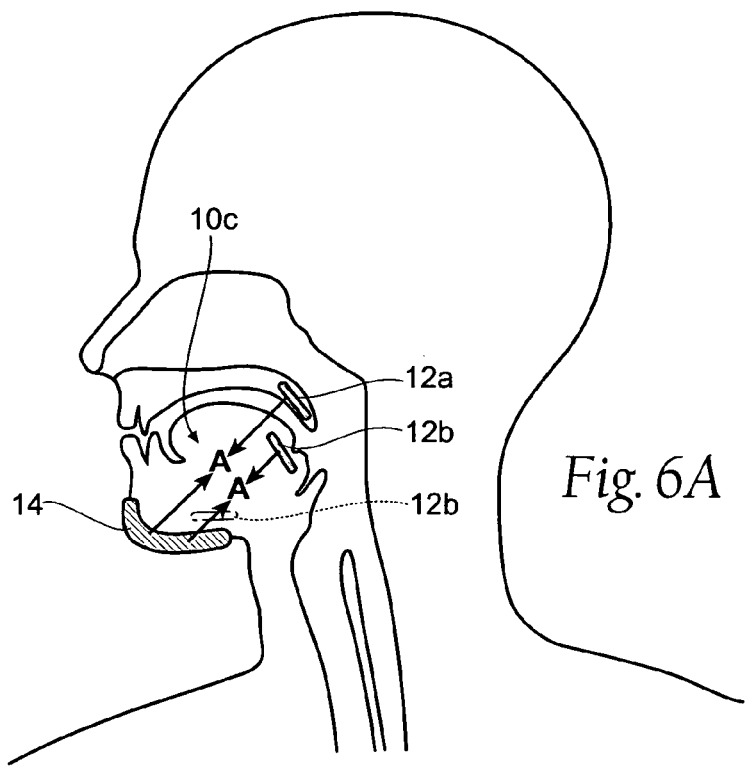
FIGS. 6A and 6B show in a diagrammatic way representative embodiments of a magnetic force system that resists occurrence of the tissue condition shown in FIG. 3, involving the collapse of both a tongue and a soft palate/uvula against the pharyngeal wall, with FIG. 6A showing magnetic interaction of ferromagnetic structures implanted in a tongue and a soft palate/uvula with a magnetic structure carried outside an airway (e.g., on a chin and/or jaw), and with FIG. 6B showing magnetic interaction of ferromagnetic structures implanted in a tongue and a soft palate/uvula with a magnetic structure carried inside an airway (e.g., in an oral cavity).
Figure 6B:
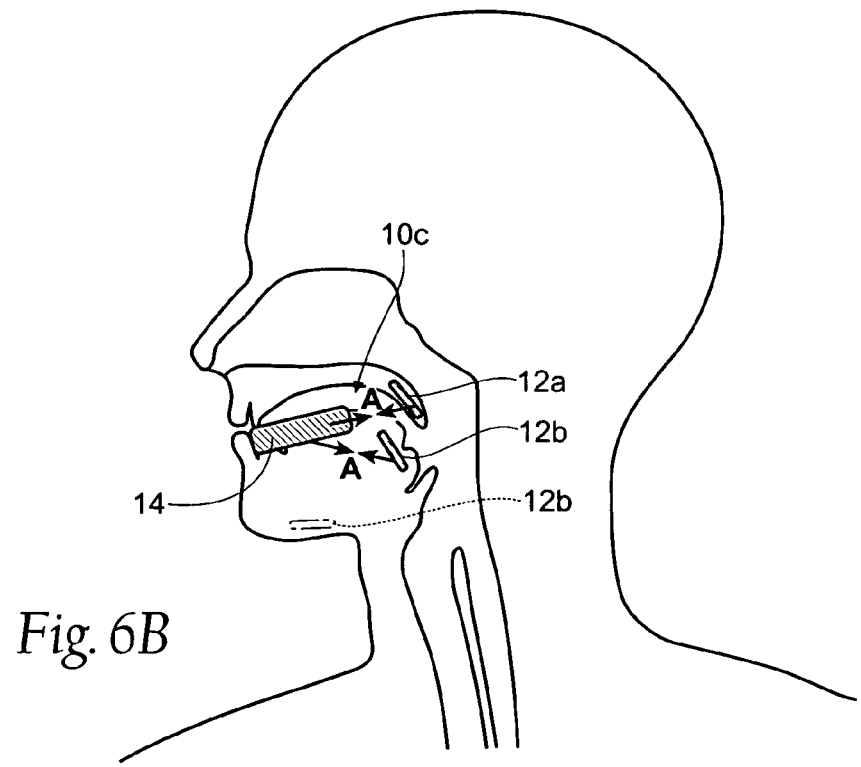

FIGS. 6A and 6B show in a diagrammatic way representative embodiments of a magnetic force system 10c that resists, at least in part, the tissue condition shown in FIG. 3, involving the collapse of both the tongue and the soft palate/uvula against the pharyngeal wall. This system 10c in its various embodiments will be in shorthand called the Combined System. The Combined System 10c includes two magnetic structures 12a and 12b and one magnetic structure 14 to create a magnetic force between the two, which maintains both the tongue and the soft palate/uvula in a position spaced away from the posterior pharyngeal wall, as FIGS. 6A and 6B show. The magnetic force field resists posterior movement of both the tongue and the soft palate/uvula during sleep, keeping the airway open. An apneic episode is avoided.

In the representative embodiments shown in FIGS. 6A and 6B, the magnetic structure 12a is positioned in or on the soft palate/uvula and the magnetic structure 12b is positioned in or on the posterior (back) of the tongue. In FIG. 6A, the magnetic structure 14, which the magnetic structures 12a and 12b interact with, is positioned outside the airway (e.g., on the chin), whereas in FIG. 6B, the magnetic structure 14 is positioned within the airway (e.g., in the oral cavity). It should be appreciated that the magnetic structure 12b can, alternatively, be positioned in the general area between the mandible and the hyoid bone, either in or on the muscles (e.g. mylohyoid, geniohyoid, or digastric), or under the skin, in the manner shown in phantom lines in FIGS. 6A and 6B, in the manner previously shown in FIGS. 4C and 4D).

B. Placement of the Ferromagnetic Structures

The magnetic force systems 10a, 10b, and 10c can be variously constructed. In the illustrated arrangements, all the force systems 10a, 10b, and 10c include in their most basic form the two structures 12 and 14. One structure 12 is placed in or on tissue that is relatively mobile and subject to collapse, if not restrained from doing so. The other structure 14 is placed in or on tissue that is, relatively speaking, immobile, relative to the direction of collapse.

The structures 12 and 14 comprise ferromagnetic materials. The ferromagnetic materials of the structures 12 and 14 are sized, selected, and arranged to magnetically interact by developing between the structures 12 and 14 a magnetic force. The magnetic force includes at least one vector or component that magnetically attracts the structure 12 in or on the mobile tissue toward the structure 14 in or on the relatively immobile tissue. Posterior movement or other movement which could lead to an apneic or hypopneic obstruction or narrowing of the relatively mobile tissue is thereby resisted.

1. The First Structure

The first structure 12 is internally placed in or on the relatively mobile tissue in the airway targeted for treatment. In the Tongue System 10a (FIGS. 4A to 4D), the targeted tissue is tongue tissue, and, in particular, tissue at or near the posterior part (base) of the tongue across from the pharyngeal wall (FIGS. 4A and 4B) or in the general area between the mandible and the hyoid bone, either in or on the muscles (e.g. mylohyoid, geniohyoid, or digastric), or under the skin (FIGS. 4C and 4D). In the Soft Palate System 10b (FIGS. 5A and 5B) the targeted tissue is the soft palate/uvula across the airway from the pharyngeal wall. In the Combined System 10c (FIGS. 6A and 6B), the targeted tissue is both tongue tissue (or, alternatively, in the general area between the mandible and the hyoid bone, either in or on the muscles (e.g. mylohyoid, geniohyoid, or digastric), or under the skin) and the soft palate/uvula across the airway from the pharyngeal wall.

Due to its interior placement, the ferromagnetic structure 12 is desirably sized and configured for relatively long-term placement or implantation in tissue.

2. The Second Structure

As previously described, the second structure 14 can be placed either externally in or on relatively immobile tissue outside the airway or internally in or on relatively immobile tissue within an airway. The structure 14 is placed to magnetically interact with the structure 12 by developing between the ferromagnetic materials on the structures 12 and 14 a magnetic force that includes at least one vector or component that magnetically attracts the structure 12 in or on the mobile tissue toward the structure 14 in or on the relatively less mobile tissue.

In the Tongue System 10a (FIGS. 4A to 4D), the magnetic attracting force between the two ferromagnetic structures 12 and 14 resists posterior or other movement of the tongue toward the posterior pharyngeal wall. In the Soft Palate System 10b (FIGS. 5A and 5B), the magnetic attracting force between the two ferromagnetic structures 12 and the one ferromagnetic structure 14 resists posterior or other movement of the soft palate/uvula toward the posterior pharyngeal wall. In the Combined System 10c (FIGS. 6A and 6B), the magnetic attracting force between the two ferromagnetic structures 12 and ferromagnetic structure 14 resists posterior movement of both the tongue and the soft palate/uvula toward the posterior pharyngeal wall. In all systems 10a, 10b, and 10c, the magnetic force prevents, in whole or in part, the occurrence of the airway-occluding tissue condition shown in FIG. 3. As FIGS. 4A to 4D, 5A and 5B, and 6A and 6B show, the magnetic force between the first and second ferromagnetic structures 12 and ferromagnetic structure 14 works to keep the airway open (i.e., patent) during sleep.

Due to its placement, the ferromagnetic structure 14 is desirably sized and configured to be removable, so that it can be temporarily placed into association with the more permanent ferromagnetic structure 12 and thereafter removed, when desired, from the association. Thus, the ferromagnetic structure 14 can be placed into association with the internal ferromagnetic structure 12 when the presence of the magnetic force field is desired, e.g., during sleep, and can be removed at other times. A removable structure 14 also has the advantage of being easily and accurately titrated (i.e. increasing or decreasing the force to optimize the performance of the system). This titration could be accomplished by switching different ferromagnetic materials of various strengths by a clinician or by the user and/or by adjusting the relative position or distance of the removable structure 14 with respect to the internal structure 12.

a. External Placement

In FIGS. 4A, 4C, 5A, and 6A, the second structure 14 is shown placed on relatively immobile tissue externally outside the airway. More particularly, in FIGS. 4A, 4C, 5A, and 6A, the second structure 14 is shown placed externally on or under the chin or lower jaw. Various ways of placing the structure 14 in this position are possible.

Figure 7A:
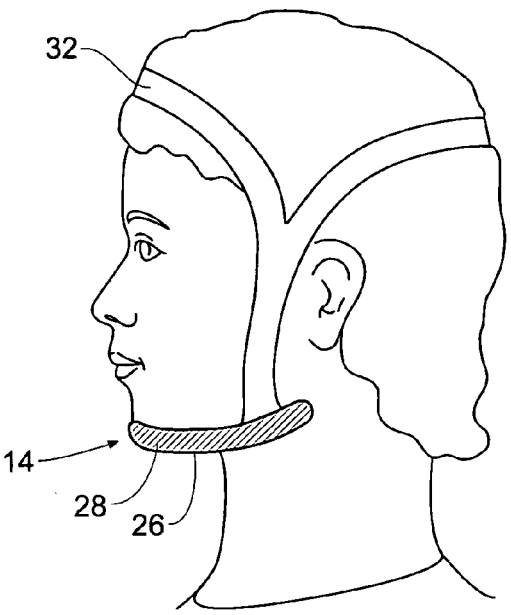
FIGS. 7A to 7C show representative embodiments of magnetic structures sized and configured to be worn on a jaw and/or a chin outside an airway to magnetically interact with one or more magnetic structures carried within an airway, e.g., in or on a tongue and/or soft palate/uvula in the manner shown in FIGS. 4A, 4C, 5A, and 6A.

For example, as shown in FIG. 7A, the external ferromagnetic structure 14 can be shaped, sized and configured as a carrier 28 that can be secured at the level of the mandibular joint by, e.g., headgear that includes a strap 32 that fits over the head. As will be described in greater detail later, the carrier 28 includes an array of one or more ferromagnetic materials 26 positioned and arranged to attract the ferromagnetic materials in the internal structure 12 positioned in or on the tongue, the soft palate/uvula, or both.

Figure 7B:
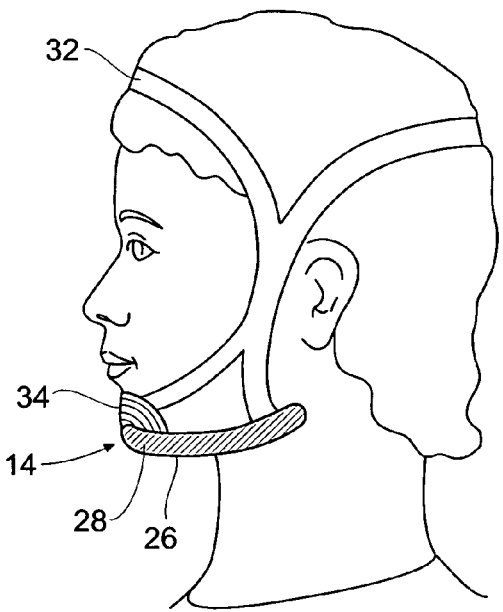

Alternatively, as FIG. 7B shows, the carrier 28 of the external ferromagnetic structure 14 can be shaped to include a cup 34 that fits over the chin, to add further stability and comfort. In this arrangement, the headgear strap 32 attaches to the carrier 28 at the level of the mandibular joint, as well as to the chin cup 34, helping to immobilize the position of the headgear.

Figure 7C:
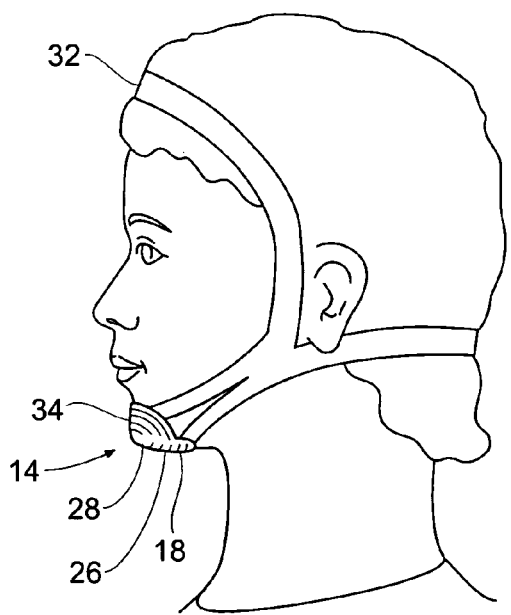

As FIG. 7C shows, the carrier 28 can be shaped, sized, and configured as a chin cup 34 that includes an extension, which extends a measured minimum distance (e.g., at least 4 cm) under the chin below the tongue. In this arrangement, the extension carries at least one ferromagnetic material 26, which interacts with the ferromagnetic materials in the internal structure 12 positioned in or on the tongue. In this embodiment the headgear strap 32 can fit over the head and attach to both the chin cup and its extension under the chin. This embodiment is particularly useful when the therapeutic objective is to principally target resistance to posterior movement of the tongue.

Figure 8A:
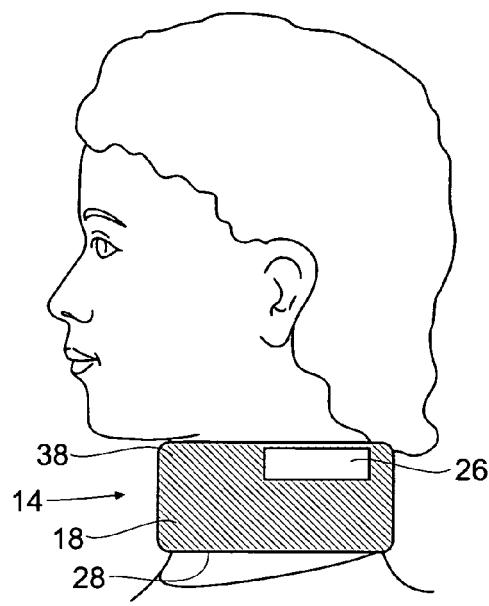
FIGS. 8A and 8B show representative embodiments of magnetic structures sized and configured to be worn about a neck outside an airway to magnetically interact with one or more ferromagnetic structures carried within an airway, e.g., in or on a tongue and/or soft palate/uvula in the manner shown in FIGS. 4A, 4C, 5A, and 6A.

In an alternative arrangement, the second structure 14 can be placed around the neck. As shown in FIG. 8A, the second structure 14 comprises a carrier 28 that includes an array of one or more ferromagnetic materials 26. The carrier 28 includes a neck collar 38, which serves to position and orient the ferromagnetic materials 18 to attract the ferromagnetic materials in the internal structure 12 positioned in or on the tongue, the soft palate/uvula, or both.

Figure 8B:
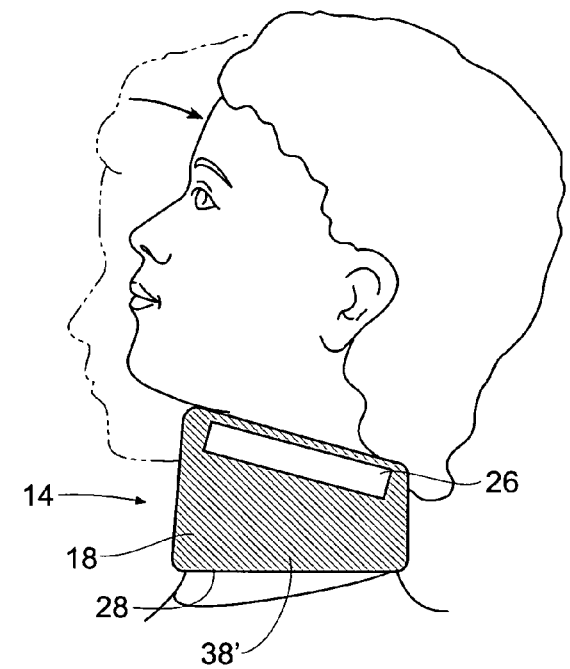

In the embodiment shown in FIG. 8B, an anterior part of the neck collar that fits under the chin is higher than the posterior part that fits under the back of the head. This configuration raises the level of the chin and serves to extend the neck, by tilting the head back and raising the chin. The embodiment shown in FIG. 8B mimics the extension of the neck accomplished during CPR. The extension may add a mechanical enhancement to the magnetic force field, helping to maintain or further open up the airway.

Benefits of using external magnetic devices include: (1) larger and stronger magnets may be used than could be either implanted or affixed to an appliance worn in the mouth (as will be described in greater detail later); (2) external devices are easily removed, so that the force delivered need only be experienced when the patient wishes to sleep, and not during eating or speech thus minimizing the effect of magnetic force on these activities; and (3) without need for surgical intervention, the amount and direction of the magnetic forces can be changed. This is accomplished by exchanging magnet types and sizes and by changing the location of the magnets within the external device.

b. Internal Placement

Alternatively, the second structure 14 can be placed in or on relatively immobile tissue internally inside the airway, e.g., within an oral cavity in proximity to the first structure 12 (which is desirably placed in or on a tongue and/or soft palate/uvula). For example (as FIGS. 9A, 9B, 9C, 9D, and 9E show), the second structure 14 can be shaped, sized and configured to be fitted inside the mouth in various positions along the inner or outer edge of the lower teeth or covering the top of the lower or upper teeth, the second structure also comprising magnetic materials that are generally aligned with, on top of, or below the tongue. The structure could, in principle, also be placed on the upper teeth.

Figure 9A:
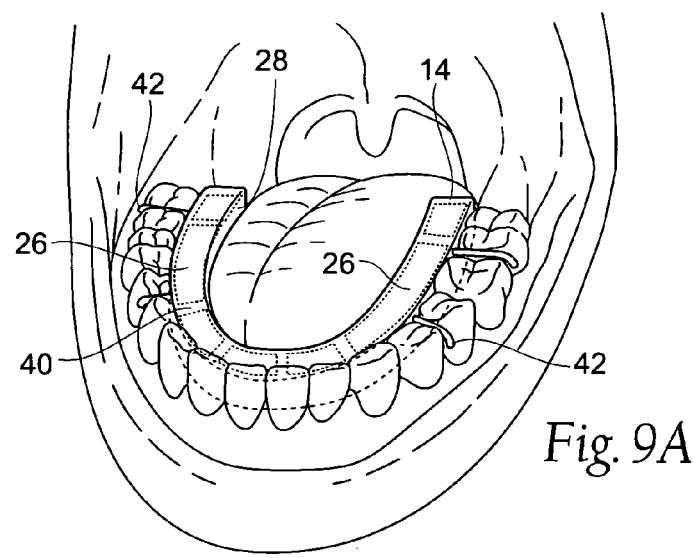
FIGS. 9A to 9E show representative embodiments of a magnetic structures sized and configured to be worn within an airway, e.g., on teeth within an oral cavity, to magnetically interact with ferromagnetic structures carried within an airway, e.g., in or on a tongue and/or soft palate/uvula in the manner shown in FIGS. 4B, 4D, 5B, and 6B.

For example, in FIG. 9A, the second ferromagnetic structure 14 comprises a carrier 28 that takes the form of a mouthpiece 40 that fits along the inside edge of the lower teeth. An array of one or more ferromagnetic materials 26 is carried by the carrier 28, as will be described in greater detail later. In the illustrated embodiment, the mouthpiece 40 attaches to the lower teeth in a suitable manner, e.g., with the hooks 42 as shown.

Figure 9B:
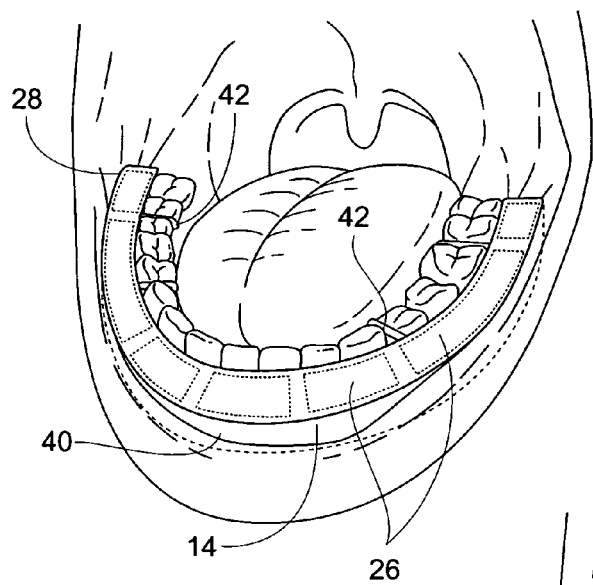

FIG. 9B shows an alternative arrangement. In this arrangement, the second ferromagnetic structure 14 comprises a carrier 28 that takes the form of a mouthpiece 40 that fits along the outside edge of the lower teeth in a suitable manner, e.g., the two hooks 42 as shown. An array of one or more ferromagnetic materials 26 is carried by the carrier 28, as will be described in greater detail later.

Figure 9C:
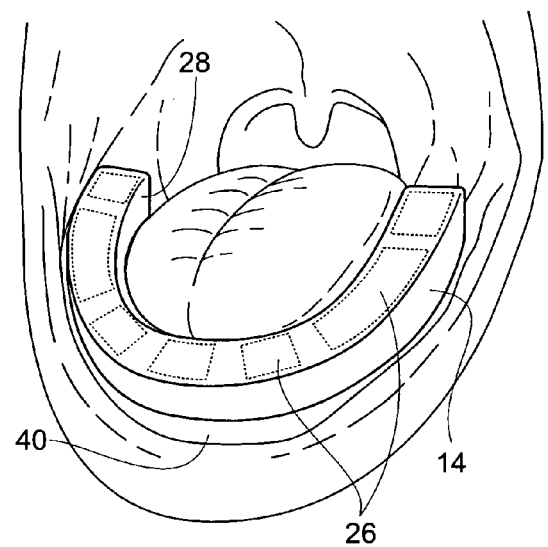

FIG. 9C shows another alternative arrangement. In this arrangement, the second ferromagnetic structure 14 comprises a carrier 28 that takes the form of a mouthpiece 40 that is pre-formed by molding to fit and cover the lower teeth. An array of one or more ferromagnetic materials 26 is carried by the carrier 28, as will be described in greater detail later.

Figure 9D:
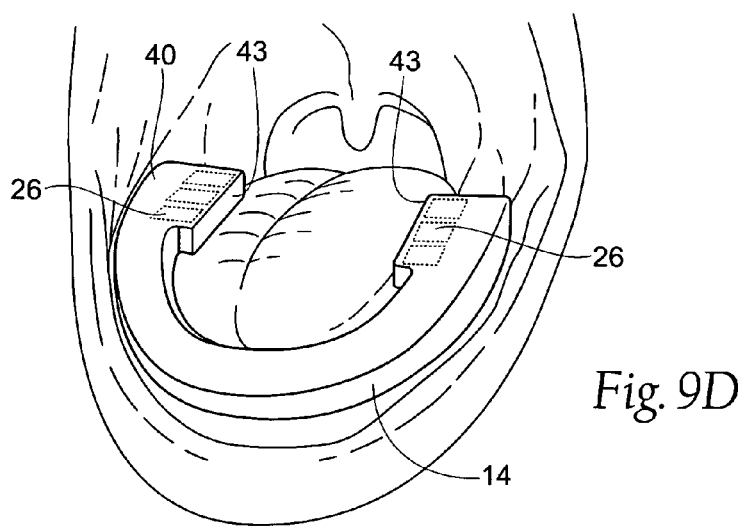
Figure 9E:
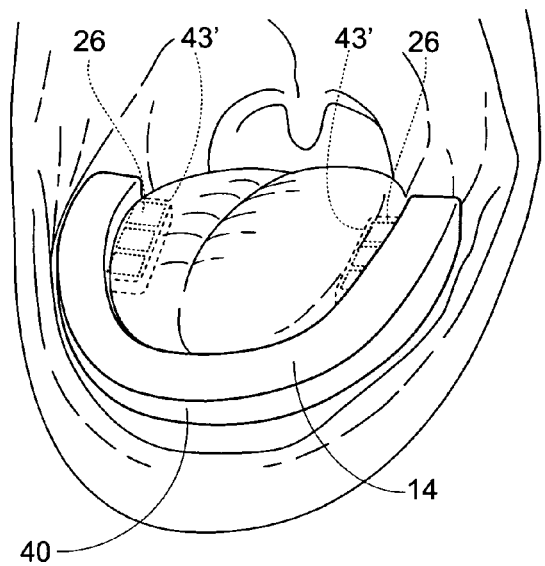

FIGS. 9D and 9E are other alternative embodiments of the mouthpiece 40 of the type shown in FIG. 9C, which fit over the lower teeth. In FIGS. 9D and 9E, the mouthpiece 40 includes one or more protrusions 43 that extend medially from the teeth into the oral cavity. In FIG. 9D, the one or more protrusions extend over the tongue. In FIG. 9E, the one or more protrusions 43' extend beneath the tongue. The protrusions carry an array of one or more ferromagnetic materials 26. In this way, the ferromagnetic materials 26 can be placed in close superior alignment (FIG. 9D) or inferior alignment (FIG. 9E) with the ferromagnetic materials 26 in the first structure 12 in the tongue, and/or in close inferior alignment with the ferromagnetic materials 26 in the first structure 12 in the soft palate/uvula.

Alternative embodiments to the mouthpieces 40 shown in FIGS. 9A to 9D are also envisioned where the carrier 28 fits over the upper teeth.

The configuration and placement of the various mouthpieces 40 in FIGS. 9A, 9B, 9C, 9D, and 9E physically locate the ferromagnetic materials 26 of the second ferromagnetic structure 14 in relatively close proximity to a ferromagnetic structure 12 placed in or on the tongue and/or soft palate/uvula. The proximity increases the magnitude of the magnetic field within the airway necessary to achieve the desired therapeutic effect. Thus, the proximity makes possible the use of relatively smaller ferromagnetic materials in both structures 12 and 14, when compared to an external second magnetic structure in a collar, head gear or other location.

C. Configuration of the Ferromagnetic Structures

Figure 10:
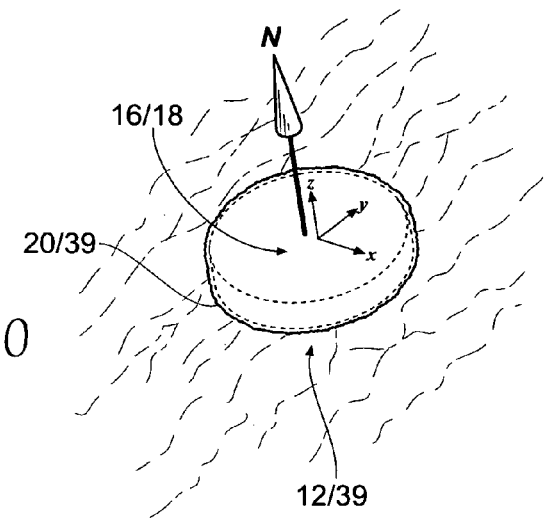
FIG. 10 is a perspective view of a ferromagnetic material sized and configured for implantation as part of a magnetic force system shown in FIGS. 4A to 4D, or 5A or 5B, or 6A or 6B.

As seen in FIG. 10, in its most basic form, the magnetic structures 12 and 14 of the magnetic force system 10 each comprises at least one ferromagnetic material. The ferromagnetic material(s) of the magnetic structure 12 will be identified by reference number 16, the ferromagnetic material(s) for the magnetic structure 14 will be identified by reference number 18. The ferromagnetic materials 16 of the first structure 12 are placed in or on the targeted tissue regions (tongue and/or soft palate/uvula). The ferromagnetic materials 18 of the second structure 14 are placed under the chin, the lower jaw, along the inner or outer edge of the lower teeth, or on top of the lower teeth, along the inner or outer edge of the upper teeth, or beneath the upper teeth. The ferromagnetic materials 16 and 18 of the magnetic structures 12 and 14, forming the force systems 10a, 10b, and 10c are placed to magnetically interact and stabilize the tongue and/or soft palate/uvula, thereby resisting the collapse of tissue in the airway between the tongue and/or soft palate/uvula and the pharyngeal wall during sleep.

1. Orientation of Magnetic Poles

Each ferromagnetic material 16 and 18 can comprise a permanent magnet. A permanent magnet is characterized as a material showing resistance to external demagnetizing forces once being magnetized. That is, a high external magnetic field is required in order to remove the residual magnetism of a permanent magnet. Stated differently, a permanent magnet has very high intrinsic coercivity, which is a measure of its resistance to demagnetization.

A permanent magnet possesses poles of opposite polarity. The poles are regions of a magnet (usually at the end of the magnets) where the external magnetic field is strongest. Relative to Earth's magnetic poles, if the magnet is free to turn, one pole will point to the magnetic north pole of the Earth, and is thus called a north pole of the magnet, which is indicated by N in the drawings or otherwise called a N-pole. The opposite pole is called a south pole of the magnet, which is indicated by S in the drawings or otherwise called an S-pole.

According to physical laws, poles of like polarity (N-N or S-S) repel each other with a magnetic force. Conversely, poles of unlike polarity (N-S or S-N) attract each other with a magnetic force. Thus, structures 12 and 14 incorporating permanent magnets will repel each other when like poles of the structures 12 and 14 (N-N or S-S) are oriented to face each other, and likewise attract each other when opposite poles of the structures 12 and 14 (N-S or S-N) are oriented to face each other. The magnitude of the force of magnetic attraction or repulsion depends on the strength of the magnets and the distance between the poles.

Examples of known permanent magnet materials include alloys of Neodymium-Iron-Boron (NdFeB), alloys of Aluminum-Nickel-Cobalt (AlNiCo), and Samarium Cobalt (SmCo). An electromagnet (current flowing through a coil of wire) can be substituted for a permanent magnet.

In the magnetic force systems 10a, 10b, and 10c shown in, respectively, FIGS. 4A to 4D, 5A and 5B, and 6A and 6B the magnetic materials 16 and 18 are oriented such that opposite poles (N-S or S-N) generally face each other across lower jaw or across tongue tissue. Thus, the first and second magnetic structures 12 and 14 are referred to as having opposite polarities. The structures 12 and 14 will magnetically interact by the generation of a magnetic force between them. The nature of the magnetic force will generally be called in shorthand for purposes of description an "attracting" magnetic force, because it involves an interaction between magnetic poles of the unlike polarities. However, it should be appreciated that the magnetic force generated between the structures 12 and 14 can include a torquing force (i.e., a force or moment of a force that tends to rotate the internal structure 12 in the more mobile tissue of the tongue and/or soft palate/uvula about an axis), and/or a decentering force (i.e., a force in essentially a lateral or side-to-side direction that tends to offset the internal structure 12 in the tongue and/or soft palate/uvula left or right, again depending the mobile tissue region being targeted), or a combination of two or more attracting, torquing, and decentering forces. One or more of these magnetic forces collectively can prevent the tongue and/or soft palate (depending on the mobile tissue region being targeted) from moving in a posterior direction and closing, obstructing, or restricting the pharyngeal conduit or airway. One of the predominant advantages of the attracting systems is their ability to decrease or eliminate the significant and problematic decentering and torquing forces seen in repelling magnetic systems in treating OSA.

It should be appreciated that the structure 12 in the more mobile targeted tissue region can include a ferromagnetic material 16 that is itself not magnetized, but that nevertheless is attracted to a ferromagnetic material 18 on the structure 14 in the less mobile targeted tissue region, which is magnetized. Therefore, the ferromagnetic material(s) 16 of the structure 12 can comprise an un-magnetized material, e.g., ferrous plate, on which the magnetized ferromagnetic material 18 of the structure 14 exerts an attractive magnetic force. The terms "ferromagnetic" material as used in this specification is therefore not necessarily limited to an object that exhibits magnetic properties (i.e., an object that is magnetized), but also encompasses an object made of a material that is not itself magnetized but which is attracted to another object that is magnetized.

2. Magnetic Structures

As previously described in general terms, the ferromagnetic material 16 of the first structure 12 can be magnetized or un-magnetized. However, it is desirably permanently magnetized and therefore will be described as "magnetic". The magnetic material 16 is placed in or on tissue in the airway. The term placed "in or on" is intended to mean that the magnetic material 16 can be placed either on surface tissue or implanted within tissue. For longevity and comfort, the material 16 is desirably implanted within tissue. In the illustrated embodiments, the targeted tissue can comprise a region of the tongue, a region of the soft palate/uvula, or both.

As previously generally described, the ferromagnetic material 18 of the second structure 14 is also desirably permanently magnetized and therefore will be described as "magnetic". The magnetic material 18 is placed externally of the airway under the chin or lower jaw, or internally within the airway along the inner or outer edge of the lower teeth, on top of the teeth, or on top of or below the tongue. As previously described, when externally located, the magnetic material 18 is desirably mounted or carried in an individually fitted chin strap or neck collar. When internally located, the magnetic material 18 is desirably mounted or carried in an oral mouthpiece fitted to the lower teeth. In this way, the magnetic material 18 can be located externally under the lower jaw, or internally along the inner or outer edge of the lower teeth, on top of the lower teeth, on top of or below the tongue to magnetically interact with the material 16 placed on or implanted within tissue in a region of the tongue, a region of the soft palate/uvula, or both.

The permanent magnetic materials 16 and 18 can each be configured in various ways and take various shapes, e.g., cylindrical, square, rectangular, or other polygons. A given magnetic material 16 or 18 of a given internal component, implant 12 or external component 14 can comprise a single or discrete source of magnetism having a given desired polar orientation. For example, a given magnetic material 16 or 18 can comprise a single permanent magnet, as shown in FIG. 10. Bonded permanent magnets may also be used. Bonded magnets can be flexible or rigid, and consist of powdered NdFeB, Ferrite, or SmCo permanent magnet materials bonded in a flexible or rigid substrate of e.g., rubber, nitrile, polyethylene, epoxy, polyvinyl chloride, silicone, rubber, or nylon. The forming of the bonded magnet can be achieved by extrusion, compression molding, injection molding, calendering, or printing. Bonded magnets enable unique flexible designs, and durable high tolerance shapes that are otherwise difficult to achieve.

Figure 11:
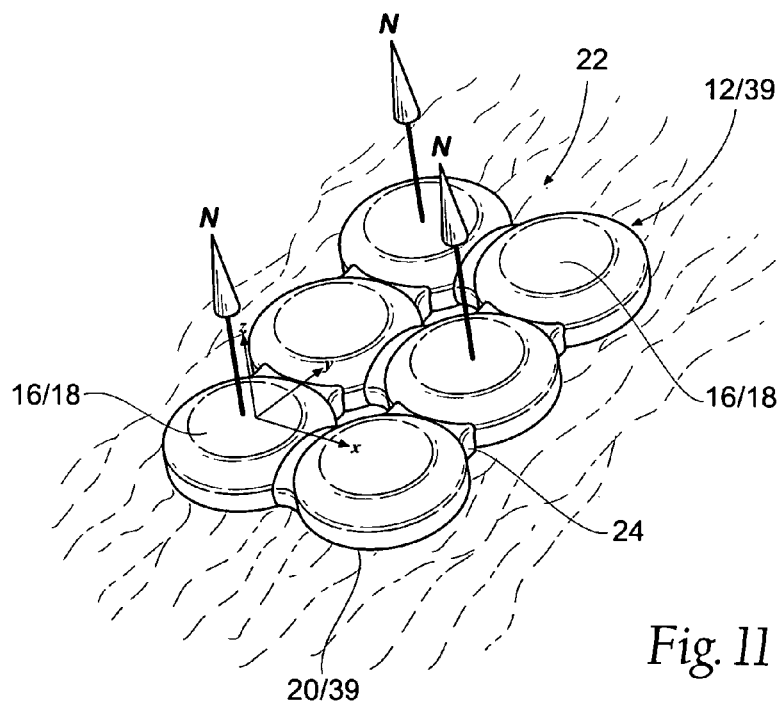
FIG. 11 is a perspective view of an array of ferromagnetic materials in a carrier that is sized and configured for implantation as part of the magnetic force system shown in FIGS. 4A to 4D, or 5A or 5B, or 6A or 6B.

Alternatively, a plurality of permanent magnetic material 16 or 18 can be positioned for placement as an array 22 carried as a unit on a support carrier 24, or otherwise directly linked together, as shown in FIG. 11. The carrier 24 can comprise, for example, a woven, formed, or molded structure made, e.g., from a polymer or fiber or fabric or non-ferrous metallic material. Like the magnetic materials 16/18 themselves, the arrays 22 can be variously shaped, sized, and configured for implantation in the intended tissue region (for the first structure 12) or for placement in association with external or internal tissue (for the second structure 14).

In the arrangement shown in FIG. 11, the magnetic materials 16/18 are placed on the carrier 24 with the N and S-poles facing generally in the same direction. In FIG. 11, the N-pole orientation is shown by the arrows, and the S-pole is therefore oriented in an opposite direction. In this way, an array 22 of like permanent magnets 16/18 having the relatively similar magnetic orientation (i.e., polarity) can be assembled for orientation as a unit on the carrier 24.

With respect to the first structure 12, a plurality of permanent magnetic materials 16 (or un-magnetized materials that are attracted to a magnetic material) can be incorporated within a flexible or compliant array 22 and carried as a unit on a support carrier 24 (as shown in FIG. 11) for implantation in tissue. With respect to the second structure 14 (the arrangements shown in FIG. 7A to 7C; FIGS. 8A and 8B; and FIGS. 9A to 9E), a plurality of permanent magnetic materials 18 can be incorporated in a more rigid array 26 carried as a unit on a support carrier 28. The support carrier 28 can be individually associated with headgear to stabilize its placement on or under the chin (FIGS. 7A to 7C), with a neck piece to stabilize its placement about a neck (FIGS. 8A and 8B), or with a mouthpiece to stabilize its placement within an oral cavity (FIGS. 9A to 9E). Like the magnetic materials 16/18 themselves, the array 26 can be variously shaped, sized, and configured.

In either arrangement (individually as shown in FIG. 10 or on an array as shown in FIG. 11), the magnetic material(s) 16 or 18 is/are desirably coated, plated, encapsulated, or deposited prior to placement in or on tissue, or placement in the respective stabilization device (headgear, neck piece, or mouthpiece) with a selected protective material 20 or 30, respectively. The protective material 20/30 is selected to provide a corrosion resistant and biocompatible interface, to prevent interaction between the magnetic material 16/18 and tissues or fluids of the body. The protective material 20/30 is also desirably selected to form a durable tissue interface, to provide longevity to the system component, and thereby provide resistance to structural fatigue and/or failure.

Selected to provide these desired physical and physiologic benefits, the protective material 20 and its application to the material 16 is also desirably selected to avoid imparting added stiffness to the structure 12 itself, to complement its preferred placement by implantation in tissue. However, with respect to the structure 14 (which desirably is not intended to be implanted), the protective material 30 used on material 18 can be and is desirably selected so that it will add stiffness to structure 14, so as to maximize the attraction between a relatively flexible structure 12 and a relatively immobile and less flexible structure 14. The more efficient the attraction between materials 18 and 16 is, the smaller the size of ferromagnetic materials 16 and 18, and thus the lighter and more comfortable the structures 12 and 14, can be.

The protective material 20/30 can be selected among various types of materials known to provide the desired biocompatibility, resistance to corrosion, and durability. For example, the protective material 20/30 can comprise titanium or other metal material plated, deposited, or otherwise coated upon the magnetic material 16/18. As another example, the protective material 20/30 can comprise a parylene coating. As other examples, the protective material 20/30 can comprise a silicone polymer, a non-toxic epoxy, a medical grade polyurethane, or a U.V. curable medical acrylic co-polymer. The protective material 20/30 may also incorporate anticoagulants and/or antibiotics and/or tissue in-growth promoters.

D. Representative Systems of Magnetic Structures

1. The Tongue System

Figure 12A:
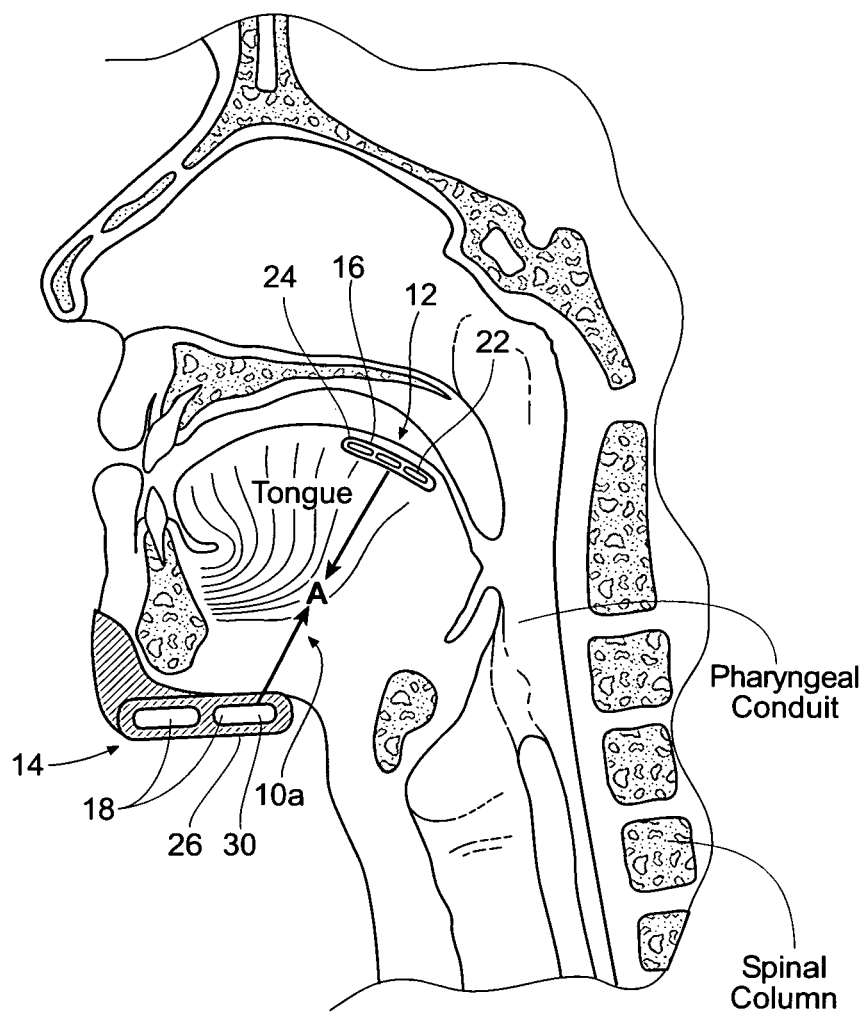
FIG. 12A is an anatomic side section view of the upper airway of a human, showing the nasal and oral cavities, tongue, hard palate, soft palate, oral pharynx, chin and neck, and further showing a representative magnetic force system of a type shown in FIG. 4A or 4C comprising a ferromagnetic structure implanted in a region of a tongue that interacts with a magnetic structure carried outside an airway (e.g., on a chin and/or jaw), to resist occurrence of the tissue condition shown in FIG. 3, involving the collapse of a tongue against the pharyngeal wall.

FIG. 12A shows a representative Tongue System 10a of the type shown in FIG. 4A. The system 10a comprises the ferromagnetic materials 16 and 18 arranged in a relatively similar, attracting orientation, as previously described. In FIG. 12A, the Tongue System 10a includes a first magnetic implant 12 comprising a first magnetic array 22 of a type shown in FIG. 11 sized and configured for implantation in the tongue. The Tongue System 10a also includes a second magnetic component 14 comprising a second magnetic array 26 also of a type shown in FIG. 11, but further incorporated into an under-the-chin orientation of a type shown in FIG. 7C.

Figure 12B:
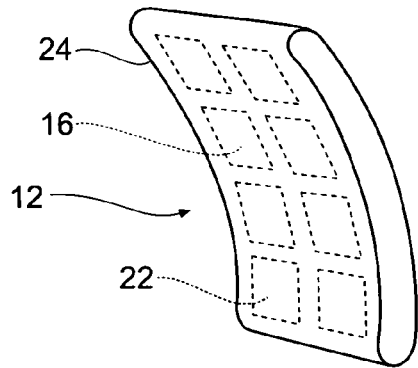
FIG. 12B is a perspective view of a ferromagnetic structure sized and configured to be implanted in a region of a tongue and forming a part of the system shown in FIG. 12A.

As shown in FIG. 12B, the array 22 of the first structure 12 comprises a carrier 24, on which the array 22 of ferromagnetic material(s) 16 (desirably comprising one or more permanent magnets) is arranged. As FIGS. 12A and 12B show, the carrier 24 is shaped along a longitudinal axis to have a length that is longer than its width. The longitudinally-shaped array 22 is sized and configured to be implanted along the anterior-to-posterior axis of the tongue and the airway, respectively. As shown in FIGS. 12A and 12B, the longitudinal axis of the array 22 extends along the raphé of the tongue.

Figure 12C:
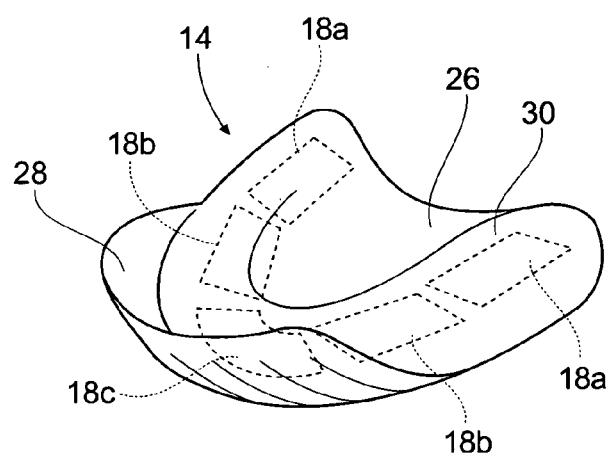
FIGS. 12C and 12D are, respectively, a perspective view and a side view of a magnetic structure sized and configured to be worn outside an airway (e.g., on a chin and/or jaw) and forming a part of the system shown in FIG. 12A.

As shown in FIG. 12C, the array 26 of the second structure 14 comprises a carrier 28, on which the array 26 of magnetic materials 18 (also permanent magnets) is arranged. The carrier 28 comprises the chin cup shown in FIG. 7C. In FIG. 12C, the array 26 is horseshoe-shaped (although many other arrangements are envisioned). The horseshoe-shaped array 26 is placed under the chin and lower jaw. It can be appreciated that a relatively similar or the same orientation of the magnetic materials 18 can be achieved by placing the array 26 in association with a neck piece (as shown in FIGS. 8A and 8B) or by placing the array in association with a mouthpiece worn within the oral cavity (as shown in FIGS. 9A to 9E).

Figure 12D:
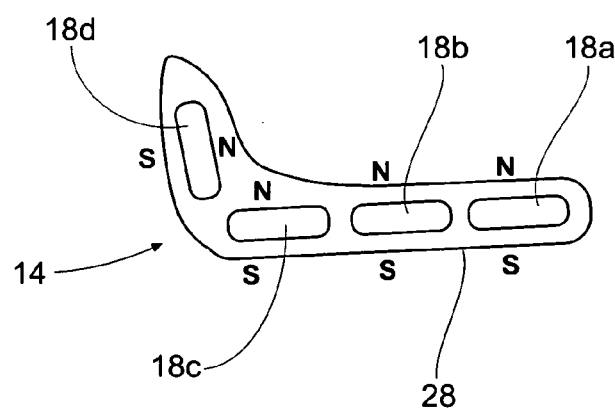

As shown in FIG. 12C, the horseshoe-shaped array of magnetic materials 18 follows the entire curved anatomy of the oral cavity from posterior to anterior. The array comprises posterior magnetic regions 18a (located on opposite sides of the tongue), an anterior magnetic region 18c (located along the curved anterior region of the oral cavity), and a middle magnetic regions 18b (located between the anterior and posterior regions of the oral cavity on opposite sides of the tongue). FIG. 12D shows an alternative embodiment to the horseshoe-shaped array. In this embodiment the magnetic materials 18 are placed both under the chin 18a, 18b, and 18c, and adjacent to the chin 18d.

Figure 12E:
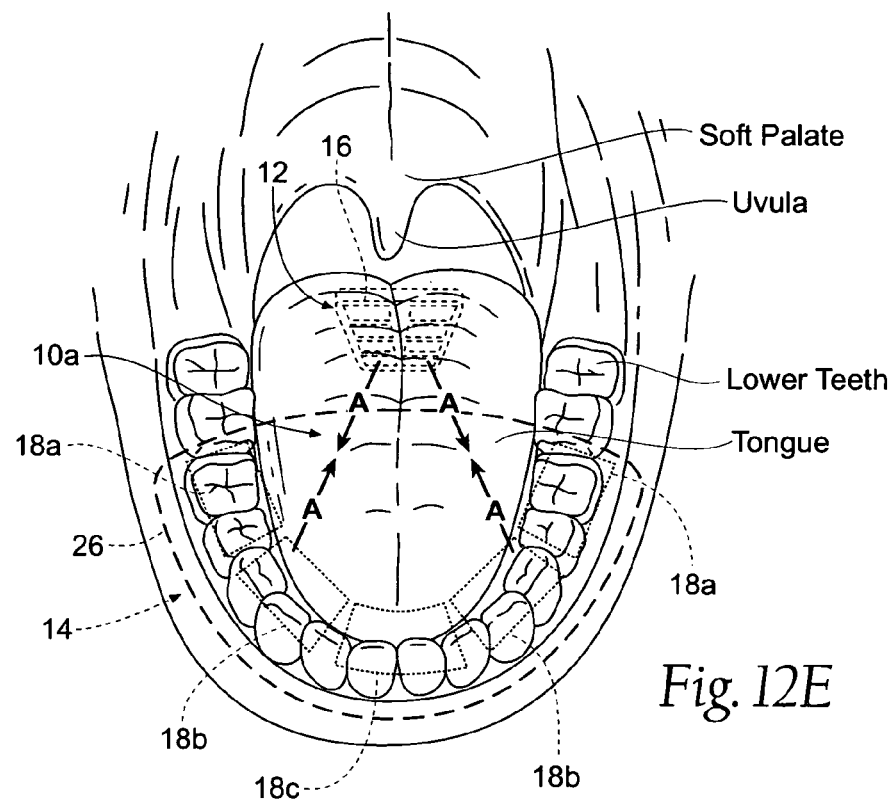
FIG. 12E is an anatomical anterior view of the oral cavity, showing the tongue and the hard and soft palates, and further showing the magnetic force system as shown in FIG. 12A, in which the ferromagnetic structure in the tongue extends generally symmetrically across the centerline of the tongue and the magnetic structure worn on the chin and/or jaw includes magnets on both lateral sides of the oral cavity, and further showing in this arrangement the magnetic attracting forces that resist occurrence of the tissue condition shown in FIG. 3, involving the collapse of a tongue against the pharyngeal wall.

When implanted, as FIG. 12E shows, poles of the magnetic material 16 of the first implant 12 are oriented to generally align with the opposite poles of the magnetic material 18 of the external component 14 across the airway, that is, either N-S or S-N-poles are generally aligned across the lower jaw or across tongue tissue, in the case of the mouthpiece array. As a result the magnetic external component 14 interacts by attracting the magnetic tongue implant 12 (as indicated by the facing arrows A in FIG. 12E). Due to the attracting forces A between implant 12 and structure 14, the tongue tissue cannot collapse against the pharyngeal conduit during sleep and thus the airway remains patent. However, when an apnea patient is awake, the forces may be overcome by swallowing, speech, coughing, sneezing, etc. Alternatively, the external magnets 18 can be positioned and worn only for purposes of sleeping allowing for higher, more therapeutic forces during sleep which are easily removed to allow normal swallowing and speech function during daytime hours.

Figure 12F:
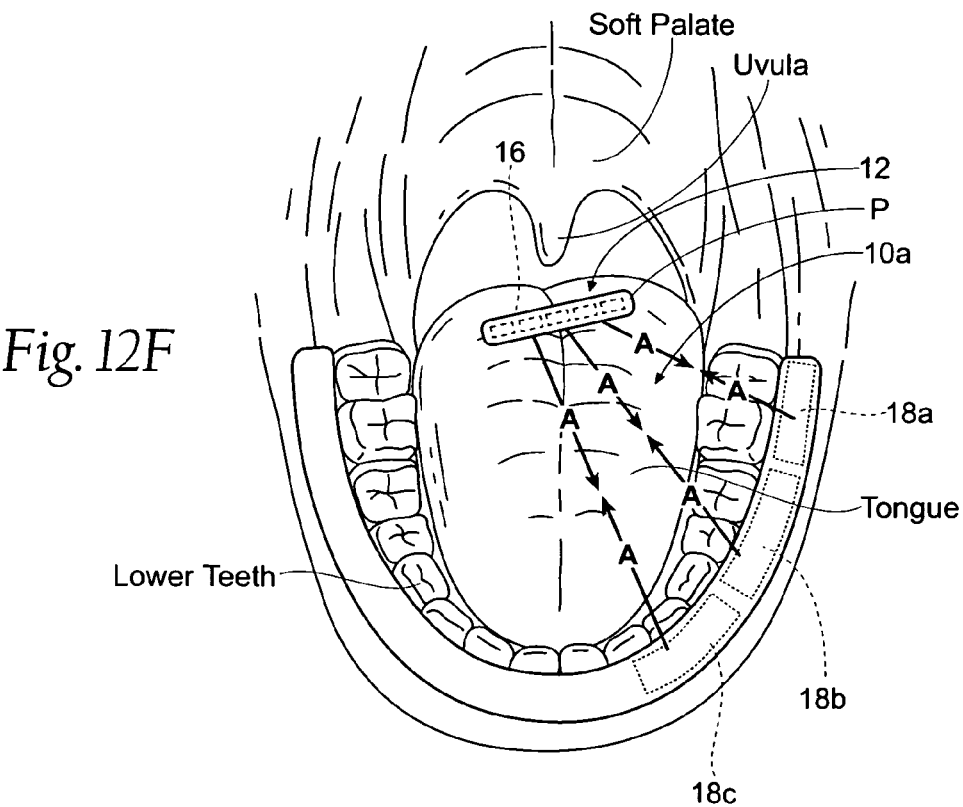
FIG. 12F is an anatomical anterior view of the oral cavity, showing the tongue and the hard and soft palates, and further showing the magnetic force system as shown in FIG. 12A, in which the ferromagnetic structure in the tongue extends generally symmetrically across the centerline of the tongue and the magnetic structure worn on the chin and/or jaw includes magnets only on one lateral side of the oral cavity, and further showing in this arrangement the magnetic attracting forces that resist occurrence of the tissue condition shown in FIG. 3, involving the collapse of a tongue against the pharyngeal wall.

In an alternative arrangement, as shown in FIG. 12F, the array of magnetic materials 18 does not symmetrically follow the entire curved anatomy of the oral cavity from posterior to anterior. Instead, the array comprises a posterior magnetic region 18a, an anterior magnetic region 18c, and a middle magnetic region 18b asymmetrically only along one side of the tongue. In this arrangement, in response to the attracting magnetic forces between the implant 12 implanted in the tongue and the single sided magnetic structure 14 carried by the chin, neck, or teeth, the airway on the side of the tongue farthest from magnets 18 will open up. That side of the tongue will no longer collapse against the pharyngeal wall and apneic episodes will be prevented.

Figure 12G:
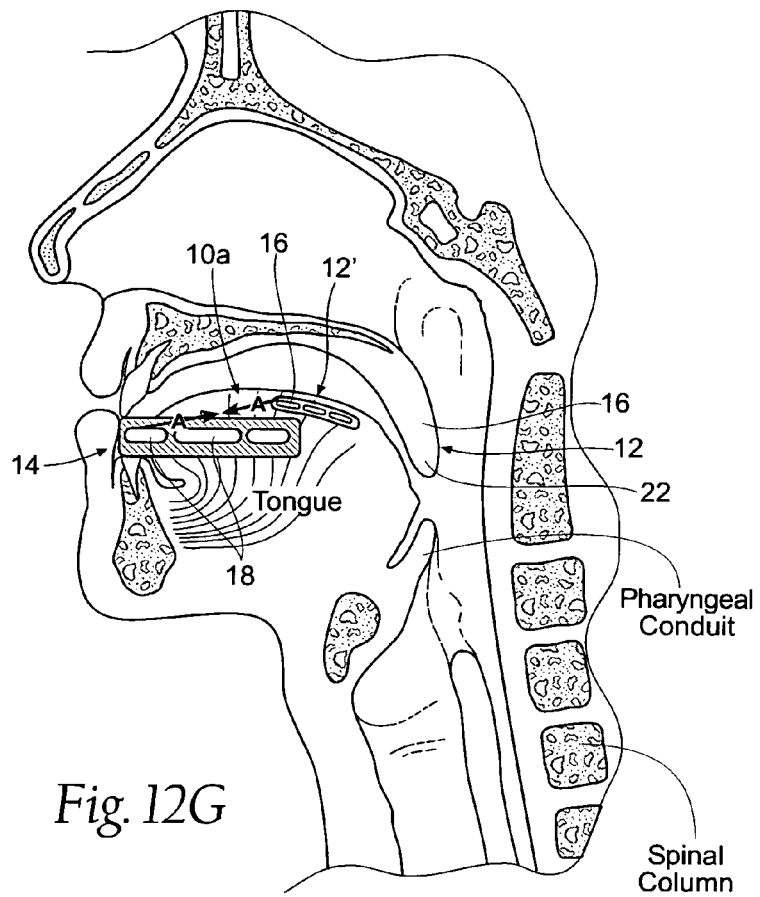
FIG. 12G is an anatomic side section view of the upper airway of a human, showing the nasal and oral cavities, tongue, hard palate, soft palate, oral pharynx, chin and neck, and further showing a representative magnetic force system of a type shown in FIG. 4B or 4D comprising a ferromagnetic structure implanted in a region of a tongue that interacts with a magnetic structure carried inside an airway (e.g., within an oral cavity), to resist occurrence of the tissue condition shown in FIG. 3, involving the collapse of a tongue against the pharyngeal wall.
Figure 12H:
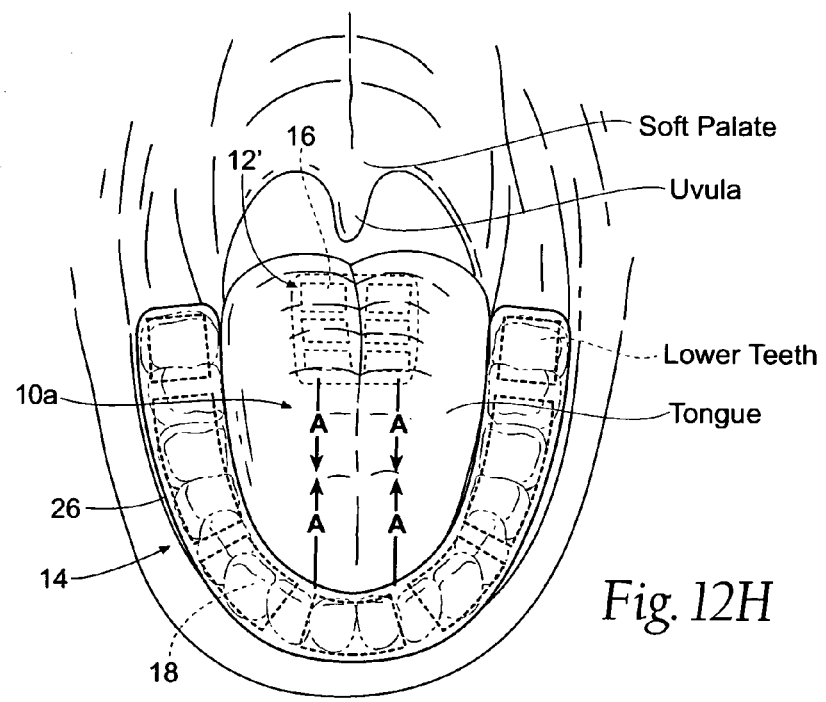
FIG. 12H is an anatomical anterior view of the oral cavity, showing the tongue and the hard and soft palates, and further showing the magnetic force system as shown in FIG. 12G, in which the ferromagnetic structure in the tongue extends generally symmetrically across the centerline of the tongue and the magnetic structure worn within the oral cavity includes magnets on both lateral sides of the oral cavity, and further showing in this arrangement the magnetic attracting forces that resist occurrence of the tissue condition shown in FIG. 3, involving the collapse of a tongue against the pharyngeal wall.

In yet another alternative arrangement, as shown in FIGS. 12G and 12H, the tongue implant 12' is aligned in parallel arrangement to the mouthpiece structure/external component 14. The magnetic attracting force between the tongue implant 12' and the external component pushes the tongue in an anterior direction. This particular embodiment may be able to generate more force than previous embodiments due to the shorter distance between the tongue implant and the mouthpiece structure.

2. The Soft Palate System

Figure 13A:
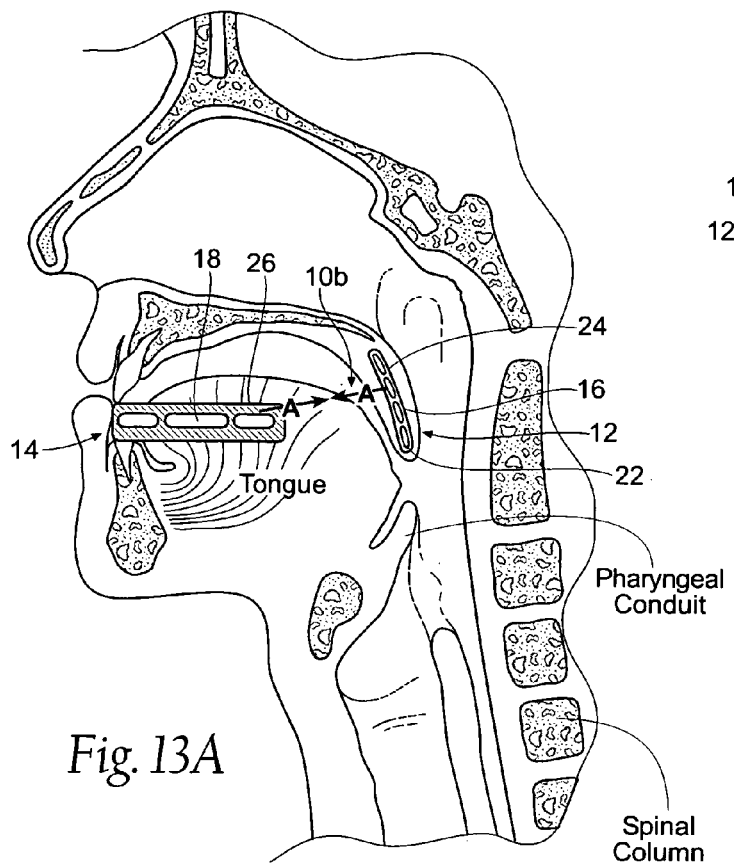
FIG. 13A is an anatomic side section view of the upper airway of a human, showing the nasal and oral cavities, tongue, hard palate, soft palate, oral pharynx, chin and neck, and further showing a representative magnetic force system of a type shown in FIG. 4B or 4D comprising a ferromagnetic structure implanted in a region of a tongue that interacts with a magnetic structure carried inside an airway (e.g., in an oral cavity), to resist occurrence of the tissue condition shown in FIG. 3, involving the collapse of a tongue against the pharyngeal wall.

FIG. 13A shows a representative Soft Palate System 10b of the type shown in FIG. 5B. The system 10b comprises the ferromagnetic materials 16 and 18 arranged in an attracting orientation, as previously described. In FIG. 13A, the Soft Palate System 10b includes a first magnetic implant 12 comprising a first magnetic array 22 of a type shown in FIG. 11 sized and configured for implantation in the soft palate. The Soft Palate System 10b also includes a second magnetic component 14 comprising a second magnetic array 26 also of a type shown in FIG. 11, but further incorporated into a mouthpiece orientation (placed outside the lower teeth) of a type shown in FIG. 9B.

Figure 13B:
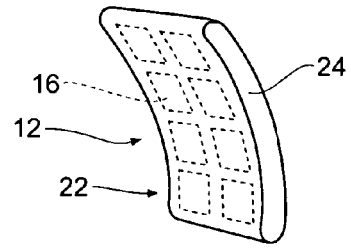
FIG. 13B is a perspective view of a ferromagnetic structure sized and configured to be implanted in a region of a tongue and forming a part of the system shown in FIG. 13A.

As shown in FIG. 13B, the array 22 of the first structure 12 comprises a carrier 24, on which the array 22 of ferromagnetic material(s) 16 (desirably comprising one or more permanent magnets) is arranged. As FIGS. 13A and 13B show, the carrier 24 is shaped along a longitudinal axis. The longitudinally-shaped array 22 is sized and configured to be implanted along the anterior-to-posterior axis of the soft palate and the airway, respectively. As shown in FIGS. 13A and 13B, the longitudinal axis of array 22 extends along the midline of the soft palate or uvula.

Figure 13C:
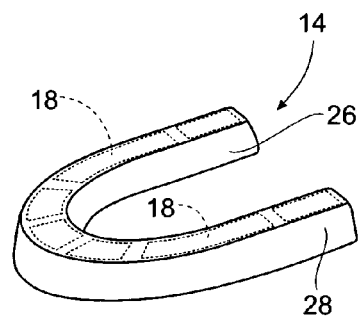
FIG. 13C is a perspective view of a magnetic structure sized and configured to be worn within an airway, e.g., on teeth within an oral cavity, and forming a part of the system shown in FIG. 13A.

As shown in FIG. 13C, the array 26 of the second structure 14 comprises a carrier 28, on which the array 26 of magnetic materials 18 (also permanent magnets) is arranged. The carrier 28 comprises the mouthpiece shown in FIG. 9B. In FIG. 13C, the array 26 is horseshoe-shaped to conform to the profile of the lower teeth. It can be appreciated that the same orientation of the magnetic materials 18 can be achieved and stabilized by placing the array 26 in association with a headgear (as shown in FIGS. 7A and 7B), chin cup (as shown in FIG. 7C), or neck piece (as shown in FIGS. 8A and 8B) or by placing the array in association with other mouthpieces worn within the oral cavity (as shown in FIGS. 9A and 9C to 9E).

Figure 13D:
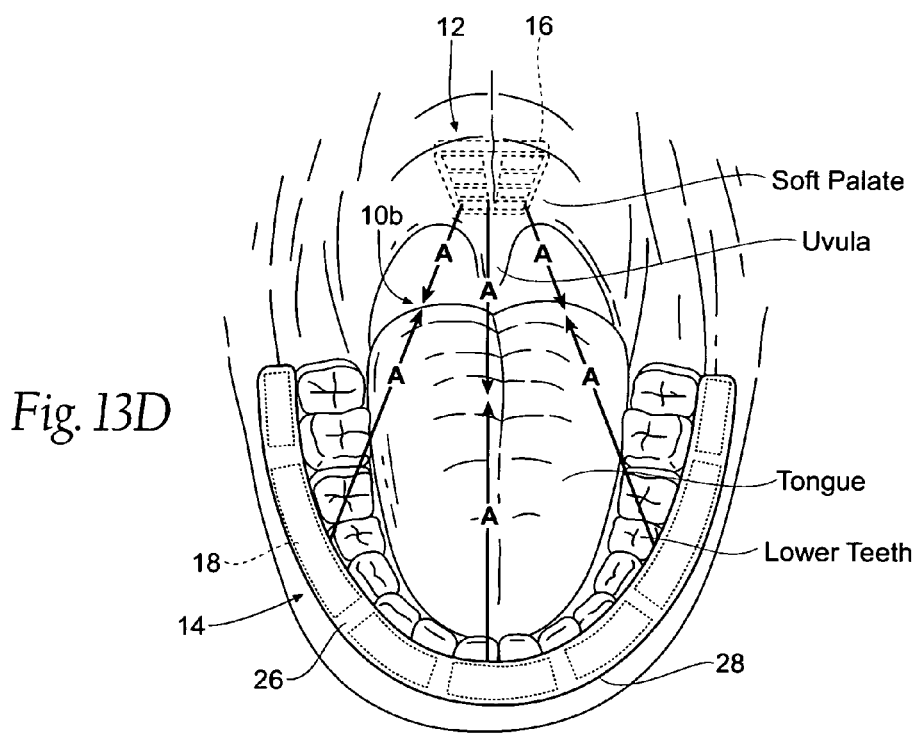
FIG. 13D is an anatomical anterior view of the oral cavity, showing the tongue and the hard and soft palates, and further showing the magnetic force system as shown in FIG. 13A, in which the ferromagnetic structure in the tongue extends generally symmetrically across the centerline of the tongue and the magnetic structure worn on teeth within an oral cavity includes magnets on both lateral sides of the oral cavity, and further showing in this arrangement the magnetic attracting forces that resist occurrence of the tissue condition shown in FIG. 3, involving the collapse of a tongue against the pharyngeal wall.

When implanted, as FIG. 13D shows, poles of the magnetic material 16 of the first implant 12 are oriented to generally align with the opposite poles of the magnetic material 18 of the external component 14 across the airway, that is, either N-S or S-N-poles are generally aligned across tongue tissue or across the lower jaw, in the case of a chin cup or neck piece array. As a result the magnetic external component 14 interacts by attracting the magnetic soft palate implant 12 (as indicated by the attracting arrows A in FIG. 13D).

Due to the attracting force between implant 12 and structure 14, the soft palate does not collapse against the pharyngeal conduit during sleep and thus the airway remains patent. However, when an apnea patient is awake, the forces may be overcome by swallowing, speech, coughing, sneezing, etc. Alternatively, the oral cavity magnets 18 can be positioned and worn only for purposes of sleeping, allowing for higher, more therapeutic forces during sleep which are easily removed to allow normal swallowing and speech function during daytime hours.

3. The Combined System

FIG. 14A shows a representative Combined System 10c of the type shown in FIG. 6B. The system 10c comprises the ferromagnetic materials 16 and 18 arranged in an attracting orientation, as previously described. In FIG. 14A, the Combined System 10c includes a pair of first ferromagnetic implants 12a and 12b. Each implant 12a and 12b comprising a ferromagnetic magnetic array 22 of a type shown in FIG. 11 sized and configured for implantation, respectively, in the tongue and the soft palate. The Combined System 10c also includes a second magnetic component 14 comprising a second magnetic array 26 also of a type shown in FIG. 11, but further incorporated into a mouthpiece orientation (placed outside the lower teeth) of a type shown in FIG. 9B.

As shown in FIGS. 14A and 14B, the arrays 22 of the first structures 12a and 12b each comprises a carrier 24, on which the respective array 22 of ferromagnetic materials 16 (desirably comprising one or more ferromagnets) is arranged. As FIGS. 14A and 14B show, the carrier 24 of each structure 12a and 12b is shaped along a longitudinal axis. The longitudinally-shaped array 22 of the structure 12b is sized and configured to be implanted along the anterior-to-posterior axis of the tongue. The longitudinally-shaped array 22 of the structure 12a is sized and configured to be implanted along the anterior-to-posterior axis of the soft palate.

As shown in FIG. 14C, the array 26 of the second structure 14 comprises a carrier 28, on which the array 26 of magnetic materials 18 (also permanent magnets) is arranged. The carrier 28 comprises the mouthpiece shown in FIG. 9B. In FIG. 14C, the array 26 is horseshoe-shaped to conform to the profile of the lower teeth. It can be appreciated that the same orientation of the magnetic materials 18 can be achieved and stabilized by placing the array 26 in association with a headgear (as shown in FIGS. 7A and 7B), chin cup (as shown in FIG. 7C), or neck piece (as shown in FIGS. 8A and 8B) or by placing the array in association with other mouthpieces worn within the oral cavity (as shown in FIGS. 9A and 9C to 9E).

When implanted, as FIG. 14D shows, the magnetic material 16 of both implants 12a and 12b are generally attracted to the magnetic material 18 of the external component 14 (as indicated by the attracting arrows A in FIG. 14D). Due to the attracting forces A between each of the implants 12a and 12b and the structure 14, the tongue and the soft palate resist collapse against the pharyngeal conduit during sleep and thus the airway remains patent. However, when an apnea patient is awake, the forces may be overcome by swallowing, speech, coughing, sneezing, etc. Alternatively, the oral cavity magnets 18 can be positioned and worn only for purposes of sleeping allowing for higher, more therapeutic forces during sleep which are easily removed to allow normal swallowing and speech function during daytime hours.

The various magnetic force systems 10a, 10b, and 10c as described provide an elegant, cost-effective treatment of sleep apnea. Placed in or on tissue in the tongue, soft palate, or uvula, the ferromagnetic structure 12, along with its companion ferromagnetic structure 14, is well tolerated and significantly more comfortable and user friendly than the equipment of CPAP and is likely more desirable than other highly intrusive surgical treatment options. The magnetic systems 10a, 10b, and 10c offer a sophisticated, yet easy to use design, which can be shaped, configured, and magnetically titrated to meet patients' individual needs, based upon specific anatomic and physiologic requirements, as will be described in greater detail later.

III. Moderating the Force-Distance Relationship Forces in Dynamic Tissue Regions A. Generally In the systems 10a, 10b, and 10c shown in FIGS. 12A to 12E; 13A to 13D; and 14A to 14D, the magnetic components 12 and 14 are desirably aligned vertically across the lower jaw or across tongue tissue from each other to create an attracting magnetic force field. In reality, there is rarely a theoretically "perfect" magnetic alignment between the magnetic materials 16 and 18. This is due to the dynamic nature of the tongue and soft palate in the airway. The distance and orientation between the tongue and soft palate, and between each of the tongue and soft palate and the lower jaw varies due to patient-to-patient anatomical variability, as well as the tongue's and soft palate's constant movement during sleep and waking hours. There is rarely a geometrically "perfect," parallel relationship between these tissue structures within the airway. Further, when the tongue or soft palate moves laterally, posteriorly, anteriorly, cranially, caudally, in a rolling manner, or any combinations thereof during sleep, the movement can significantly alter the orientation and alignment between the attracting magnetic materials 16 and 18 from one moment to another.

Variations in the force across an implant (or a magnet, or any other object) can manifest as torques, and are present in any magnetic system that is not in perfect alignment. Torque is present in all systems, whether attracting or repelling; when magnets are not in "perfect" alignment, where there is increased misalignment by angle or position, the torque will tend to correct the alignment of the magnets; i.e., they will rotate toward an alignment that maximizes the attracting force. The magnets want to be perfectly aligned in the highest state of attraction possible, in other words to be best aligned with a N-pole facing a S-pole.

Magnetic structures placed in or on mobile anatomic structures in the airway are seldom, if ever, orientated in a way that permits theoretically "perfect" or ideal alignment of N-S or S-N attracting poles. The alignment of the attracting magnetic materials is rarely theoretically "perfect" or ideal, and it is subject to continuous change. It is by understanding and controlling the torque inherent in magnetic systems, that the tongue can be effectively manipulated for the therapeutic purposes disclosed herein.

B. Design Considerations

Any attracting magnetic system involving the tongue and/or soft palate desirably takes into account and balances at least three considerations. One consideration is anatomic—(i) the varying distances and the lack of perfect parallel alignment between the tongue and the soft palate and between each of the tongue and the soft palate and the lower jaw, due to individual upper respiratory anatomy and the natural movement of the tongue relative to the soft palate and relative movement of either the tongue or soft palate to the lower jaw. The other two considerations are physical—(ii) the ability to place implants in the most desired orientation to one another; and (iii) the distance between attracting magnets and the resulting force must also be taken into account, i.e. systems which keep distance relatively short and provide for a tether to apply force at an off-set location.

A given attracting tongue or soft palate structure should desirably be maintained in a position of maximal attraction as other structures, such as the tongue, soft palate, or uvula, move in relation to the lower jaw. For example, it should be recognized that during sleep, the tongue will undergo a wide variety of motions and changes of angular orientation to the lower jaw.

A given tongue or soft palate structure desirably includes features for maintaining the implant in its close to maximal attracting state at all the angular alignments and varying distances normally and abnormally encountered with respect to the lower jaw, but should still allow for performance of natural bodily functions during sleep, e.g. swallowing.

C. Titrated Magnetic Arrays

Magnetic force is roughly inversely proportional to the square of the distance between the magnetic structures. Magnetic force is therefore very sensitive to distance. A small increase in distance between attracting magnetic structures can therefore lead to a dramatic decrease in magnetic force between them. The slope of Curve SM in FIG. 15 demonstrates how the magnitude of a magnetic force field (y-axis) between two single magnet structures (as shown in FIG. 10) decreases significantly with relatively small increases in distance between them (x-axis) due to the inverse-square relationship.

The range of distances between magnetic structures 12 and 14 in the systems 10a, 10b, and 10c during normal anatomic functions of the tongue and/or soft palate will be in shorthand called the "working range." It is believed that, in the context of the systems 10a, 10b, and 10c, the working range lies in a range of about 3 cm to 4 cm. For a given system 10a, 10b, or 10c, the magnetic structures 12 and 14 are desirably sized and configured so that the magnitude and flux distribution of the magnetic force field is designed or selected so that variations in magnetic force due to variations in distance between the structures 12 and 14 are moderated, at least within the boundaries of the working range. At least within the boundaries of the working range, the titrated magnetic force field provides a variation of magnetic field force with distance that presents a slope having a magnitude less than the slope of curve SM in FIG. 15. Again, within the boundaries of the working range, the slope of the magnetic force field diminishes substantially, thereby reducing the sensitivity of the force-distance relationship. In the systems 10a, 10b, and 10c shown in FIGS. 12A to 12D; 13A to 13D; and 14A to 14D, the magnetic structure 14 is desirably sized and configured to provide one or more field direction(s) such that the magnetic structure 14 maintains a relatively constant magnetic field and attracting force with the internal structure 12 despite relative movement of the tongue, soft palate, or uvula in the normal performance of bodily functions.

During the normal performance of bodily functions, the separation between the centers of mass of the structures 12 and 14 will vary within the working range between a distance $\delta_{FAR}$ (expressed in units of centimeters) where the centers of mass of the structures 12 and 14 are placed farthest apart and a distance $\delta_{NEAR}$ (expressed in units of centimeters) where the centers of mass of the structures 12 and 14 are placed closest together. At the distances $\delta_{FAR}$ and $\delta_{NEAR}$ there will be a resulting magnetic force, respectively $F_{FAR}$ (expressed in units of grams) and $F_{NEAR}$ (expressed in units of grams) of the magnetic force system, which will vary roughly inversely proportional to the square of the respective far and near distances of the working range, or $(1/\delta_{FAR}^2)$ and $(1/\delta_{NEAR}^2)$, respectively. The magnetic structures 12 and 14 are desirably mutually sized and configured so that variations in magnetic force due to various in distance between the magnetic structures 12 and 14 within the working range maintain a relationship, as follows:

$$(F_{NEAR}/F_{FAR}) \leq (\delta_{FAR}^2/\delta_{NEAR}^2)$$

In this way, the magnetic structure 14 maintains a relatively constant magnetic field and attracting force with the internal structure 12 despite relative movement of the tongue, soft palate, or uvula within the working range in the normal performance of bodily functions.

To achieve this objective, the systems 10a, 10b, and 10c desirably include magnetic structures 12 and 14 comprising arrays of magnets like that shown in FIG. 11. Arrays of magnetic materials 16 and 18 provide a more uniform distribution of magnetic field and attracting force with the internal structure 12 within the desired working range. Arrays of magnetic materials 16 and 18 also make it possible to control the magnitude and distribution of the magnetic field between the structures 16 and 18 to moderate the sensitivity of the force-distance relationship within the working range. Larger, smaller, or different arrays of magnetic materials 16 and 18 can be used to titrate the uniform attracting force with internal structure 12 and external magnet 14.

Figure 16A:
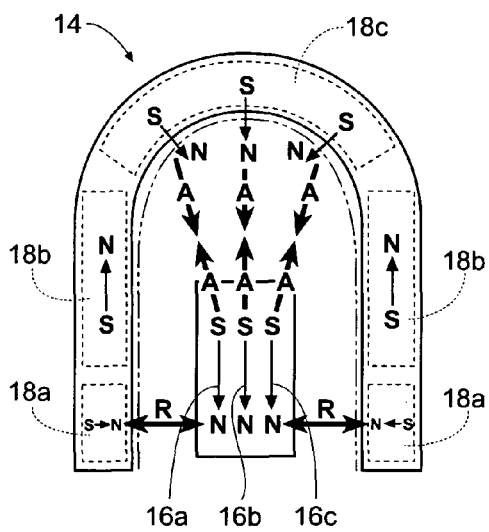
FIGS. 16A and 17A are diagrammatic views of a titrated magnetic structure carried on a chin or jaw outside an airway or on teeth in an airway that interacts with a ferromagnetic structure implanted in a tongue or a soft palate/uvula, also showing in this arrangement how the magnetic attracting forces have been moderated by the titration to the sensitivity of the force-distance relationship with a prescribed working space defined during normal anatomic functions of a tongue and soft palate/uvula.
Figure 16B:
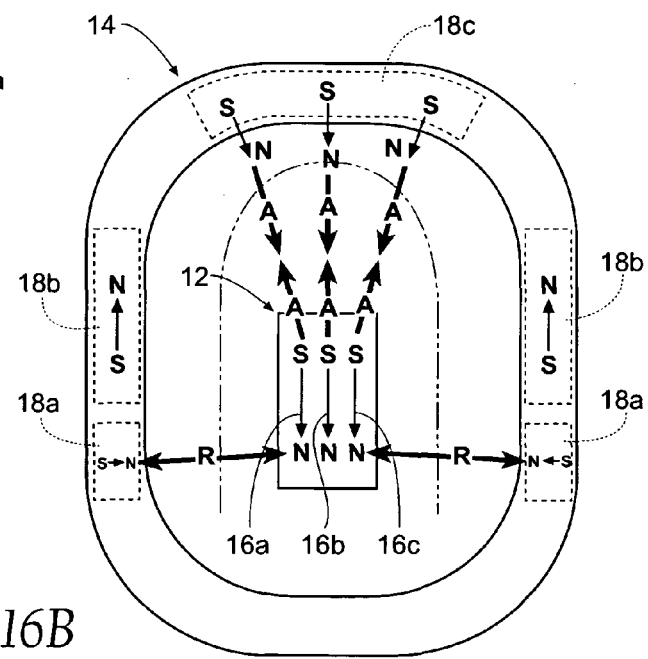
FIGS. 16B and 17B are diagrammatic views of a titrated magnetic structure worn about a neck outside an airway that interacts with a ferromagnetic structure implanted in a tongue or a soft palate/uvula, also showing in this arrangement how the magnetic attracting forces that have been moderated by the titration to the sensitivity of the force-distance relationship with a prescribed working space defined during normal anatomic functions of a tongue and soft palate/uvula.

For example, the magnetic structure 14 shown in FIGS. 16A and 16B includes an array of magnets comprising distinct spatial magnetic regions 18a, 18b, and 18c having different polarities. The magnetic regions 18a, 18b, and 18c are sized and configured for use in association with an implanted magnetic structure 12 to form a Tongue System 10a, or a Soft Palate System 10b, or a Combined System 10c. In FIGS. 16A and 16B the magnetic structure 12 also comprises an array of magnetic regions 16a, 16b, and 16c implanted in the tongue, or soft palate/uvula, or both the tongue and soft palate/uvula.

As shown in FIGS. 16A and 16B, the spatially distinct magnetic regions 16a, 16b, and 16c can each comprise a single magnet or an array of individual magnets of common polarity (as shown in FIG. 11) arranged on a carrier. The array of spatially distinct magnetic materials 16a, 16b, and 16c can be sized and configured to follow the curved anatomy of the oral cavity from posterior to anterior.

The structure 14 comprises posterior magnetic regions 18a (located on opposite sides of the tongue), an anterior magnetic region 18c (located along the curved anterior region of the oral cavity), and a middle magnetic region 18b (located between the anterior and posterior regions of the oral cavity on opposite sides of the tongue). The array of magnetic regions 18a, 18b, and 18c shown in FIG. 16A is sized and configured for particular use in a chin-mounted or mouth piece configuration, as previously discussed and as shown, respectively, in FIGS. 7A to 7C and FIGS. 9A to 9E. The array of magnetic regions 18a, 18b, and 18c shown in FIG. 16B is sized and configured for particular use in a neck piece configuration, as previously described and as shown in FIGS. 8A and 8B.

As shown in FIGS. 16A and 16B, the N-poles of the magnetic regions 18a, 18b, and 18c in the headgears, chin cup, mouth piece, or neck arrays are mutually oriented differently both with respect to each other and with respect to the S-poles of the magnetic materials 16 implanted in the airway in the tongue and/or soft palate. The mutually different orientations of the N-poles of the magnetic regions 18a, 18b, and 18c provide a titrated magnetic field force that moderates the sensitivity of force-to-distance relationship between the magnetic materials 16 and 18 in the working range.

More particularly, as FIGS. 16A and 16B show, the orientation of the N-poles of the spatially distinct magnetic regions 18a, 18b, and 18c varies from posterior to anterior with respect to the S-poles of the magnetic regions 16a, 16b, and 16c. As FIGS. 16A and 16B show, the anterior magnetic region 18c (spanning the front of the oral cavity) has a N-pole orientation directed toward the oral cavity, in a facing relationship with the S-poles of the magnet regions 16a, 16b, and 16c. As the region 18c curves to conform to the curved anatomy of the anterior oral cavity, the orientation of the N-poles of the magnetic region 18c likewise changes to always point inwards toward the S-poles of the magnetic regions 16a, 16b, and 16c. The N-S orientation between the anterior magnetic region 18c of the structure 14 and the anterior magnetic regions 16a, 16b, and 16c of the structure 12 generates an attracting magnetic field (attracting arrows A) in the anterior region of the oral cavity. The attracting magnetic field A resists posterior movement of the tongue and/or soft palate/uvula, which is a desired therapeutic objective.

The posterior magnetic regions 18a of the structure 14 (located on opposite sides of the tongue in the back of the oral cavity) have a N-pole orientation toward the oral cavity. The magnetic region 18a thereby presents N-poles oriented in a generally facing relationship with the N-poles of the magnet regions 16a, 16b, and 16c, which are located in the posterior of the tongue and/or soft palate/uvula. The N-N orientation between the posterior magnetic regions 18a of the structure 14 and the posterior magnetic regions 16a, 16b, and 16c of the structure 12 generates a repelling magnetic field (repelling arrows R) in the posterior region of the oral cavity. The fluxes of the arrays interact to create an anterior directed force, which is relatively stable where the implant is well-aligned in a medial-lateral direction.

In this arrangement, the middle magnet regions 18b of the structure 14 (between the posterior and anterior magnetic regions 18a and 18c on opposite sides of the tongue along the lateral sides of the oral cavity) have a N-pole orientation toward the anterior magnetic region 18c. Juxtaposed between the attracting magnetic field in the anterior region of the oral cavity and the repelling magnetic field in the posterior region of the oral cavity, the N-pole orientation of the middle magnetic region 18b's direct flux in the magnetic field between the anterior magnetic region 18c's (which attracts the tongue and/or soft palate/uvula at the anterior region of the oral cavity) and the posterior magnetic region 18a's (which repels the tongue and/or soft palate/uvula at the posterior region of the oral cavity), without imposing a significant destabilizing side-to-side attracting force on the tongue and/or soft palate. The magnetic regions 18a, 18b, and 18c have been sized and configured to create a relatively constant magnetic flux or a relatively constant magnetic flux gradient in the working range where the implant 12 is expected to be positioned.

Figure 17A:
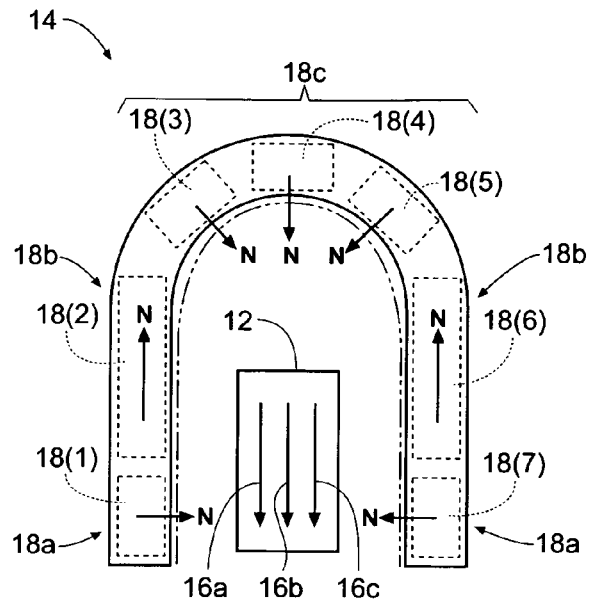
Figure 17B:
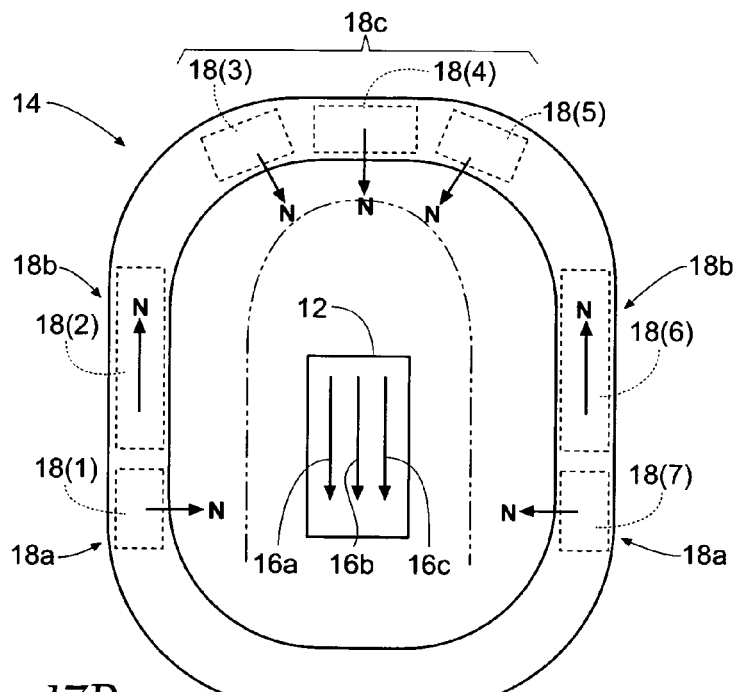

The magnetic regions 18a, 18b, and 18c shown in FIGS. 16A and 16B can be variously constructed. For example, FIGS. 17A and 17B are illustrative examples of magnetic arrays comprising seven separate permanent magnets 18(1) to 18(7), whose N-polarities have been labeled. FIG. 17A is directed to a chin-mounted or mouth piece structure, like FIG. 16A. FIG. 17B is directed to a neck-collar structure, like that in FIG. 16B.

Magnets 18(1) and 18(7) each comprise a posterior magnetic region 18a. Magnets 18(3), 18(4), and 18(5) collectively comprise the anterior magnetic region 18c. Magnets 18(2) and 18(6) each comprise a middle magnetic region 18b. As shown in FIGS. 17A and 17B, the magnetic fields can be manipulated by changing direction of the magnets themselves.

Figure 15:
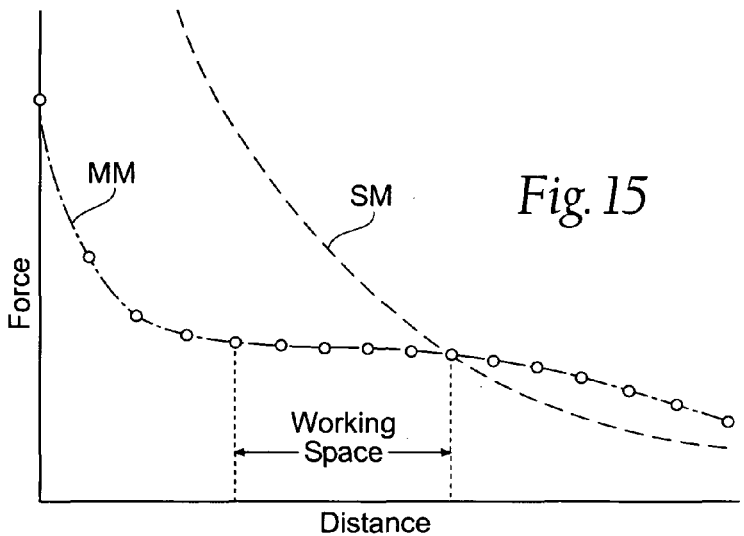
FIG. 15 is a graph showing how magnetic force is sensitive to distance (curve SM) and how titration of a magnetic force field (curve MM) can reduce with sensitivity of the force-distance relationship with a prescribed working space defined during normal anatomic functions of a tongue and soft palate/uvula.

FIG. 15 illustrates (Curve MM) the force versus distance relationship between arrays 12 and 14 as shown in FIGS. 16A/B and FIGS. 17A/B, as just described. The slope of Curve MM in FIG. 15 demonstrates how magnitude of a magnetic force field (y-axis) between the two arrays 12 and 14 (as shown in FIG. 16A/B or 17A/B) does not decrease significantly within the boundaries of the working range (x-axis). Curve MM further demonstrates that the slope diminishes substantially within the boundaries of the working range.

FIG. 18A is a diagrammatic representation of a finite element analysis showing the flux direction lines for the magnetic arrays of a type shown in FIGS. 16A/B and 17A/B. FIG. 18B is another diagrammatic representation of a finite element analysis showing distribution of the magnetic field force for these magnetic arrays 16a/16b/16c and 18(1) to 18(7). As seen in FIG. 18B, the arrays generate a titrated magnetic field F1/F2/F3 having a force that generates a relatively constant force F3 over a working range of 3 cm to 4 cm. This relatively constant magnetic field force F3 allows the structure 12 implanted in the tongue, soft palate, or uvula to vary in its position within the working range due to normal functions without significant loss of attracting magnetic force with respect to the structure 14.

D. Tethered Magnetic Structures

Figure 39A:
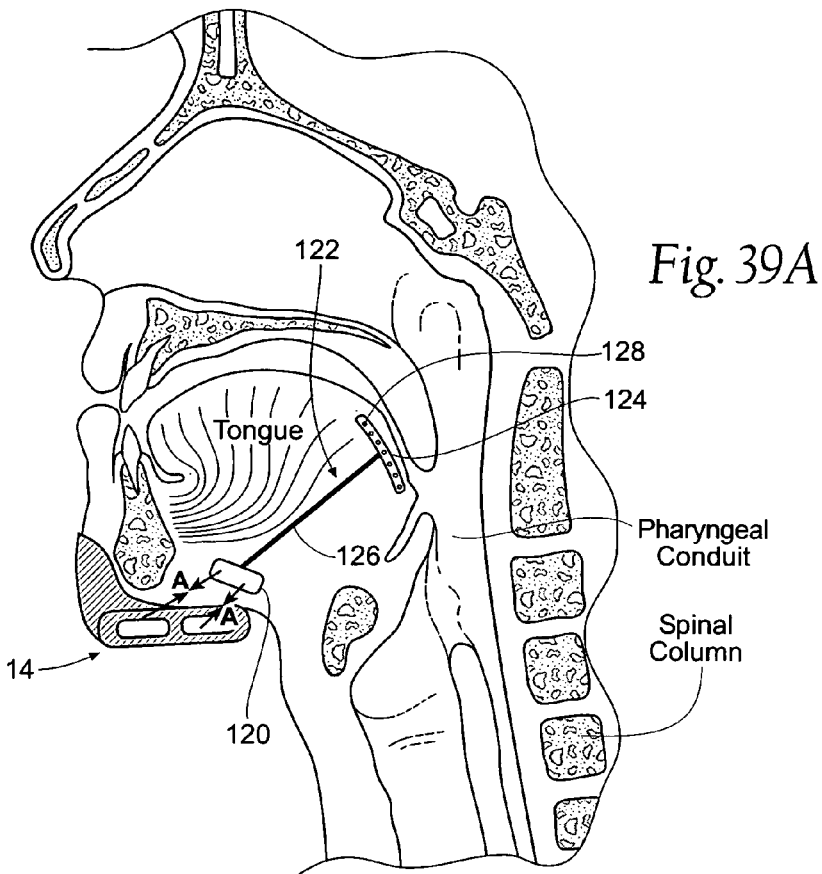
FIGS. 39A and 39B are anatomic side section views of the upper airway of a human, showing the nasal and oral cavities, tongue, hard palate, soft palate, oral pharynx, chin and neck, and further showing a representative magnetic force system of a type shown in FIG. 4C comprising a ferromagnetic structure implanted in a lower, inferior region of a tongue that interacts with a magnetic structure carried outside an airway (e.g., on a jaw), to resist occurrence of the tissue condition shown in FIG. 3, involving the collapse of a tongue against the pharyngeal wall, the ferromagnetic structure including (in FIG. 39A) a single tethered anchoring assembly and (in FIG. 39B) a multiple tether anchoring assembly to stabilize the ferromagnetic structure in close proximity to the external jaw-mounted magnetic structure.
Figure 39B:
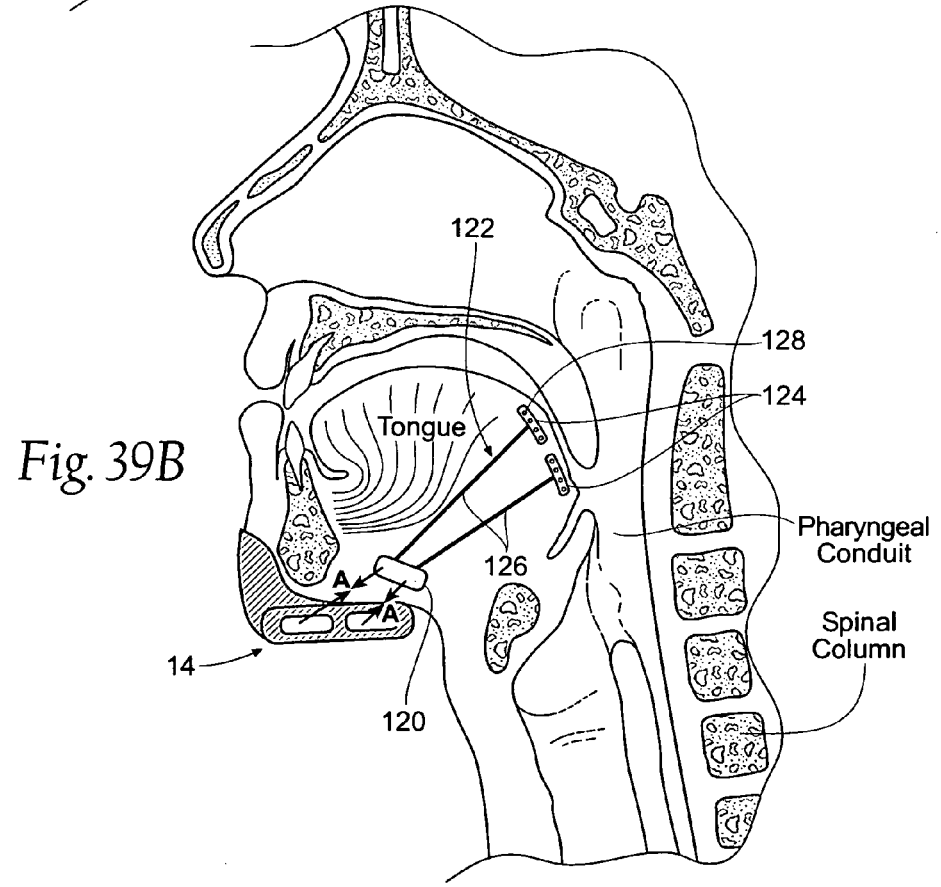
Figure 39C:
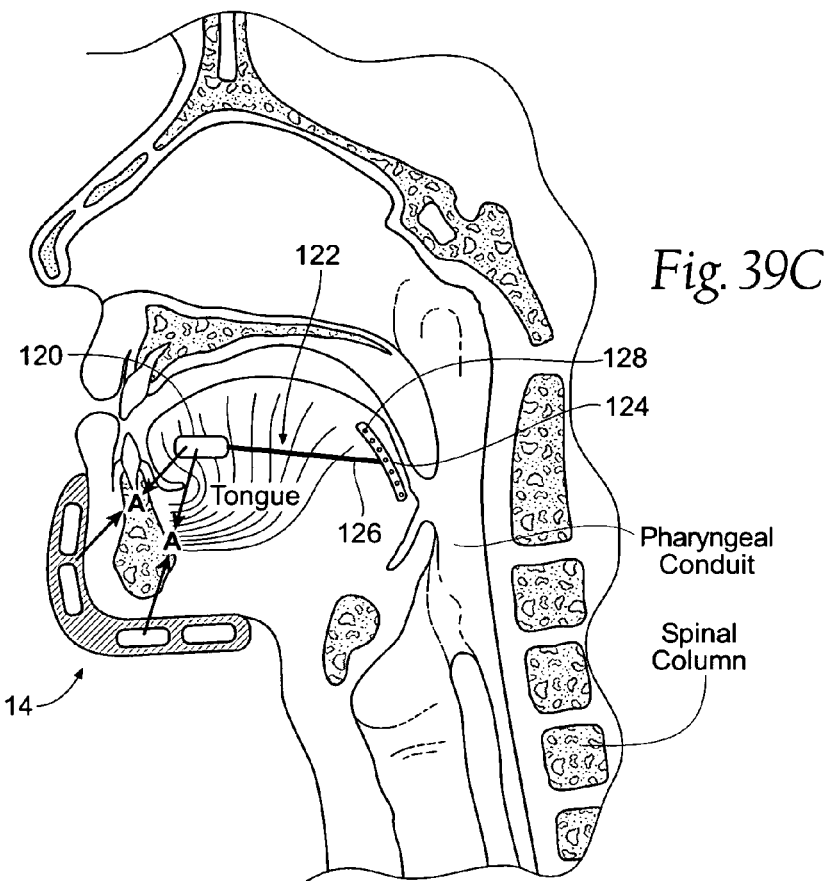
FIGS. 39C and 39D are anatomic side section views of the upper airway of a human, showing the nasal and oral cavities, tongue, hard palate, soft palate, oral pharynx, chin and neck, and further showing another representative tethered magnetic force system of a type shown in FIGS. 40A and 40B, comprising a ferromagnetic structure implanted in a more anterior region of a tongue that interacts with a magnetic structure carried outside an airway (e.g., on a chin), to resist occurrence of the tissue condition shown in FIG. 3, involving the collapse of a tongue against the pharyngeal wall, the ferromagnetic structure including (in FIG. 39C) a single tethered anchoring assembly and (in FIG. 39D) a multiple tether anchoring assembly to stabilize the ferromagnetic structure in close proximity to the external chin-mounted magnetic structure.
Figure 39D:
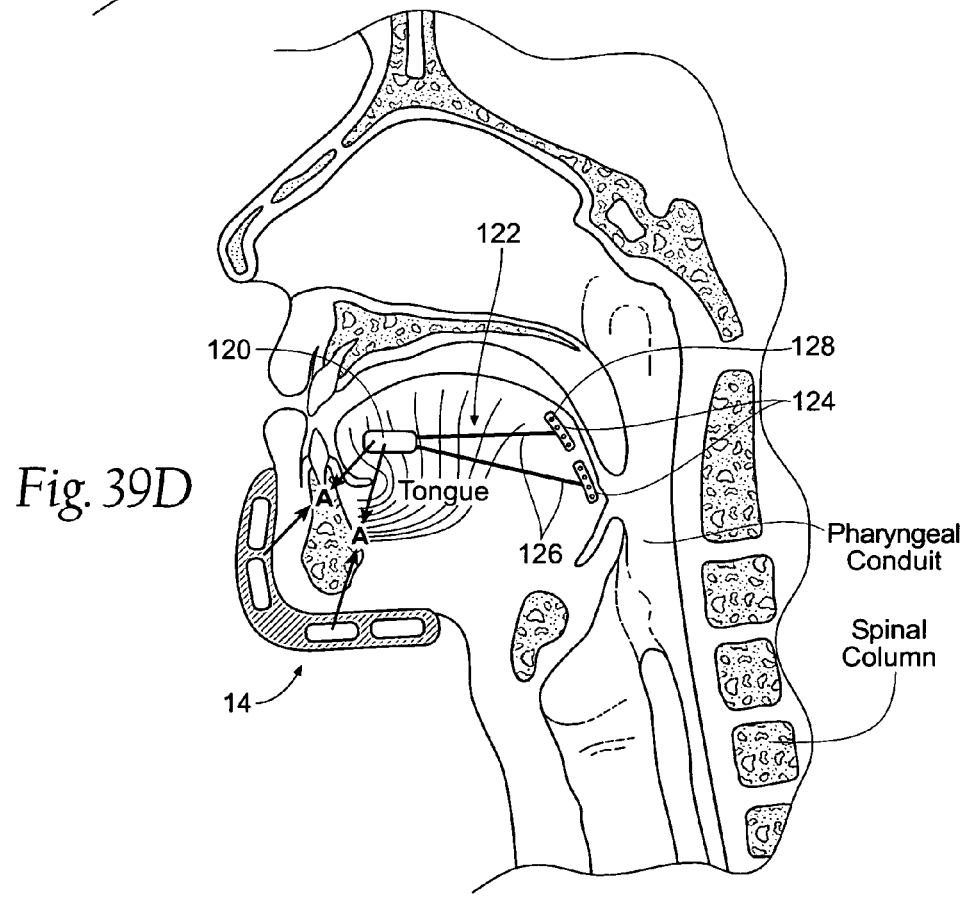

FIGS. 39A and 39C show representative embodiments of a tethered ferromagnetic structure 120 implanted in an anterior region of a tongue in proximity to a magnetic structure 14 as previously described, e.g., a mouthpiece carried within the oral cavity or an external carrier placed on or under the chin or about the neck. For purposes of illustration, FIG. 39A shows the magnetic structure 14 worn externally under the chin, while in FIG. 39C the magnetic structure 14 is part of a chin cup. As seen in FIGS. 39A and 39C, the ferromagnetic structure 120 includes one or more permanent magnets or ferromagnetic materials implanted in tissue beneath the tongue or in an anterior region of the tongue, respectively. In use, the ferromagnetic structure 120 in the tongue magnetically interacts with the magnetic structure 14. The ferromagnetic structure 120 and the magnetic structure 14 are arranged in an attracting orientation, to draw the tongue forward and/or resist posterior movement of the tongue in a manner that would otherwise occlude the airway.

Due to the relatively close proximity of the ferromagnetic structure 120 to the magnetic structure 14, the magnitude of the magnetic force field is maximized. Further, to resist migration of the ferromagnetic structure 120 within tissue in the presence of the relatively strong magnetic force field, the ferromagnetic structure 120 further includes an anchoring system 122. The anchoring system 122 comprises a non-magnetic holding or anchoring structure 124 that is tethered by a band, suture, or another means for attachment 126 to the ferromagnetic structure 120. The presence of the anchoring system 122 resists migration of the ferromagnetic structure 120 within tissue as a result of the magnetic interaction with the magnetic structure 14. Furthermore, the anchoring system pulls the posterior tongue tissue in an anterior direction to prevent collapse of the tongue. The anchoring system 122 may also serve to stabilize the ferromagnetic structure 120 in a relatively large, soft tissue mass, such as the tongue.

Figure 39E:
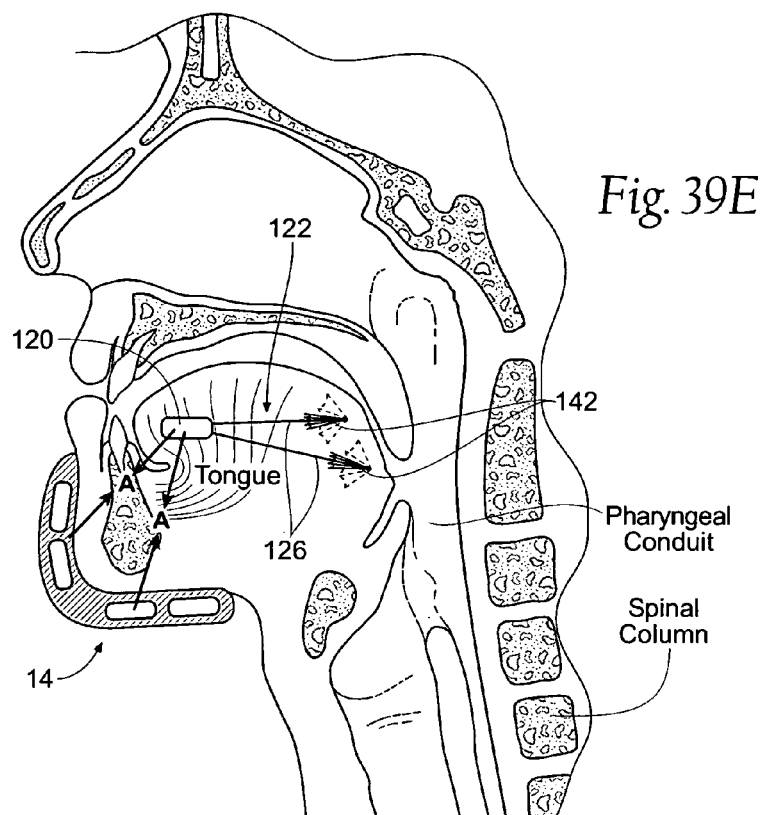
FIG. 39E is a perspective view of a representative tether anchoring assembly that includes an umbrella-like anchor that collapses for implantation and expands in situ within the implantation site.

As shown in FIGS. 39A and 39C, the anchoring structure 124 is implanted in a tissue mass spaced from and posterior to the ferromagnetic structure 120, e.g., at the back of the tongue. The anchoring structure 124 can comprise, e.g., a biocompatible woven, formed, or molded structure made from a polymer or fiber or fabric or non-ferrous metallic material, which resists deterioration, while exhibiting sufficient flexibility to prevent discomfort or affecting speech or swallowing. As shown in FIGS. 39A and 39C, the holding structure 124 may include perforations 128. The perforations 128 impart greater flexibility to the holding structure 124. The perforations 128 also accommodate tissue in-growth, further securing implantation in tissue. Alternatively (as shown in FIG. 39E), the anchoring structure 124 can comprise an expandable umbrella-like structure 142 that collapses for implantation (as shown in solid lines in FIG. 39E) and that expands in situ at the implantation site (as shown in phantom lines in FIG. 39E).

Figure 39F:
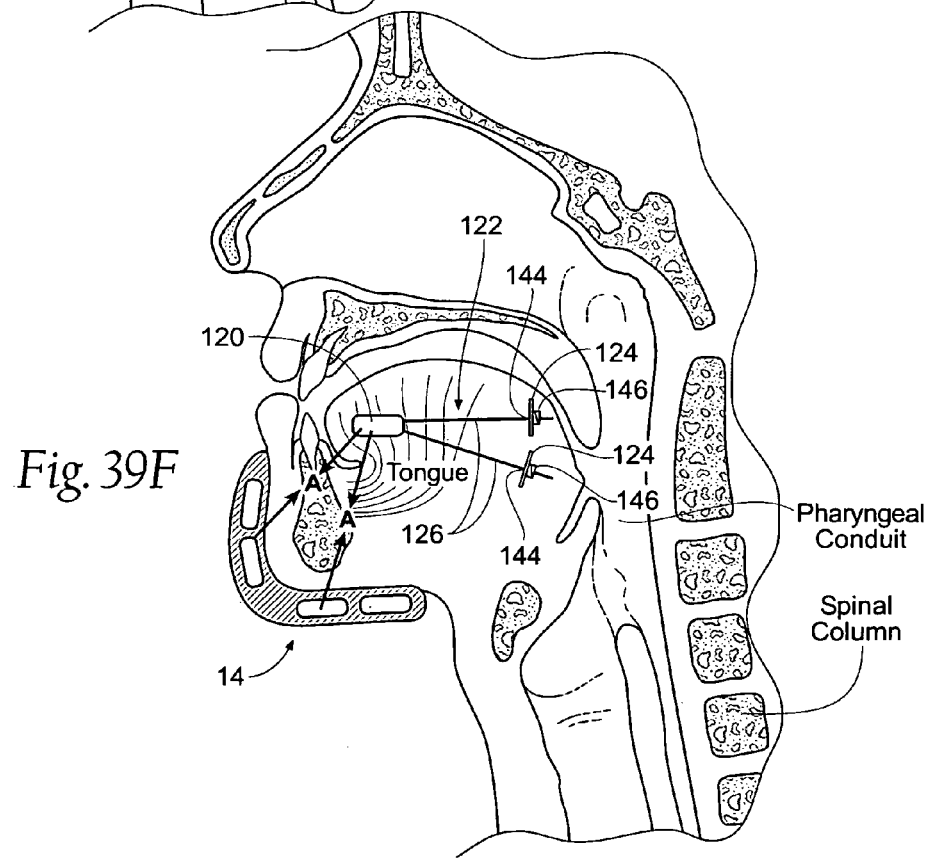
FIG. 39F is a perspective view of a representative tether anchoring assembly that is adjustable and lockable to adjust and control tension.

The means for attachment 126 couples or tethers the ferromagnetic structure 120 to the holding or anchoring structure 124. The means for attachment 126 may comprise a generally non-elastic material, e.g., a non-resorbable suture material, other woven biocompatible lacing or fabric, or a non-woven polymer strip such as nylon or acetal or a biocompatible metallic material such as nickel titanium alloy (Nitinol®). The means for attachment 126 may comprise a biocompatible stem with perforations to permit tissue in-growth and may also include barbs or hooks deploying from the stem, to further stabilize the tethered ferromagnetic structure. Alternatively (as shown in FIG. 39F), the means for attachment 126 may be sized and configured to be passed or threaded through an aperture 144 in the anchoring structure 124 and locked into a position of tension, e.g., using a suture lock 146 or knot. This arrangement makes it possible to adjust and control tension within the implant either during initial implantation or subsequent to the initial implantation, or both.

In an alternative embodiment, the means for attachment 126 may comprise more elastic materials, to provide compliance and increased comfort for the patient. For instance, when swallowing, the tongue moves in a posterior direction and elasticity may prevent arousal from sleep and further may avoid migration of the ferromagnetic structure 120. The anchoring structure 124 is desirably wider than the means for attachment 126, thereby providing the desired resistance for the implanted ferromagnetic structure 120 against being pulled through or out of the implanted tissue region during its magnetic interaction with the close-by magnetic structure 14.

As shown in FIGS. 39B, 39D, 39E, and 39F, the ferromagnetic structure 120 may be individually tethered to two or more anchoring structures 124 by respective means for attachment 126.

In this arrangement, the desired physiologic response (resistance of airway tissue collapse) is achieved by the magnetic structure 14 (e.g., on head gear or a mouthpiece, as previously described) creating a magnetic field that interacts with tethered ferromagnetic structure 120 implanted in the caudal anterior (front) section of the tongue or below the tongue. The implanted ferromagnetic structure 120 has a magnetic orientation opposite to the magnetic orientation of the magnetic structure 14. The magnetic force between opposite magnetic orientations creates an attracting force. As a result of the attracting force, the tongue is drawn forward, toward the front of the oral cavity, to resist an occlusion of the airway at the base of the tongue.

The tether attached to the magnetic structure 120 serves to efficiently transfer the motion or movement of structure 120 to the base of the tongue (the site of the obstruction). The use of the tether is designed to avoid the situation where a magnet in the tongue positioned so as to be moved by application of an external magnet 14 is moved anteriorly, but that motion does not translate to motion of the tongue base at the pharyngeal wall.

E. Anterior Tongue/Hyoid Muscle Magnetic Structures

FIG. 40A shows a representative embodiment of a ferromagnetic structure 120 implanted in an anterior or caudal anterior region of a tongue, or in one or more hyoid muscles such as the suprahyoid muscles, e.g., the mylohyoid muscles, and/or geniohyoid muscles, and/or stylohyoid muscles, and/or digastric muscles, in proximity to previously-described structure 14, e.g., a mouthpiece carried within the oral cavity or an external carrier placed on or under the chin or about the neck. For purposes of illustration, FIG. 40A shows the structure 14 worn externally under the chin; however, the structure 14 can comprise a removable oral appliance fitted over the teeth in the oral cavity or located in the vestibule of the mouth. As seen in FIG. 40A, the ferromagnetic structure 120 includes one or more permanent magnets or ferromagnetic materials 16 implanted in tissue beneath the tongue or in an anterior region of the tongue, respectively. In use, the ferromagnetic structure 120 in the tongue magnetically interacts with structure 14. The ferromagnetic structure 120 and structure 14 are arranged in an attracting orientation, to draw the tongue forward and/or resist posterior movement of the tongue in a manner that would otherwise occlude the airway.

In an alternative embodiment shown in FIG. 40B, the anteriorly-placed ferromagnetic structures 16 are smaller in size than the posteriorly-placed ferromagnetic structures. The posteriorly-placed ferromagnetic structures 16 are larger because the ferromagnetic structure 120 needs to exert a stronger force on the posterior side than on the anterior side, so as to keep the tongue from collapsing and closing off the airway. Furthermore, the posterior end of ferromagnetic structure 120 also contains an aperture 121 through which the structure may become attached or anchored to the hyoid bone. As seen in FIG. 40C, another alternative embodiment consists of a ferromagnetic structure 120 which is smooth on one side, while the embedded ferromagnetic structures project from the opposite side.

As seen in FIGS. 40A to 40C, due to the relatively close proximity of the ferromagnetic structure 120 to structure 14 as well as the large area covered by ferromagnetic structure 120, the magnitude of the magnetic force field is maximized.

In this arrangement, the desired physiologic response (resistance of airway tissue collapse) is achieved by structure 14 (e.g., on head gear or a mouthpiece, as previously described) creating a magnetic field that interacts with ferromagnetic structure 120 implanted in the caudal anterior (front) section of the tongue or below the tongue. The implanted ferromagnetic structure 120 has a magnetic orientation opposite to the magnetic orientation of structure 14. The magnetic force between opposite magnetic orientations creates an attracting force. As a result of the attracting force, the tongue is drawn forward, toward the front of the oral cavity, to resist an occlusion of the airway at the base of the tongue.

IV. Other Representative Magnetic Structures for Dynamic Tissue Regions

A. Self-Centering Magnetic Structures

Figure 19:
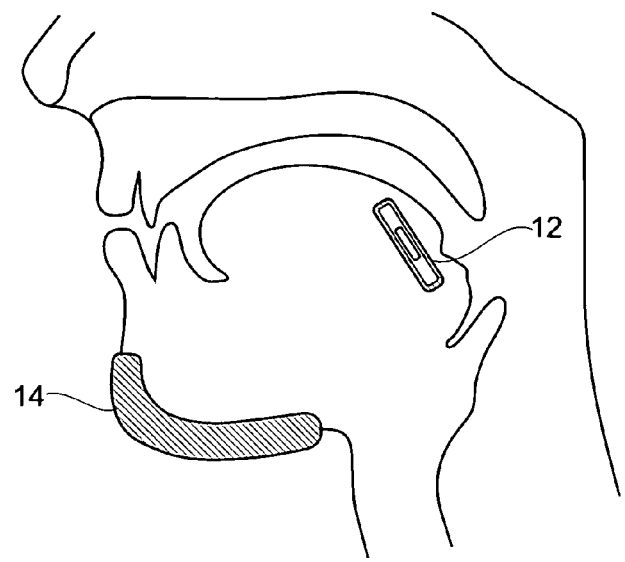
FIG. 19 is an anatomic side section view of the upper airway of a human, showing the nasal and oral cavities, tongue, hard palate, soft palate, oral pharynx, chin and neck, and further showing a representative magnetic force system of a type shown in FIG. 4A in which a ferromagnetic structure implanted in a region of a tongue includes mobile ferromagnetic material that interacts with a magnetic structure carried outside an airway (e.g., on a chin and/or jaw), to resist occurrence of the tissue condition shown in FIG. 3, involving the collapse of a tongue and soft palate/uvula against the pharyngeal wall.

FIG. 19 shows in a diagrammatic way a magnetic system comprising two magnetic structures 12 and 14. As described before, the structures are sized and configured to be placed in or on spaced apart tissue regions in a mutually aligned orientation that generates magnetic interaction between the two structures. Depending upon the polarities of the two structures 12 and 14, the magnetic interaction can comprise, either a magnetic attracting force between the two structures, to resist movement of the two tissue regions away from each other, or a magnetic repelling force between the two structures, to resist movement of the two tissue regions toward each other, or a combination of these and other forces.

As stated before, unless the structures 12 and 14 are aligned in a theoretically ideal fashion, the magnetic interaction will urge the most mobile of the structures (in FIG. 19, the structure 12) to seek an alignment with the least mobile of the structures (in FIG. 19, the structure 14) closest to the theoretically ideal position. Under these circumstances, the better the structures 12 and 14 are aligned, the less magnetic force is lost and the less torque is experienced by the most mobile structure. Practically speaking from both an anatomic and surgical perspective, it is difficult to achieve and maintain theoretically ideal alignment of magnetic structures carried in or on tissue. Given this difficulty, due to misalignment, a surgically implanted magnetic system may dissipate some or a large part of the intended magnetic force.

Figure 20A:
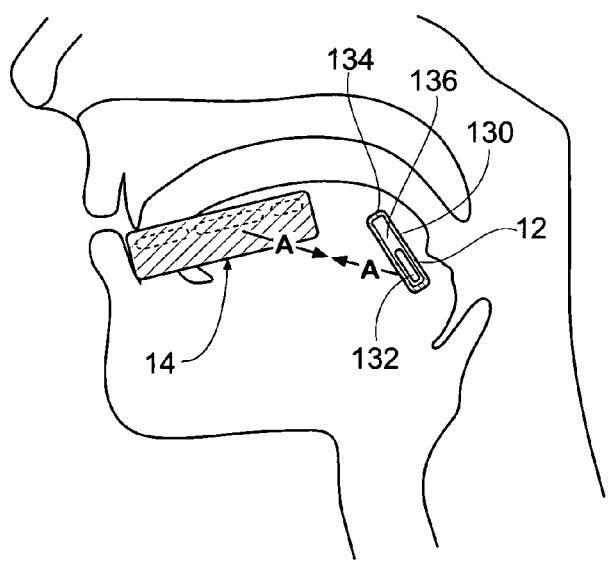
FIGS. 20A and 20B are anatomic side section views of the upper airway of a human, showing the nasal and oral cavities, tongue, hard palate, soft palate, oral pharynx, chin and neck, and further showing a representative magnetic force system of a type shown in FIG. 4B in which a ferromagnetic structure implanted in a region of a tongue includes mobile ferromagnetic material that interacts with a magnetic structure carried inside an airway (e.g., on teeth within an oral cavity), to resist occurrence of the tissue condition shown in FIG. 3, involving the collapse of a tongue and soft palate/uvula against the pharyngeal wall.
Figure 20B:
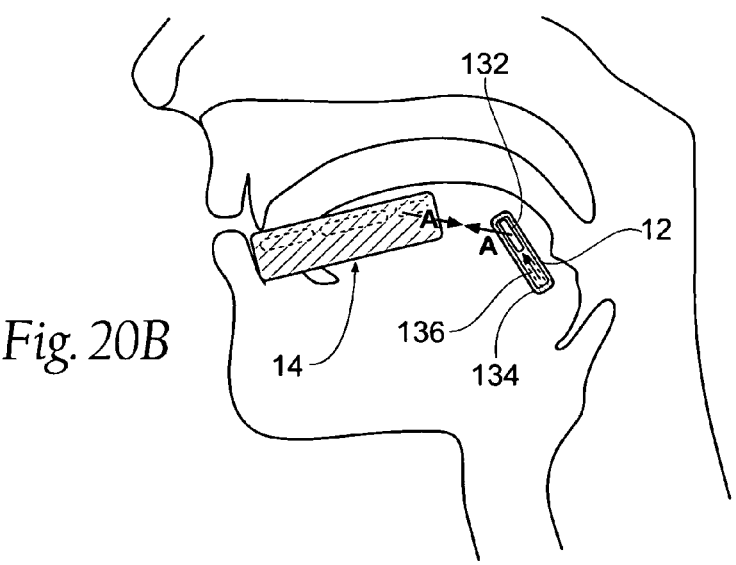

In the system shown in FIG. 20A, at least one of the structures 12 or 14 comprises a self-centering magnetic structure 130. The self-centering magnetic structure 130 comprises at least one mobile magnet 132 enclosed in a capsule or container 134. The shape of the mobile magnet 132 relative to the capsule or container 134 is configured and sized to permit the mobile magnet 132 to translate or move freely within the boundaries of the capsule or container 134 in response to misaligned magnetic interaction with the other structure 14. For example, as shown in FIG. 20A, when misalignment between the self-centering structure 130 and the other structure 14 occurs, the mobile magnet 132 in the self-centering structure 130 will translate or move within the boundaries of the capsule or container 134 (as shown in FIG. 20B) to seek a theoretically ideal alignment with respect to the other structure 14. As relative tissue orientations dynamically change, the mobile magnet 132 will also dynamically translate or move within the boundaries of the capsule or structure 134 to maintain the best possible alignment with the other structure. The boundaries of the capsule or container 134 provide a region of open space 136 where the mobile magnet can maneuver relatively unimpeded to seek the best possible alignment with the other structure. In FIGS. 20A and 20B, a Tongue System 10*a* is shown for purposes of illustration. As shown in FIGS. 20A and 20B, the Tongue System 10*a* comprises a self-centering magnetic tongue implant 130 interacting with an internal magnetic array 14.

Figure 21A:
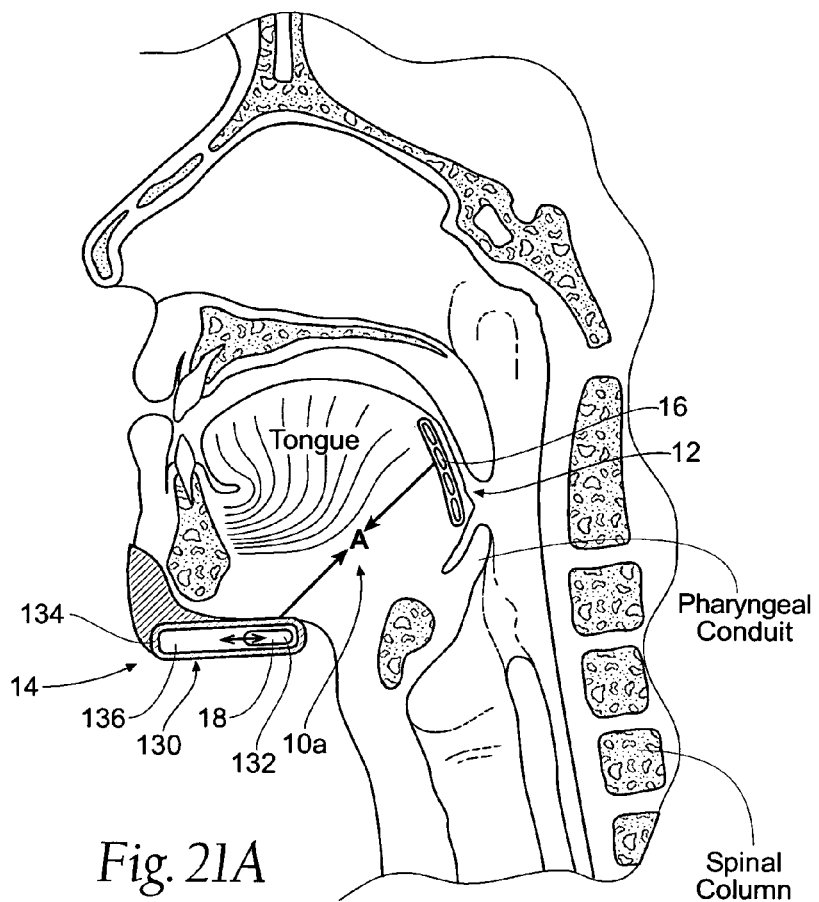
FIG. 21A is an anatomic side section view of the upper airway of a human, showing the nasal and oral cavities, tongue, hard palate, soft palate, oral pharynx, chin and neck, and further showing a representative magnetic force system of a type shown in FIG. 4A in which a ferromagnetic structure implanted in a region of a tongue interacts with a magnetic structure that includes mobile magnetic material carried outside an airway (e.g., on a chin and/or jaw), to resist occurrence of the tissue condition shown in FIG. 3, involving the collapse of a tongue and soft palate/uvula against the pharyngeal wall.

As shown in FIG. 21A, the self-centering magnetic structure 130 may comprise a magnetic structure 14 like that previously described that is sized and configured to be placed in or on tissue outside an airway, e.g., comprising a carrier worn on the chin or about the neck. In this arrangement, the self-centering magnetic structure is intended to be placed in association with another magnetic structure 12 sized and configured to be placed in or on tissue within an airway, e.g., on the tongue, soft palate/uvula, or both. Together, the self-centering structure and the other structure 12 form a system 10*a*, 10*b*, or 10*c*, as previously described. In FIG. 21A, a Tongue System 10*a* is shown for purposes of illustration. As shown in FIG. 21A, the Tongue System 10*a* comprises a tongue implant 12 interacting with an external, self-centering magnetic structure 130.

Figure 21B:
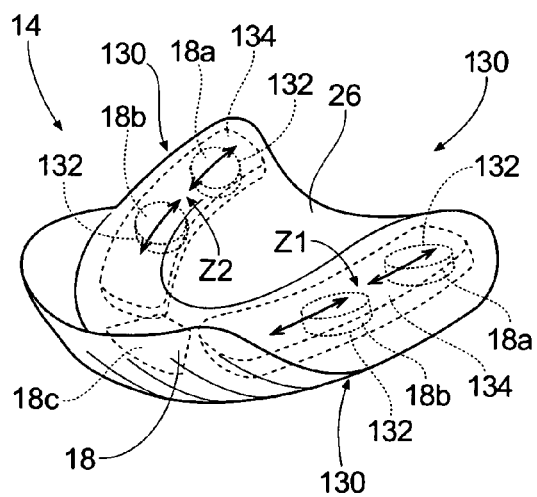
FIGS. 21B to 21F are perspective views of representative embodiments of a magnetic structure sized and configured to be worn within an airway, e.g., on teeth within an oral cavity, that includes mobile magnetic material, forming a part of the system shown in FIG. 21A.
Figure 21C:
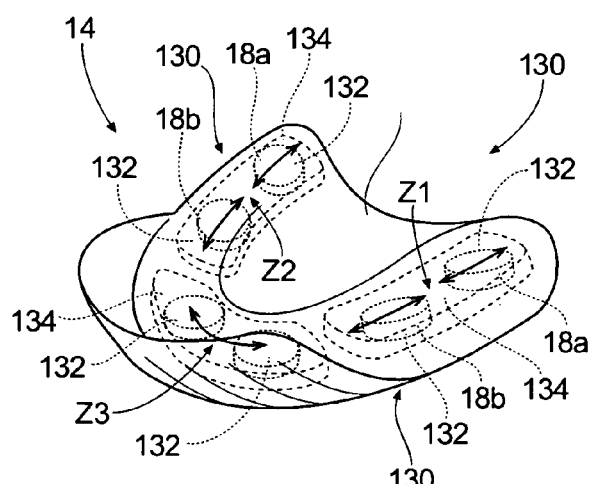
Figure 21D:
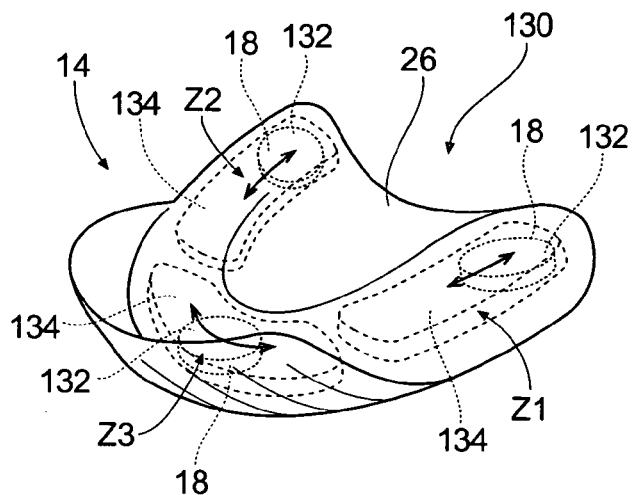

As shown in FIG. 21B, the self-centering magnetic structure 130 can comprise a carrier 26 that includes at least one capsule 134 housing at least one mobile magnet 132. In the embodiment shown in FIG. 21B, the capsule 134 is compartmentalized for purposes of illustration into two spatially separate zones Z1 and Z2, each housing at least one mobile magnet 132 (generally corresponding to the posterior and intermediate regions 18a and 18b shown in FIG. 12C). In the arrangement, the most anterior magnetic region (region 18c in FIG. 12C) can comprise one or more magnets that are not mobile, or vice versa. In the embodiment shown in FIG. 21C, the capsule 134 is compartmentalized for purposes of illustration into three separate zones Z1, Z2, and Z3 (generally similar to the regions 18a, 18b, and 18c in FIG. 12C), each housing at least one mobile magnet 132. The zones Z1, Z2, and Z3 can also be viewed as being separate capsules 134. As shown in FIGS. 21B and 21C, each zone or capsule may contain a plurality of smaller mobile magnets, commensurate with the available volume of the zone or capsule, allowing the mobile magnets to move freely and align themselves within the capsule with the other structure 12. The separate zones Z1, Z2, and Z3 or capsules 134 keep the mobile magnets 132 in spatial zones, so that the mobile magnets 132 do not congregate in one location. Each zone Z1, Z2, and Z3 or capsule 134 is sized and configured to accommodate allowable, defined and controlled movement of the mobile magnet or magnets 132 housed within its boundaries. Alternatively, as shown in FIG. 21D, any or all zones Z1, Z2, or Z3 or capsules 134 may contain a single, larger mobile magnet 132.

Figure 21E:
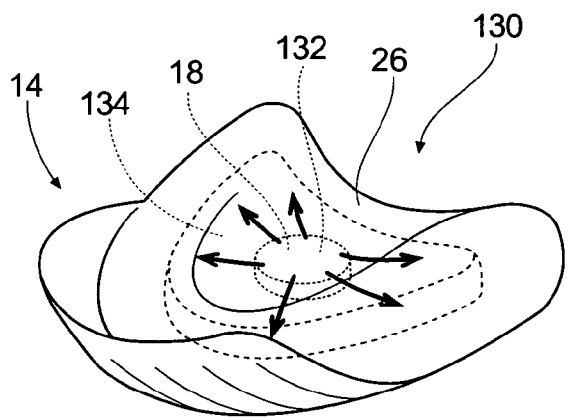
Figure 21F:
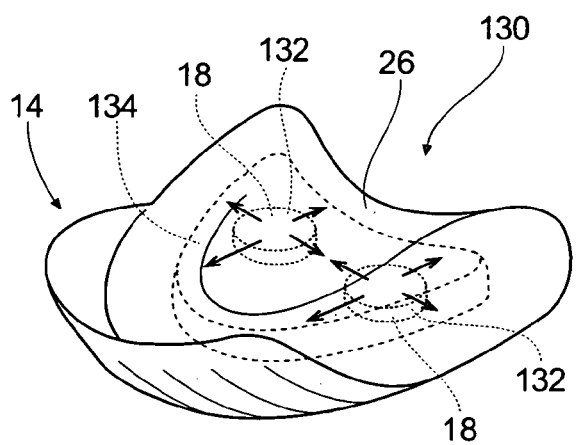

As shown in FIGS. 21E and 21F, the self-centering magnetic structure 130 can include a single zone or capsule that is centrally located, to be, in use, essentially under the tongue. The zone or capsule 134 can accommodate a single, larger mobile magnet 132 (as shown in FIG. 21E) or more than one smaller mobile magnet 132 in the centrally-located zone or capsule 134 that is essentially located under the tongue (as shown in FIG. 21F).

Because the self-centering magnetic structures 130 shown in FIGS. 21A to 21F are intended to be placed on external tissue, the internal volume of the zones or capsules can be relatively large (compared to a capsule in a structure that is intended to be implanted in tissue), thereby providing a relatively large freedom of movement for the mobile magnet it houses.

Alternatively, as shown in FIG. 22A, the self-centering magnetic structure 130 can be sized and configured for placement within an oral cavity, e.g., inside, outside, or on top of the lower or upper teeth, as has already been described. In this arrangement, the self-centering magnetic structure 130 is intended to be placed in association with another magnetic structure (in FIG. 22A, magnetic structure 12) sized and configured to be placed in or on tissue within an airway, e.g., on the tongue, soft palate/uvula, or both. Together, the self-centering structure and the other structure 12 form a system 10a, 10b, or 10c, as previously described. In FIG. 22A, a Soft Palate System 10b is shown for purposes of illustration. The Soft Palate System 10b in FIG. 22A comprises a soft palate implant 12 interacting with an internal, self-centering magnetic structure 130.

In this embodiment, like the embodiments shown in FIGS. 21A to 21F, the self-centering magnetic structure 130 comprises at least one capsule 134 housing at least one mobile magnet 132. In FIG. 22B, like FIG. 21B, the capsule 134 is compartmentalized for purposes of illustration into one or more separate spatial zones Z1 and Z2 each sized and configured to accommodate unimpeded movement of at least one mobile magnet 132 within its boundaries. As before stated, the zones Z1 and Z2 can also be viewed as being separate capsules 134. The separate zones Z1 and Z2 or capsules 134 keep the mobile magnets 132 in spatial zones, so that the mobile magnets 132 do not congregate in one location. Because the structure shown in FIG. 22B is intended to be placed within the airway, the internal volume of the zones Z1 and Z2 or capsules 134 will be relatively smaller, compared to a capsule in a structure like that in FIG. 21B, which is intended to be externally worn. Still, the zones Z1 and Z2 or capsules 134 and mobile magnets 132 they house can be mutually sized and configured to provide a relatively large freedom of movement for the mobile magnets 132. As shown in FIG. 22B, each zone Z1 and Z2 or capsule 134 may contain a single mobile magnet, or alternatively, as shown in FIG. 22C, each zone or capsule 134 may be compartmentalized to contain a plurality of smaller mobile magnets 132. The number of zones and/or mobile magnets can vary, as shown in FIGS. 21A to 21F. Also, as previously described, a given structure 14 can include both mobile magnets 132 and non-mobile magnets 18 (for example 18c shown in FIG. 21B). Many variations are contemplated.

Figure 23A:
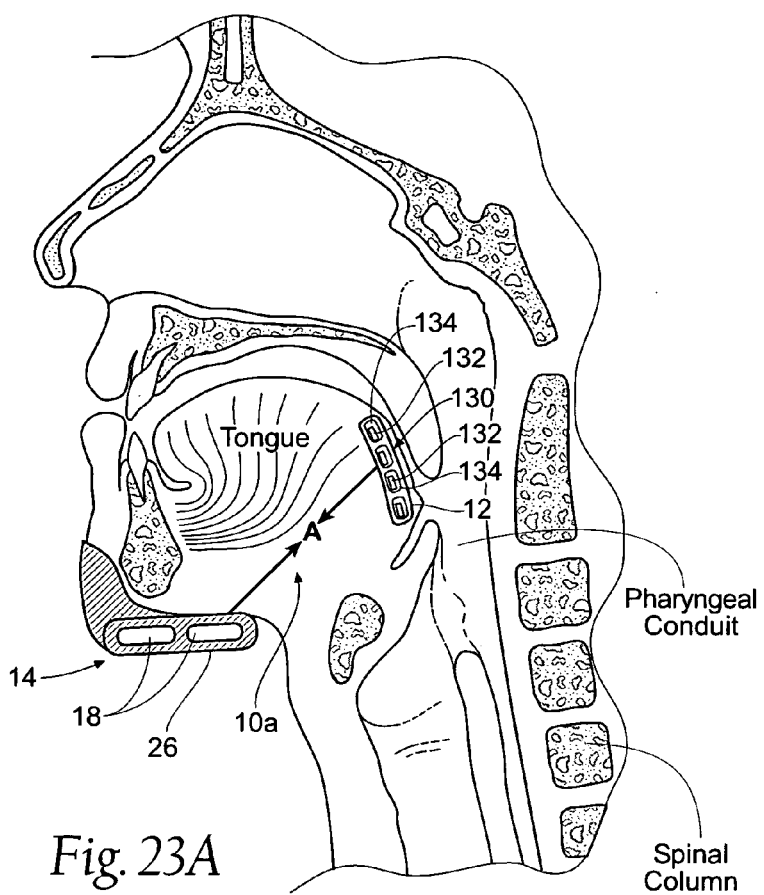
FIG. 23A is an anatomic side section view of the upper airway of a human, showing the nasal and oral cavities, tongue, hard palate, soft palate, oral pharynx, chin and neck, and further showing a representative magnetic force system of a type shown in FIG. 4A in which a ferromagnetic structure implanted in a region of a tongue includes mobile ferromagnetic material that interacts with a magnetic structure carried outside an airway (e.g., on a chin and/or jaw), to resist occurrence of the tissue condition shown in FIG. 3, involving the collapse of a tongue and soft palate/uvula against the pharyngeal wall.

As shown in FIG. 23A, the self-centering magnetic structure 130 may comprise a magnetic structure 12, like that previously described, that is sized and configured to be placed in or on tissue inside an airway, e.g., comprising a carrier placed in or on a tongue and/or a soft palate/uvula, as has already been described. In this arrangement, the self-centering magnetic structure 130 is intended to be placed in association with another magnetic structure 14 sized and configured to be placed in or on tissue outside an airway (on the chin or neck) or inside the airway (on the lower teeth). Together, the self-centering structure and the other structure 12 form a system 10a, 10b, or 10c, as previously described. In FIG. 23A, a Tongue System 10a is shown for purposes of illustration. The Tongue System 10a in FIG. 23A comprises a self-centering tongue implant structure 130 interacting with an external magnetic structure 14. In this arrangement, the interaction between the self-centering tongue implant structure 130 and the external structure 14 places a torque on the tongue. It should be appreciated that other structures 14 can also comprise a self-centering external structure of a type shown in FIGS. 21A/B/C/D/E/F or a self-centering internal structure of a type shown in FIGS. 22A/B/C.

Figures 23B, 23C:
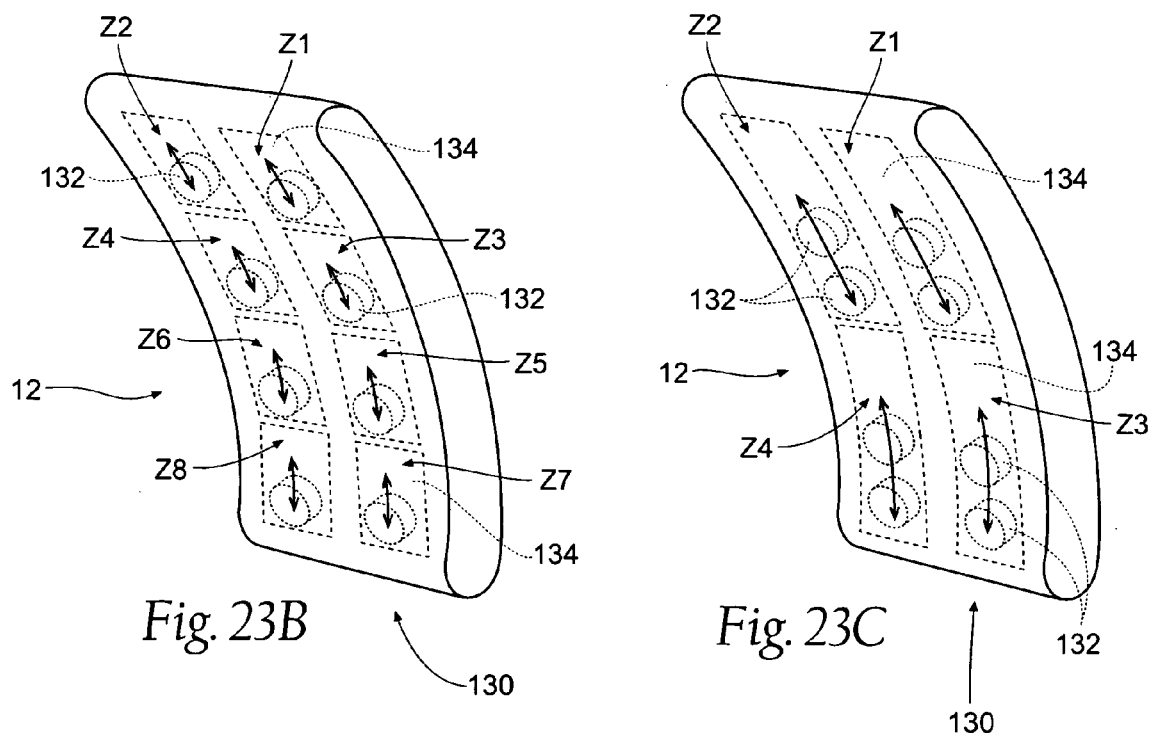
FIGS. 23B and 23C are perspective views of representative embodiments of a magnetic structure sized and configured to be implanted in a region of a tongue that includes mobile magnetic material, forming a part of the system shown in FIG. 23A.

In this embodiment, like the previous embodiments shown in FIGS. 21A/B/C/D/E/F and 22 A/B/C, the self-centering magnetic structure 130 comprises at least one capsule 134 housing at least one mobile magnet 132. In FIG. 23B, like FIGS. 21B and 22B, the capsule 134 is compartmentalized into separate spatial zones Z(N) sized and configured to accommodate unimpeded movement of at least one mobile magnet 132 within its boundaries. In FIG. 23B, there are eight zones shown (i.e., N=8). These zones Z(N) can also be viewed as separate capsules 134. As before described, the separate zones Z(N) or capsules 134 keep the mobile magnets 132 in spatial zones, so that the mobile magnets 132 do not congregate in one location. Because the structure 130 shown in FIG. 23B is intended to be placed within a tongue or soft palate, the internal volume of the zones Z(N) or capsules 134 will be relatively smaller, compared to a capsule in a structure like that in FIG. 21B, which intended to be externally worn. Still, the zones Z(N) or capsules 134 and mobile magnets 132 they house can be mutually sized and configured to provide a relatively large freedom of movement for the mobile magnets 132. As shown in FIG. 23B, any or all zones Z(N) or capsules 134 may contain a single mobile magnet 132, or alternatively, as shown in FIG. 23C, any or all zones Z(N) or capsule 134 may be compartmentalized to contain a plurality of smaller mobile magnets 132. The number of zones and/or mobile magnets can vary, as shown in FIGS. 21A to 21F. Also, as previously described, a given structure 14 can include both mobile magnets 132 and non-mobile magnets 18 (like that shown in FIG. 21B). Many variations are contemplated.

Figure 24A:
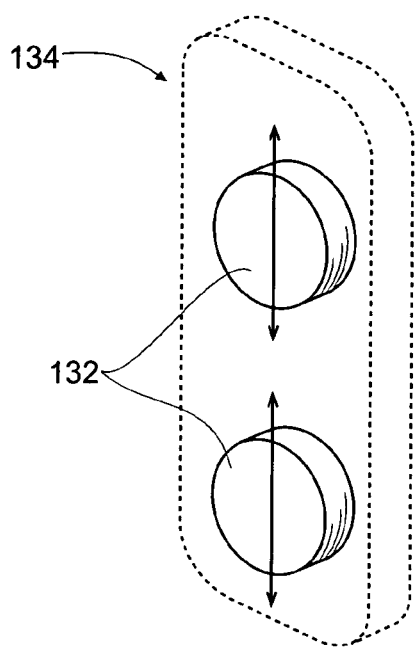
FIGS. 24A, 24B, and 24C are representative diagrammatic embodiments of mobile ferromagnetic materials of various shapes and forms that can form a part of the systems shown in FIG. 19.
Figure 24B:
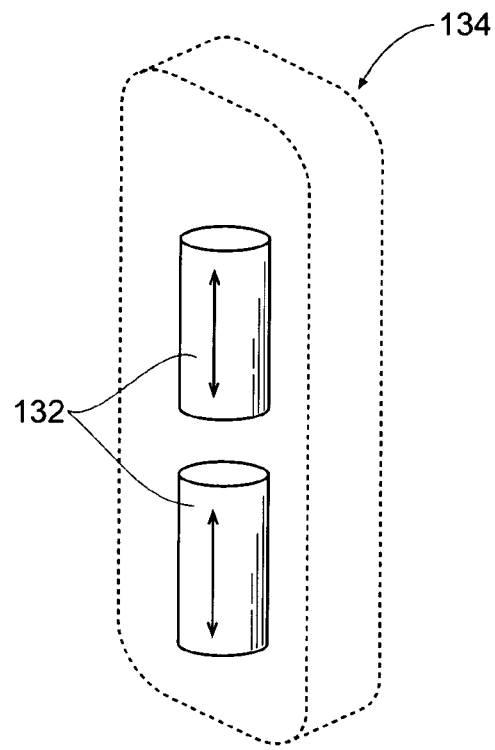
Figure 24C:
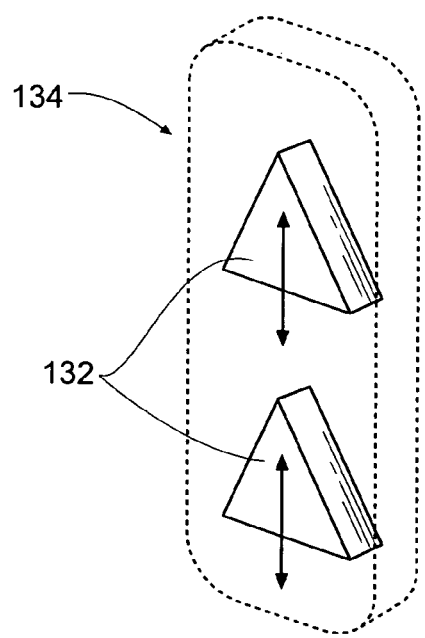

As shown in FIGS. 24A/24B/24C the mobile magnet 132 housed within a given capsule 134 or zone can comprise various shapes. For example, the mobile magnet 132 may have either a disk-like or spherical configuration (FIG. 24A), or a cylindrical configuration (FIG. 24B), or a triangular configuration (FIG. 24C). The shape can be selected to affect the manner in which the mobile magnet 132 moves or translates within the capsule. For example, the mobile cylindrical magnet 132 (FIG. 24B) can roll easily within the capsule 134 in order to align in a proper position. The mobile triangular magnet 132 (FIG. 24C) can include a base having a stronger magnetic flux than the apex of the triangle, to help direct flux in a desired direction.

B. Off-Center Magnetic Structures

The tissue on the lateral sides of the tongue, due to its decreased thickness, may be easier to move than the tissue along the midline of the tongue. Thus, a magnetic structure that is placed in or on tissue on only one side of the tongue can effectively repel a correspondingly positioned magnetic implant in or on a pharyngeal wall.

Figure 25:
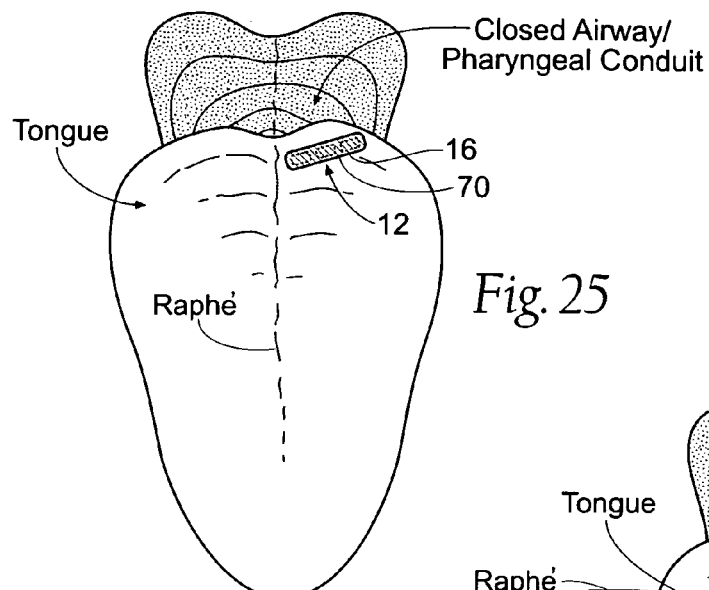
FIG. 25 is an anatomical superior view of the oral cavity, showing the tongue and pharyngeal conduit, and further showing a ferromagnetic structure implanted in a tongue, in which the ferromagnetic structure extends generally asymmetrically only on one lateral side of the tongue, the view also showing a tissue condition as shown in FIG. 3, involving the collapse of a tongue against the pharyngeal wall.

FIG. 25 shows a cross-section of a collapsed pharyngeal conduit, like FIG. 3 but shown from another perspective, sufficient to cause an apneic episode. FIG. 25 also shows the tongue with an implanted magnetic structure 70. Magnetic tongue structure 70 comprises at least two magnets 16 oriented in the same direction, substantially perpendicular to the midline of the tongue. As can be seen in FIG. 25, the location of magnetic tongue structure 70 is generally perpendicular and off-center with respect to the raphé of the tongue. That is, as the embodiment in FIG. 25 shows, all of the structure 70 occupies one side of the tongue along the raphé. Essentially no part of the structure 70 (and therefore no magnets) extends across the raphé to the opposite side of the tongue.

Figure 26A:
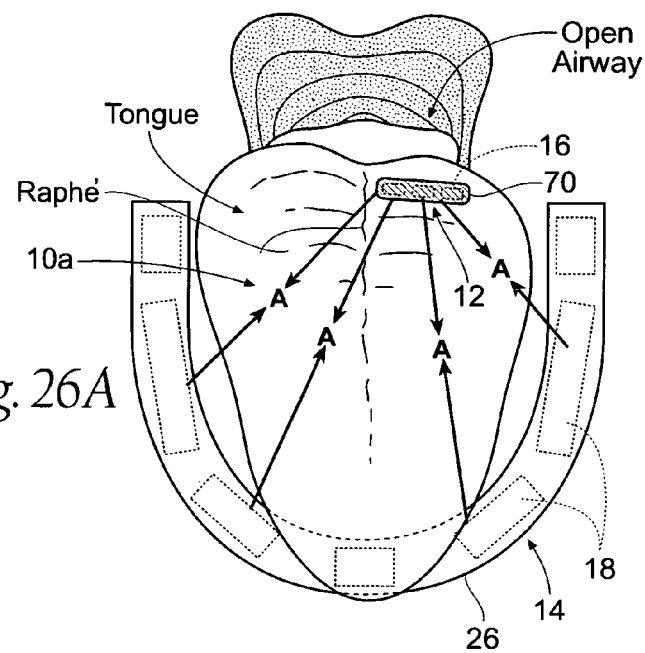
FIG. 26A is an anatomical superior view of the oral cavity, like that shown in FIG. 25, in which the ferromagnetic structure implanted asymmetrically in the tongue interacts with a magnetic structure inside an airway (e.g., on teeth within an oral cavity) having magnets on both lateral sides of the oral cavity, and further showing in this arrangement the magnetic attracting forces that resist occurrence of the tissue condition shown in FIG. 3, involving the collapse of a tongue against the pharyngeal wall.

FIG. 26A shows a new position of the tongue (compared to FIG. 25) due to the interactions between the off-center magnetic tongue structure 70 and an external magnetic structure 14 of the type shown in FIG. 12C/E, which together form an embodiment of a Tongue System 10a. Forces of magnetic attraction between the off-center structure 70 and the structure 14 in FIG. 26A pull the off-center structure 70 anteriorly toward the pharyngeal wall, opening one side of the pharyngeal airway, sufficient to prevent the apneic episode.

Figure 26B:
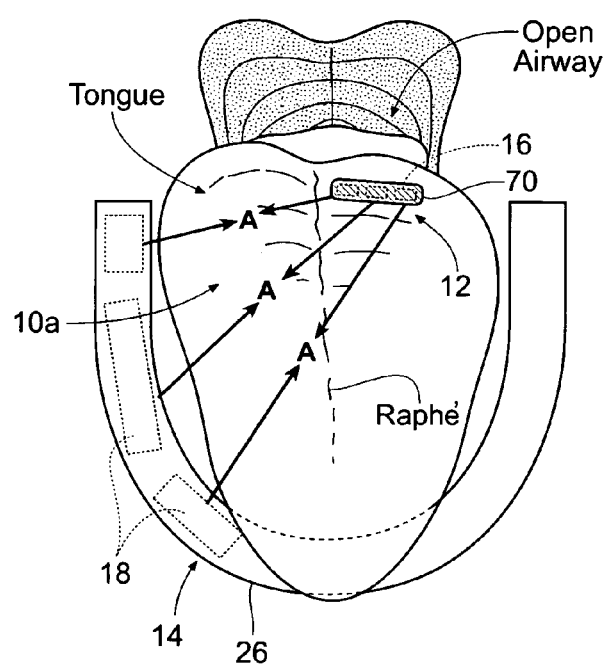
FIG. 26B is an anatomical superior view of the oral cavity, like that shown in FIG. 25, in which the ferromagnetic structure implanted asymmetrically in the tongue interacts with a magnetic structure inside an airway (e.g., on teeth within an oral cavity) having magnets only on one lateral side of the oral cavity opposite to the asymmetric ferromagnetic structure in the tongue, and further showing in this arrangement the magnetic attracting forces that resist occurrence of the tissue condition shown in FIG. 3, involving the collapse of a tongue against the pharyngeal wall.

FIG. 26B shows a new position of the tongue (compared to FIG. 25) due to the interactions between the off-center magnetic tongue structure 70 and an external magnetic structure 14 of the type shown in FIG. 12F, which form another embodiment of a Tongue System 10a. Forces of magnetic attraction between the off-center structure 70 and the structure 14 in FIG. 26B pull the off-center magnetic structure 70 toward the opposite side of the tongue with respect to the location of the off-center magnetic structure 70, opening one side of the pharyngeal airway, sufficient to prevent the apneic episode.

Figure 27:
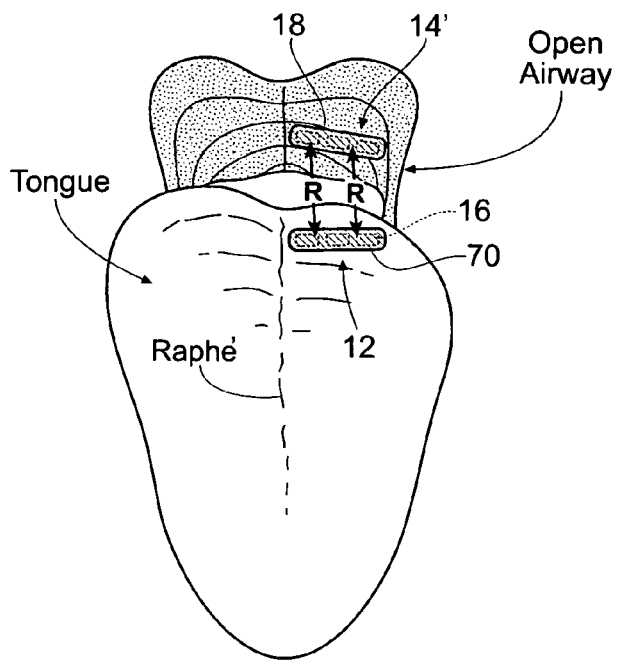
FIG. 27 is an anatomical superior view of the oral cavity, like that shown in FIG. 25, in which the ferromagnetic structure implanted asymmetrically in the tongue interacts with a magnetic structure implanted in a pharyngeal wall opposite to the ferromagnetic structure, and further showing in this arrangement the magnetic repelling forces that resist occurrence of the tissue condition shown in FIG. 3, involving the collapse of a tongue against the pharyngeal wall.

FIG. 27 shows a new position of the tongue (compared to FIG. 25) due to the interactions between the off-center magnetic tongue structure 70 and an internal magnetic structure 14' placed in or on the posterior pharyngeal wall across from the region of the tongue where the off-center magnetic structure 70 is implanted. The internal magnetic structure 14' carries one or more magnets 18 having a polarity facing the airway that is the same as the off-center magnetic structure 70. The off-center magnetic structure 70 magnetically interacts with the pharyngeal wall structure 14 by repelling. Forces of magnetic repulsion between the off-center structure 70 and the structure 14 in FIG. 27 push the magnetic tongue structure 70 anteriorly toward the mouth, opening one side of the pharyngeal airway, sufficient to prevent the apneic episode.

C. Rudder-Type Magnetic Structures

Figure 28:
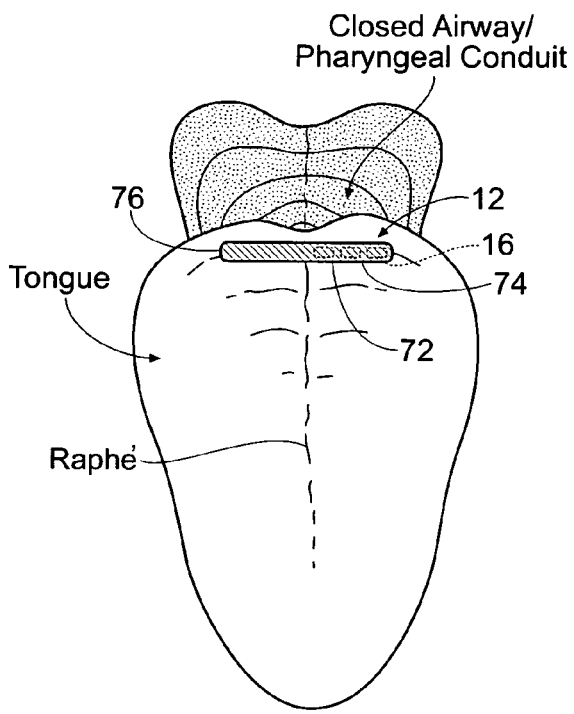
FIG. 28 is an anatomical superior view of the oral cavity, showing the tongue and pharyngeal conduit, and further showing a ferromagnetic structure implanted in a tongue, in which the ferromagnetic structure extends generally asymmetrically only on one lateral side of the tongue, but includes an appendage that is free of a ferromagnetic material extending into the opposite lateral side of the tongue, the view also showing a tissue condition as shown in FIG. 3, involving the collapse of a tongue against the pharyngeal wall.

FIG. 28 shows a cross-section of a collapsed pharyngeal conduit, like FIG. 3 but shown from another perspective, sufficient to cause an apneic episode. FIG. 28 also shows the tongue with an implanted, rudder-type magnetic structure 72. The magnetic structure 72 comprises a first region or arm 74 carrying at least two magnets 16 oriented in the same direction transversally along the midline of the tongue. As can be seen in FIG. 28, the location of the magnets 18 in the arm 74 is off-center with respect and generally perpendicular to the raphé of the tongue, as previously described with respect to FIG. 25. However, unlike the embodiment shown in FIG. 25, the magnetic structure 72 includes a second region or arm 76 that extends across the raphé to the opposite side of the tongue. The region or arm 76 is free or essentially free of magnets, so that essentially no magnets occupy this region of the tongue.

The magnet-free region or arm 76, which extends to a location of the tongue not occupied by the magnets 16, acts as a rudder. Rudder-type magnetic structures 72 of the type shown in FIG. 28 are variants of the off-center magnetic structures 70 shown in FIG. 25. The presence of the rudder 76 serves to move more soft tissue than the off-center structure 70 shown in FIG. 25 and/or to further stabilize the structure 72 during use.

Figure 29A:
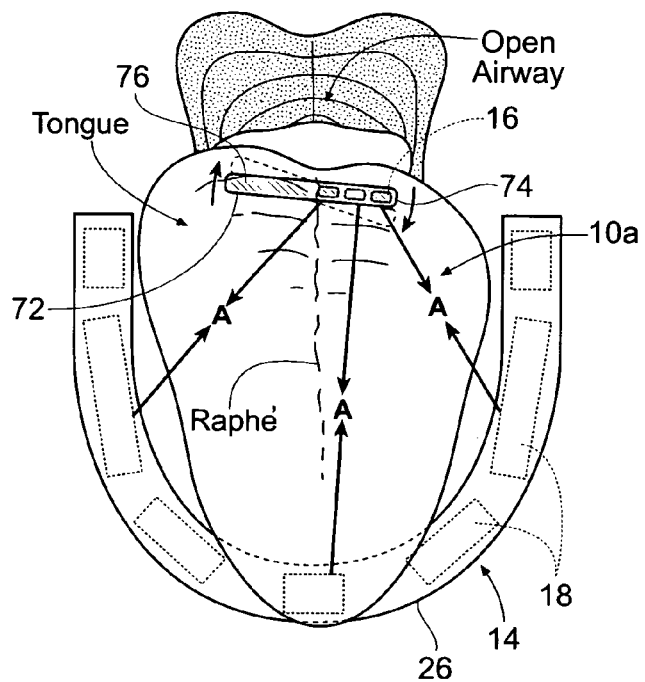
FIG. 29A is an anatomical superior view of the oral cavity, like that shown in FIG. 28, in which the ferromagnetic structure implanted asymmetrically in the tongue with a non-ferromagnetic appendage interacts with a magnetic structure inside an airway (e.g., on teeth within an oral cavity) having magnets on both lateral sides of the oral cavity, and further showing in this arrangement the magnetic attracting forces that resist occurrence of the tissue condition shown in FIG. 3, involving the collapse of a tongue against the pharyngeal wall.

FIG. 29A shows a new position of the tongue (compared to FIG. 28) due to the interactions between the rudder-type magnetic structure 72 and an external magnetic structure 14 of the type shown in FIGS. 12C and 12E, which together form an embodiment of a Tongue System 10a. Forces of magnetic attraction between the rudder-type structure 72 and the structure 14 in FIG. 29A pull the magnetic portion of the tongue structure 72 anteriorly toward the mouth. This is because the magnets 16 of the structure 72 have an S-polarity facing toward the front (anterior) of the oral cavity, and the magnets 18 of the structure 14 have an opposite N-polarity facing inward toward the oral cavity, or vice versa. The rudder portion 76, being essentially free of magnets, is not magnetically attracted, but remains implanted in tissue across the raphé on the other side of the tongue. As a result, the structure 72 will pivot about the rudder portion 76 toward the external magnetic structure 14. The additional surface area of the rudder portion 76 will draw more tissue in the direction of the pivot, and will also serve as a tissue anchor that lends overall stability to the structure 72. The magnetic interaction opens one side of the pharyngeal airway, sufficient to prevent the apneic episode.

Figure 29B:
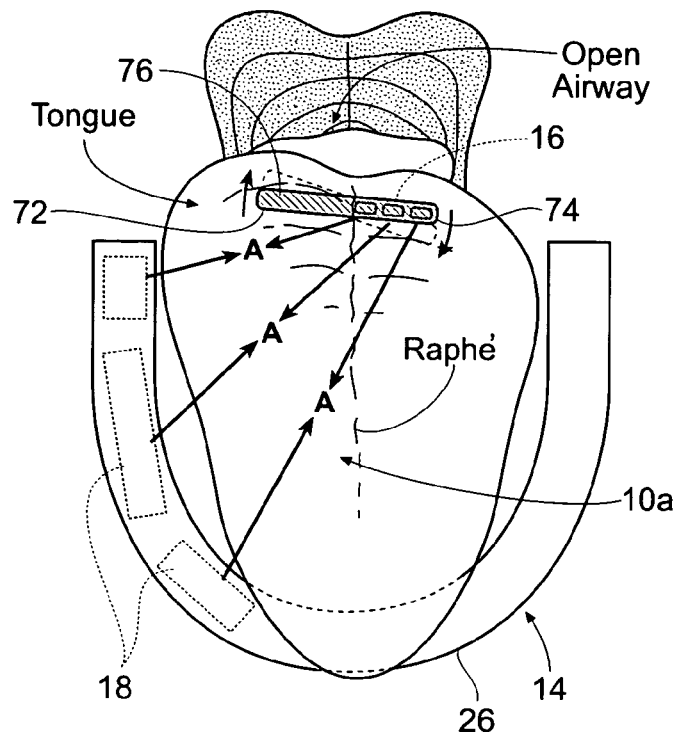
FIG. 29B is an anatomical superior view of the oral cavity, like that shown in FIG. 28, in which the ferromagnetic structure implanted asymmetrically in the tongue with a non-ferromagnetic appendage interacts with a magnetic structure inside an airway (e.g., on teeth within an oral cavity) having magnets only on one lateral side of the oral cavity opposite to the asymmetric ferromagnetic structure in the tongue, and further showing in this arrangement the magnetic attracting forces that resist occurrence of the tissue condition shown in FIG. 3, involving the collapse of a tongue against the pharyngeal wall.

FIG. 29B shows a new position of the tongue (compared to FIG. 25) due to the interactions between the rudder-type magnetic structure 72 and an external magnetic structure 14 of the type shown in FIG. 12F, which form another embodiment of a Tongue System 10a. Forces of magnetic attraction between the rudder-type structure 72 and the structure 14 in FIG. 29B pull the magnetic portion 76 of the rudder-type magnetic portion of the tongue structure 72 toward the opposite side of the tongue with respect to the location of the magnetic portion of the structure 72. This is because the magnets 16 of the structure 72 have an S-polarity facing toward the front (anterior) of the oral cavity, and the magnets 18 of the structure 14 have an opposite N-polarity facing inward toward the oral cavity, or vice versa. The rudder portion 76, being essentially free of magnets, is not magnetically attracted, but remains implanted in tissue across the raphé on the other side of the tongue. As a result, the structure 72 will pivot about the rudder portion toward the external magnetic structure 14. The additional surface area of the rudder portion 76 will draw more tissue in the direction of the pivot, and will also serve as a tissue anchor that lends overall stability to the structure 72. The magnetic interaction opens one side of the pharyngeal airway, sufficient to prevent the apneic episode.

Figure 30:
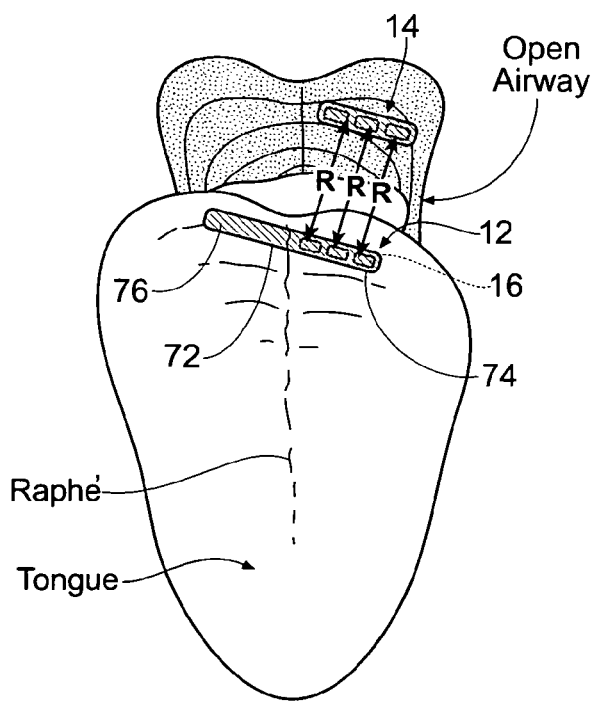
FIG. 30 is an anatomical superior view of the oral cavity, like that shown in FIG. 28, in which the ferromagnetic structure implanted asymmetrically in the tongue with a non-ferromagnetic appendage interacts with a magnetic structure implanted in a pharyngeal wall opposite to the ferromagnetic structure, and further showing in this arrangement the magnetic repelling forces that resist occurrence of the tissue condition shown in FIG. 3, involving the collapse of a tongue against the pharyngeal wall.

FIG. 30 shows a new position of the tongue (compared to FIG. 28) due to the interactions between the rudder-type magnetic structure 72 and an internal magnetic structure 14 placed in or on the posterior pharyngeal wall across from the region of the tongue where the rudder-type magnetic structure 72 is implanted. The internal magnetic structure 14 carries one or more magnets 18 having a polarity facing the airway that is the same as the rudder-type magnetic structure 72. The rudder-type magnetic structure 72 magnetically interacts with the pharyngeal wall structure 14 by repelling. Forces of magnetic repulsion between the rudder-type structure 72 and the structure 14 in FIG. 30 push the magnetic portion 74 of the tongue structure 72 anteriorly toward the mouth. This is because the magnets 16 of the structure 72 have an N-polarity facing the airway, and the magnets 18 of the structure 14 have the same N-polarity facing the airway, or vice versa. The rudder portion 76, being essentially free of magnets, is not magnetically attracted, but remains implanted in tissue across the raphé on the other side of the tongue. As a result, the structure 72 will pivot about the rudder portion 76 away from the internal magnetic structure 14. The additional surface area of the rudder portion 76 will push more tissue in the direction of the pivot, and will also serve as a tissue anchor that lends overall stability to the structure 72. The magnetic interaction opens one side of the pharyngeal airway, sufficient to prevent the apneic episode.

The rudder portion of a rudder-type magnetic structure 72 can be variously sized and configured. For example, as shown in FIGS. 31A/B/C, the main body 78 of the structure 72 can include a rudder portion 76 having a surface area that is increased by providing an appendage 92 (see FIGS. 31A and 31B) that projects outward at a desired angle (e.g., 45° to 90°) from the rudder portion 76. That is (see FIGS. 31A and 31B), given that the main body 78 of the structure lies along a longitudinal axis 84, the axis 82 of the appendage 92 lies at an angle from the longitudinal axis 84. The appendage 92 gives greater depth to the overall implant in the direction of the magnetic field. Generally, magnetic implants having greater depth apply more force to tissue, because of increased surface area and mass. Thus, the appendage 92 serves to apply more force and stability to the implant. Additionally, the appendage 92 may also carry embedded sources of magnetism, in which case the appendage would also lower the distance between magnetic structure 12 and an external magnetic structure 14 with which it magnetically interacts.

As FIGS. 31C and 31D show, the location of magnetic implant 72, when implanted, is desirably centered with respect to the raphé with the longitudinal axis 84 of the main body extending transversely of the raphé and the axis 82 of the rudder appendage 92 extending generally parallel to the raphé. As FIG. 31C shows, the implant 72 is divided into two parts by the raphé of the tongue. On one side 88 of the raphé, at least two magnets 16 are carried by the structure 70. On the other side 86 of the raphé lies the rudder portion 76 with appendage 92, which is desirably free or essentially free of magnetic material. As FIG. 31D shows, the portion 76 and its appendage 92 act as a rudder to help move more tongue tissue as a result of magnetic attraction and/or repulsion between the magnet-carrying side 88 of the implant and another magnetic structure of a type previously described.

Figure 32A:
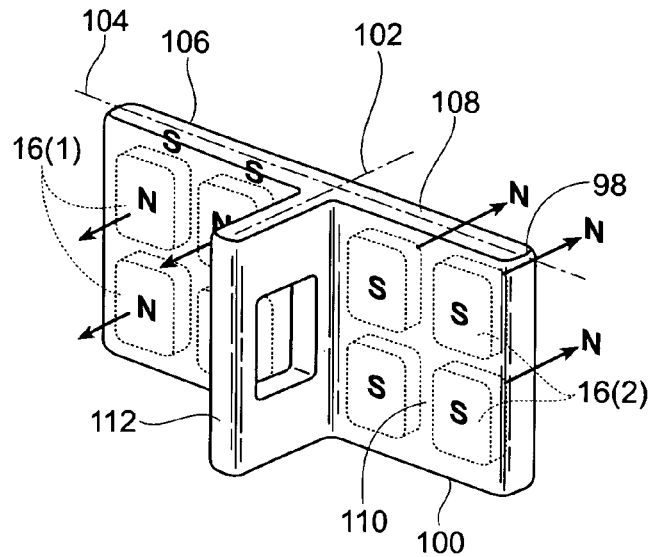
FIGS. 32A and 32B are, respectively, a perspective view and a top view of a representative embodiment of a magnetic structure having opposite arm regions of opposite magnetic polarity and an intermediate non-magnetic rudder-type structure to further stabilize the structure and move more tissue in response to magnetic interaction of a magnetic structure wither inside or outside the airway, or both.
Figure 32B:
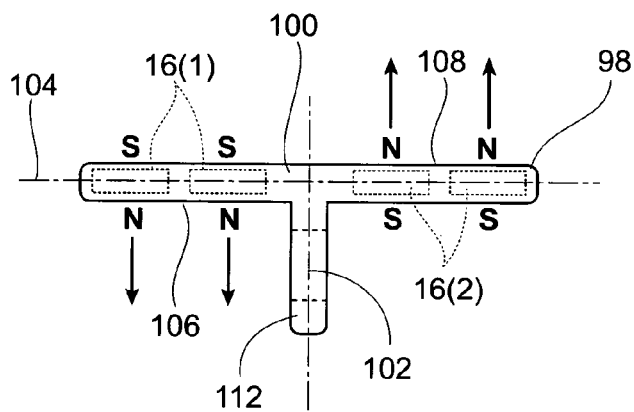

FIGS. 32A and 32B show an alternative embodiment of a rudder-type magnetic structure 98 sized and configured for placement in a tongue. In the embodiment, the rudder-type magnetic structure 98 comprises a main body 100 having a longitudinal axis 104. The main body 100 comprises a first region 106 carrying a first array of one or more magnets 16(1) and a second region 108 carrying a second array of one or more magnets 16(2). As FIGS. 32A and 32B show, the polarity of the magnets in the first array 16(1) is generally opposite to the polarity of the second array 16(2). The main body 100 further comprises an intermediate rudder appendage 112 between the first and second regions 106 and 108 having an axis 102 that projects at an angle from the longitudinal axis 104. The rudder appendage 112 is desirably free or essentially free of magnets. In the illustrated embodiment (see FIGS. 32A and 32B), the magnets of the first array 16(1) have a N-polarity facing in the direction of the rudder appendage 112, and the magnets of the second array 16(2) have a S-polarity facing the direction of the rudder appendage 112.

Figure 33:
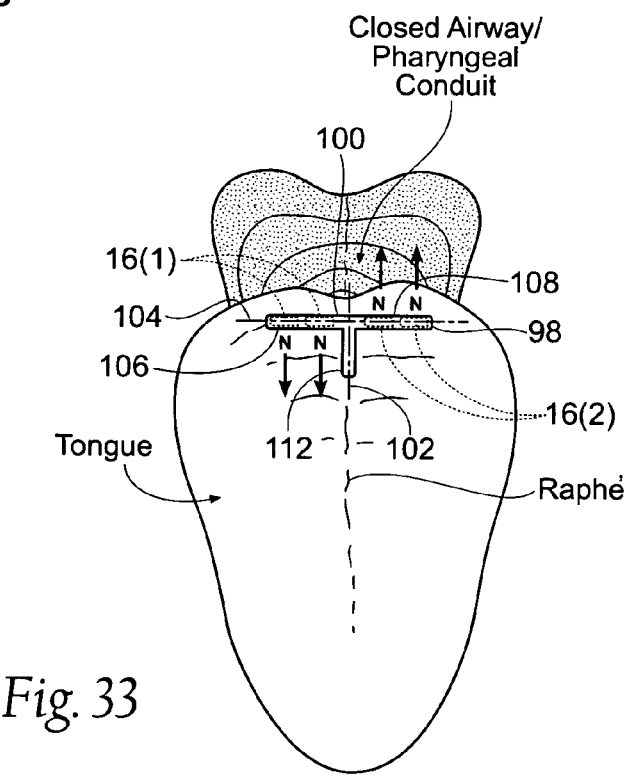
FIG. 33 is an anatomical superior view of the oral cavity, showing the tongue and pharyngeal conduit, and further showing the ferromagnetic structure shown in FIGS. 32A and 32B implanted in a tongue, the view also showing a tissue condition as shown in FIG. 3, involving the collapse of a tongue against the pharyngeal wall.

FIG. 33 shows a cross-section of a collapsed pharyngeal conduit, like FIG. 3 but shown from another perspective, sufficient to cause an apneic episode. FIG. 33 also shows the rudder-type structure 98 shown in FIGS. 32A/B implanted in the tongue. As can be seen in FIG. 33, the main body 100 is implanted with its longitudinal axis 104 extending generally transversely of the raphé of the tongue, with the first region 106 located on one side of the raphé and the second region 108 located on the opposite side of the raphé. The rudder appendage 112 occupies the raphé between the first and second regions, and the axis 102 of the rudder appendage 112 extends generally parallel to the raphé.

Figure 34A:
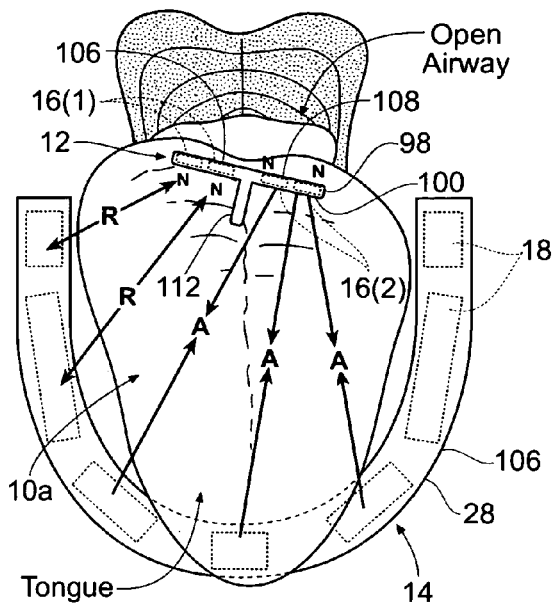
FIGS. 34A and 34B are anatomical superior views of the oral cavity, like that shown in FIG. 33, in which the ferromagnetic structure shown in FIG. 33 interacts with a magnetic structure inside an airway (e.g., on teeth within an oral cavity) having magnets only on one lateral side of the oral cavity, and further showing in this arrangement the magnetic attracting forces that resist occurrence of the tissue condition shown in FIG. 3, involving the collapse of a tongue against the pharyngeal wall.

FIG. 34A shows a new position of the tongue (compared to FIG. 33) due to the interactions between the rudder-type structure 98 shown in FIGS. 32A/B and an external magnetic structure 14 of the type shown in FIGS. 12C/E, which together form an embodiment of a Tongue System 10a. The structure 14 carries magnets 18 having a polarity facing the oral cavity that are opposite to the polarities of the magnets of the second array 16(2) and the same as the polarities of the magnets of the first array 16(1). In the illustrated embodiment, the magnets 18 have a N-polarity facing the oral cavity. As a result, forces of magnetic attraction are generated between the structure 14 and the second array 16(2), whereas forces of magnetic repulsion are generated between the structure 14 and the first array 16(1). The attracting forces pull the second portion 108 of the structure 98 anteriorly toward the mouth, whereas the repelling forces push the first portion 106 of the structure 98 posteriorly toward the pharyngeal wall. The rudder appendage 112, being essentially free of magnets, is not magnetically attracted or repelled, but remains implanted in tissue in the region of the raphé between the two opposite sides of the tongue. The rudder stabilizes the push and pull of the different magnetic interactions. The magnetic interactions open one side of the pharyngeal airway, sufficient to prevent the apneic episode.

Figure 34B:
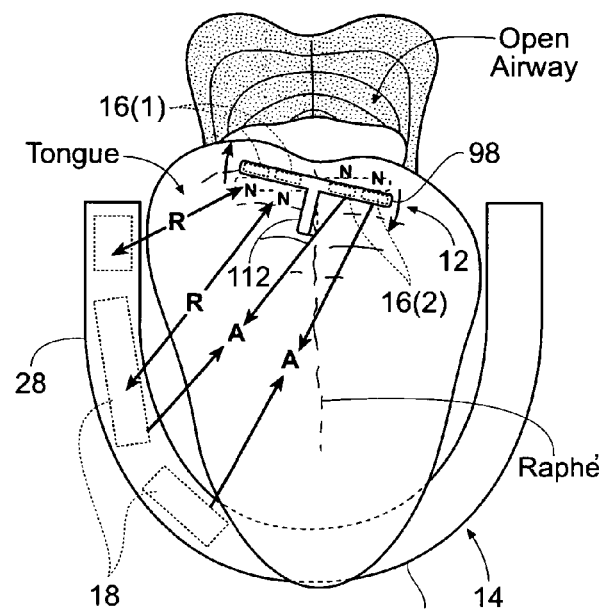

FIG. 34B shows a new position of the tongue (compared to FIG. 33) due to the interactions between the rudder-type structure shown in FIGS. 32A/B and an external magnetic structure 14 of the type shown in FIG. 12E, which form another embodiment of a Tongue System. The structure 14 carries magnets 18 on only the side of the tongue occupied by the first array 16(1). The magnets 18 have a polarity facing the oral cavity that is the same as the polarities of the magnets of the first array 16(1) and opposite to the polarities of the magnets of the second array 16(2). The attracting forces pull the second portion 108 of the structure 98 toward the opposite side of the tongue, whereas the repelling forces push the first portion 106 of the structure posteriorly toward the pharyngeal wall. The rudder appendage 112, being essentially free of magnets, is not magnetically attracted or repelled, but remains implanted in tissue in the region of the raphé between the two opposite sides of the tongue. As a result, the second portion 108 of the structure 98 will pivot toward the external magnetic structure 14, as the first portion 106 of the structure 98 pivots away from the external magnetic structure 14. The rudder appendage 112 stabilizes the push-and-pull of the different magnetic interactions, and will draw more tissue in the direction of the pivot. The magnetic interactions open one side of the pharyngeal airway, sufficient to prevent the apneic episode.

Figure 35:
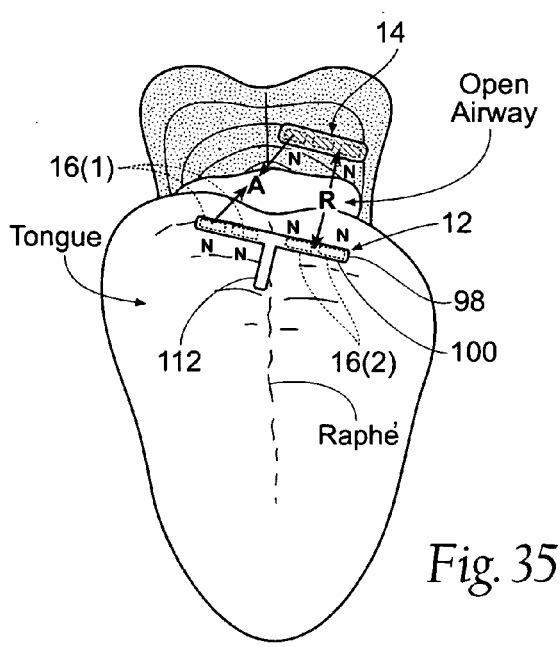
FIG. 35 is an anatomical superior view of the oral cavity, like that shown in FIG. 33, in which the ferromagnetic structure shown in FIG. 33 interacts with a magnetic structure implanted in a pharyngeal wall opposite to the ferromagnetic structure, and further showing in this arrangement the magnetic attracting and repelling forces that resist occurrence of the tissue condition shown in FIG. 3, involving the collapse of a tongue against the pharyngeal wall.

FIG. 35 shows a new position of the tongue (compared to FIG. 33) due to the interactions between the rudder-type structure shown in FIGS. 32A/B and an internal magnetic structure 14 placed in or on the posterior pharyngeal wall across from the region of the tongue where the first array of the structure is implanted. The internal magnetic structure 14 carries one or more magnets 18 having a polarity facing the airway that is the same as the magnets in the second array 16(2) and that is opposite to the magnets in the first array 16(1). As a result, forces of magnetic repulsion are generated between the structure 14 and the second array 16(2), whereas forces of magnetic attraction are generated between the structure 14 and the first array 16(1). The repelling forces push the second portion 108 of the structure 98 toward the oral cavity, whereas the attracting forces pull the first portion 106 of the structure posteriorly toward the pharyngeal wall. The rudder appendage 112, being essentially free of magnets, is not magnetically attracted or repelled, but remains implanted in tissue in the region of the raphé between the two opposite sides of the tongue. As a result, the second portion 108 of the structure 98 will pivot away from the internal magnetic structure 14, as the first portion 106 of the structure 98 pivots toward the internal magnetic structure 14. The rudder appendage 112 stabilizes the push-and-pull of the different magnetic interactions, and will draw tissue in the direction of the pivot. The magnetic interactions open one side of the pharyngeal airway, sufficient to prevent the apneic episode.

D. Ferromagnet with an Elastic Component

Figure 41A:
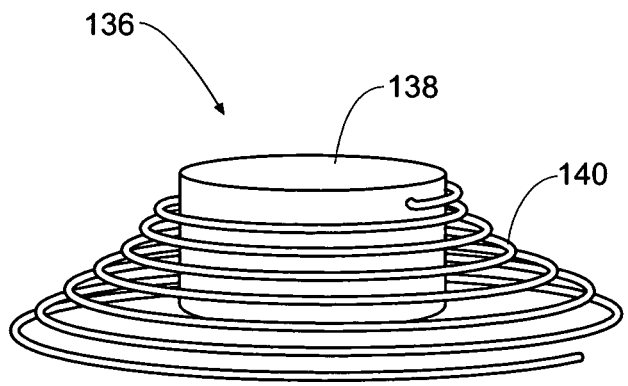
FIGS. 41A and 41B show devices that consist of one or more ferromagnetic structure(s) attached to one or more elastic components sized and configured to deflect under load in a prescribed manner and to recover an initial shape when unloaded.
Figure 41B:
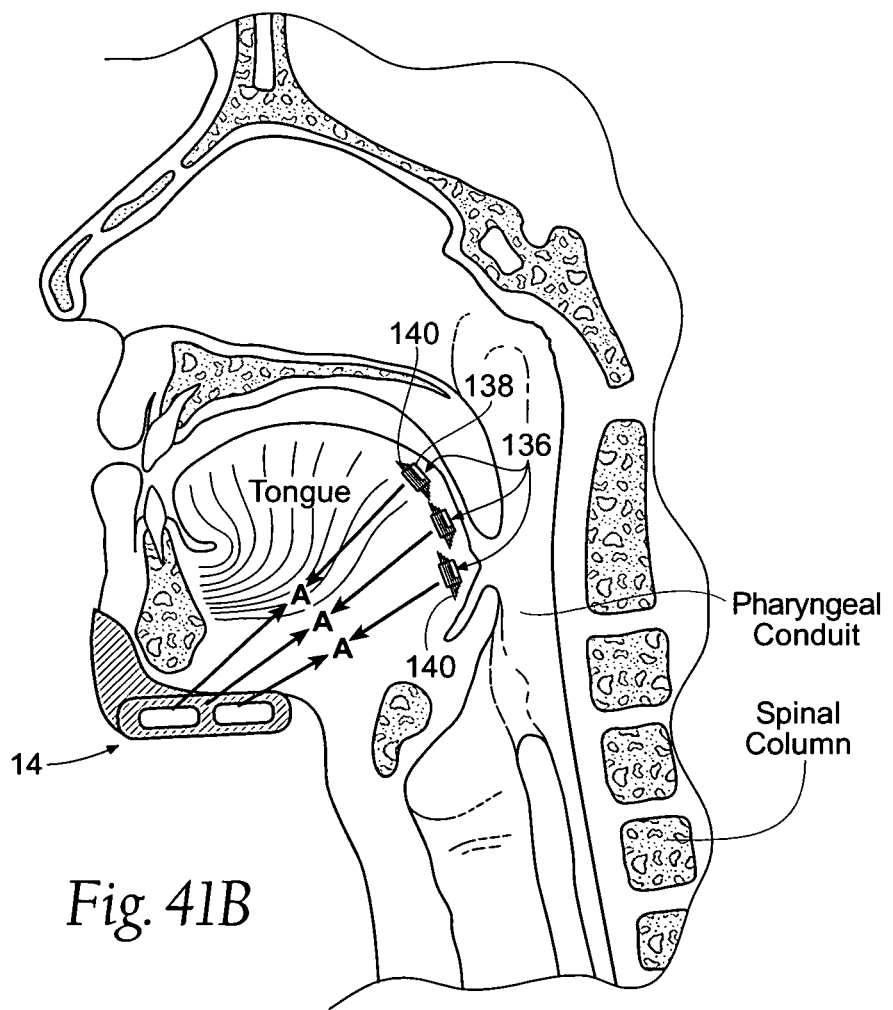

In an alternative embodiment, an implantable ferromagnetic structure 136 used in the tongue, soft palate, or pharyngeal wall can comprise ferromagnetic material 138 coupled to one or more elastic components 140, as shown in FIGS. 41A and 41B. The elastic component coupled to the ferromagnetic material 138 is sized and configured to deflect under load in a prescribed manner and to recover an initial shape when unloaded. As shown in FIGS. 41A and 41B the elastic component 140 comprises a spring.

The spring form of the elastic component 140 may vary. It may, e.g., comprise a helical tension or compression spring, in which wire is wrapped in a coil that resembles a screw thread, as shown in FIG. 41A. Alternatively, the elastic component 140 may comprise a leaf spring, comprising plate elements secured. Still alternatively, the elastic component 140 may comprise a spiral spring made from flat strip or wire coiled about the ferromagnetic material 138. Still alternatively, the elastic component 140 may comprise a torsion-bar spring.

The ferromagnetic material 138 desirably comprises one or more permanent magnets. The shape of the ferromagnetic material 138 need not be cylindrical, as shown in FIG. 41A. Other sizes, shapes, and configurations can be used, including cubes, pyramids, tetrahedrons, and various polyhedrons.

As shown in FIG. 41A, the elastic component 140 may be made out of metal or a polymer, desirably a rigid polymeric material. The elastic component 140 may consist of a single piece or comprise a construct of multiple elastic components. In spring form, the shape of the elastic component 140 need not be helical (as shown in FIG. 41A), but other constructions capable of deflecting under load can be used. The set up of a spring-form elastic component 140 could resemble a trampoline with multiple springs or elastic components attached peripherally about the ferromagnetic material 138. The spring-form elastic component 140 can also be tuned to any amount of force needed by modifying the pitch, the number of turns, the thickness and the overall angle in the spring's "cone."

As shown in FIG. 41B, the configuration of the spring-form elastic component 140 makes possible its use as an anchor, capable of attaching the ferromagnetic material 138 into soft tissue, by twisting. The presence of the spring-form elastic component 140 can thus eliminate the need to use sutures for attachment of the structure 136 to soft tissue. The spring-form elastic component 140 can also be secured (e.g., like a bone screw) to a bone structure, and, in this arrangement, also serve as a tethering device for the ferromagnetic structure 138. In whatever form, the elastic component 140 may be embedded or coated in a silicon matrix or soft material, as may be the ferromagnetic material 138. The presence of the elastic component on the ferromagnetic structure 136 can help stabilize torque in a system that incorporates ferromagnetic implants. Stabilizing the torque can bring about more predictability in the ferromagnetic implants.

E. Alternative Embodiments to the Tongue, Soft Palate and Combined Systems

In certain cases, the above-described Tongue, Soft Palate, and Combined Systems may not provide enough attractive magnetic force to maintain a patent airway. Under these circumstances, the respective System desirably includes at least one additional structure that interactions to provide a magnetic force that complements the attractive magnetic force to maintain a patent airway.

1. Complementary Tongue System

Figure 4E:
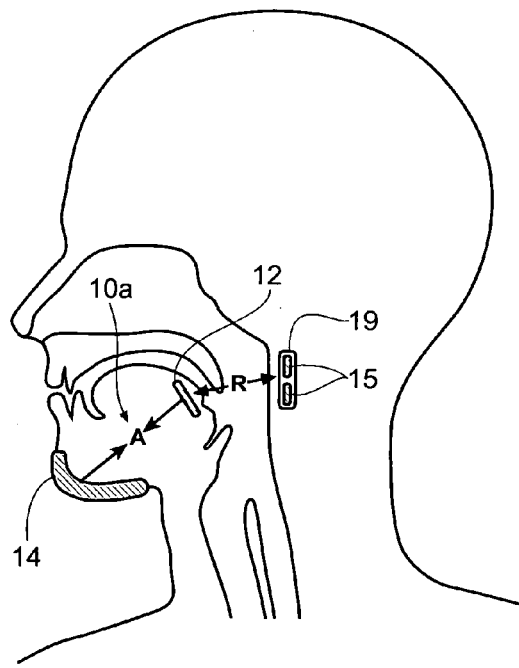
FIGS. 4E and 4F show alternative embodiments of the Tongue System that provide an additional repelling force to resist the collapse of the tongue.
Figure 4F:
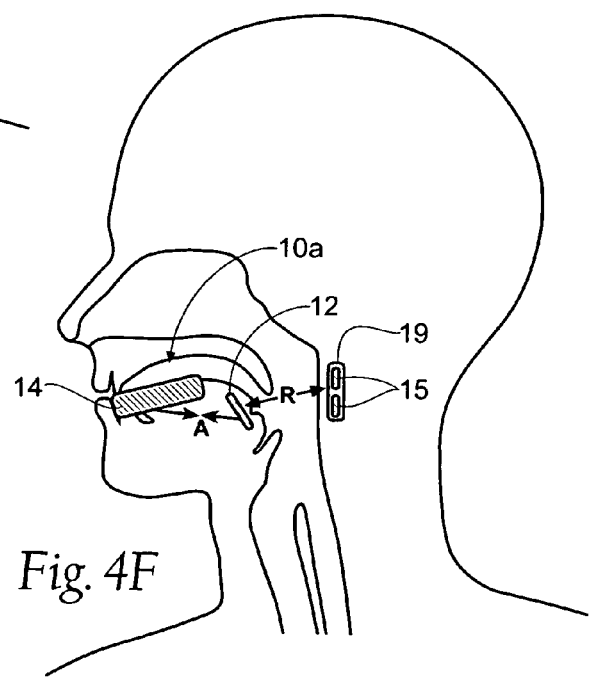

FIGS. 4E and 4F show alternative embodiments of the Tongue System that provide a complementary magnetic force to further resist the collapse of the tongue. In the representative embodiment shown in FIGS. 4E and 4F, the magnetic structure 12 is positioned in or on the tongue, as previously described. More specifically, magnetic structure 12 can be positioned either in the anterior or in the posterior region of the tongue. In FIG. 4E, the magnetic structure 14 (as previously described), which the magnetic structure 12 interacts with by attraction, is positioned outside the airway (e.g., on the chin), whereas in FIG. 4D, the magnetic structure 14 is positioned within the airway (e.g., in the oral cavity).

Furthermore, as shown in FIGS. 4E and 4F, to provide a complementary magnetic force for further resisting the collapse of the tongue, the Tongue System includes a magnetic structure 15 positioned in or on the posterior pharyngeal wall, generally opposite of magnetic structure 12 in or on the tongue. The magnetic structure 15 carries at least one magnetic material 19 that, by magnetic interactions with the structure 12, generates a magnetic force that includes at least one vector or component that magnetically repels the structure 12 in or on the mobile tissue of the tongue away from the structure 15 in or on the relatively less mobile tissue of the pharyngeal wall. In the illustrated embodiment, the magnetic material 19 of the structure 15 has a polarity the same as the polarity of the magnetic structure 12 that it faces across the airway. The magnetic structure 15 thereby interacts with the magnetic structure 12 across the airway by repulsion. The repelling magnetic interaction between the magnetic structure 15 and the magnetic structure 12 in the posterior airway serves to stabilize the tongue and resist collapse of the tongue against the pharyngeal wall during sleep. The repelling magnetic interaction between structures 12 and 15 in the posterior airway complements the attracting magnetic interaction between the structures 12 and 14 in the anterior airway, which likewise serves to resist posterior or other movement of the tongue toward the posterior pharyngeal wall. The complementary magnetic forces prevent, in whole or in part, the occurrence of the airway-occluding tissue condition shown in FIG. 3. The magnetic force between the first and second ferromagnetic structures 12 and 14, coupled with the magnetic force between ferromagnetic structures 12 and 15, work together to keep the airway open (i.e., patent) during sleep.

2. Complementary Soft Palate System

Figure 5C:
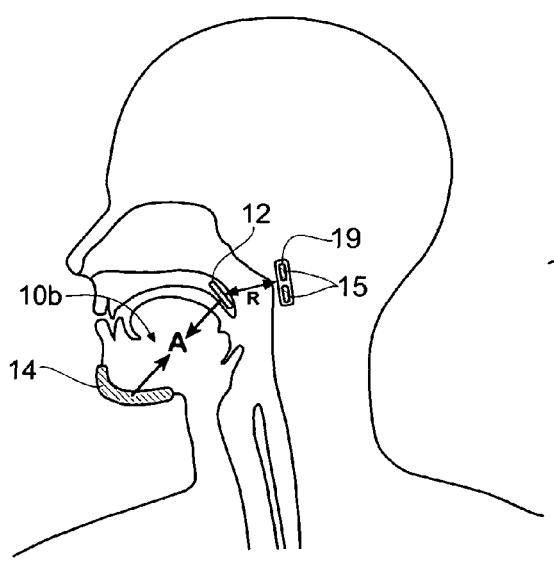
FIGS. 5C and 5D show alternative embodiments of the Soft Palate System that provide an additional repelling force to resist the collapse of the soft palate/uvula.
Figure 5D:
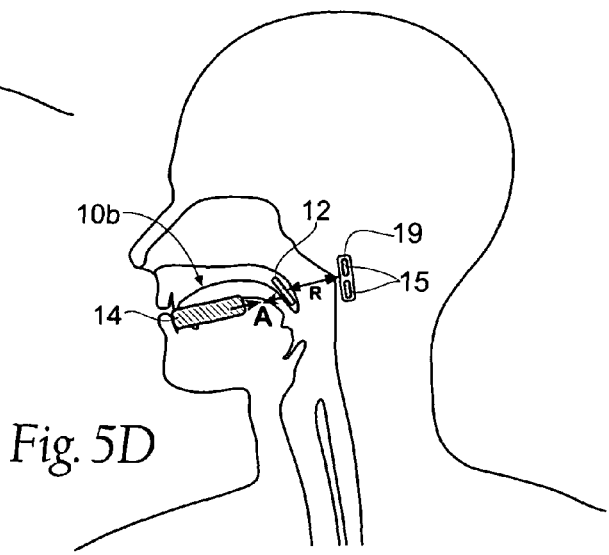

FIGS. 5C and 5D show alternative embodiments of the Soft Palate System that provide a complementary magnetic force to further resist the collapse of the soft palate/uvula. In the representative embodiment shown in FIGS. 5C and 5D, the magnetic structure 12 is positioned in or on the soft palate/uvula, as previously described. In FIG. 5C, the magnetic structure 14 (as also previously described), which the magnetic structure 12 interacts with by attraction, is positioned outside the airway (e.g., on the chin), whereas in FIG. 5D, the magnetic structure 14 is positioned within the airway (e.g., in the oral cavity).

Furthermore, as shown in FIGS. 5C and 5D, to provide a complementary magnetic force for further resisting the collapse of the soft palate/uvula, the Soft Palate System includes a magnetic structure 15 is positioned in or on the posterior pharyngeal wall, generally opposite of magnetic structure 12 in the soft palate/uvula. The magnetic structure 15 carries at least one magnetic material 19 that, by magnetic interactions with the structure 12, generates a magnetic force that includes at least one vector or component that magnetically repels the structure 12 in or on the mobile tissue of the soft palate/uvula away from the structure 15 in or on the relatively less mobile tissue of the pharyngeal wall. In the illustrated embodiment, the magnetic material 19 of the structure 15 has a polarity the same as the polarity of the magnetic structure 12 it faces across the airway. The magnetic structure 15 thereby interacts with the magnetic structure 12 across the airway by repulsion. The repelling magnetic interaction between the magnetic structure 15 in or on the pharyngeal wall and the magnetic structure 12 in or on the soft palate/uvula serves to stabilize the soft palate/uvula and resist collapse of the soft palate/uvula against the pharyngeal wall during sleep. The repelling magnetic interaction between structures 12 and 15 in the posterior airway complements the attracting magnetic interaction between the structures 12 and 14 in the anterior airway, which likewise serves to resist posterior or other movement of the soft palate/uvula toward the posterior pharyngeal wall. The complementary magnetic forces prevent, in whole or in part, the occurrence of the airway-occluding tissue condition shown in FIG. 3. The magnetic force between the first and second ferromagnetic structures 12 and 14, coupled with the magnetic force between ferromagnetic structures 12a/12b and 15a/15b, work together to keep the airway open (i.e., patent) during sleep.

3. Complementary Combined System

Figure 6C:
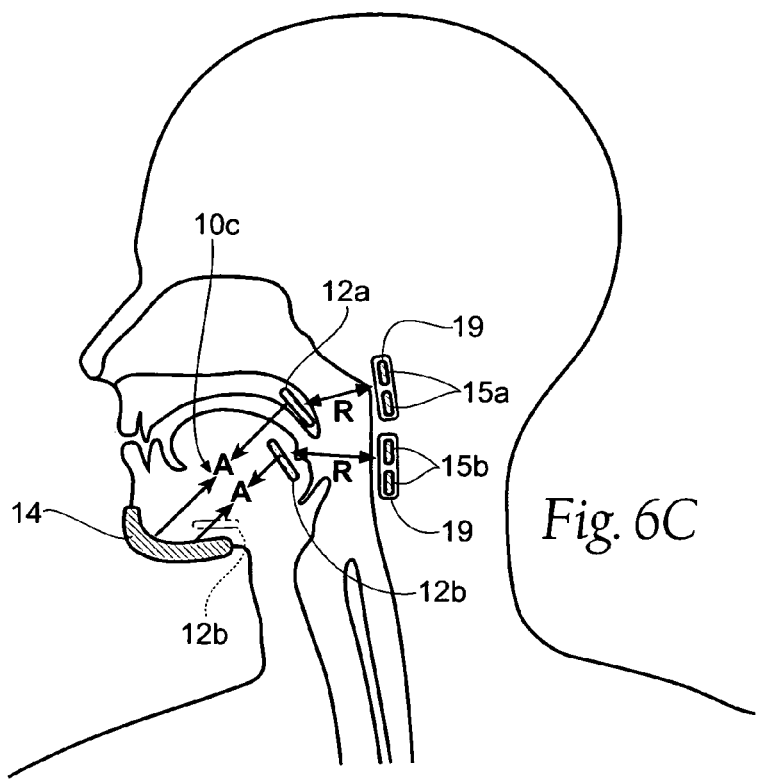
FIGS. 6C and 6D show alternative embodiments of the Combined System that provide an additional repelling force to resist the collapse of the tongue and soft palate/uvula.
Figure 6D:
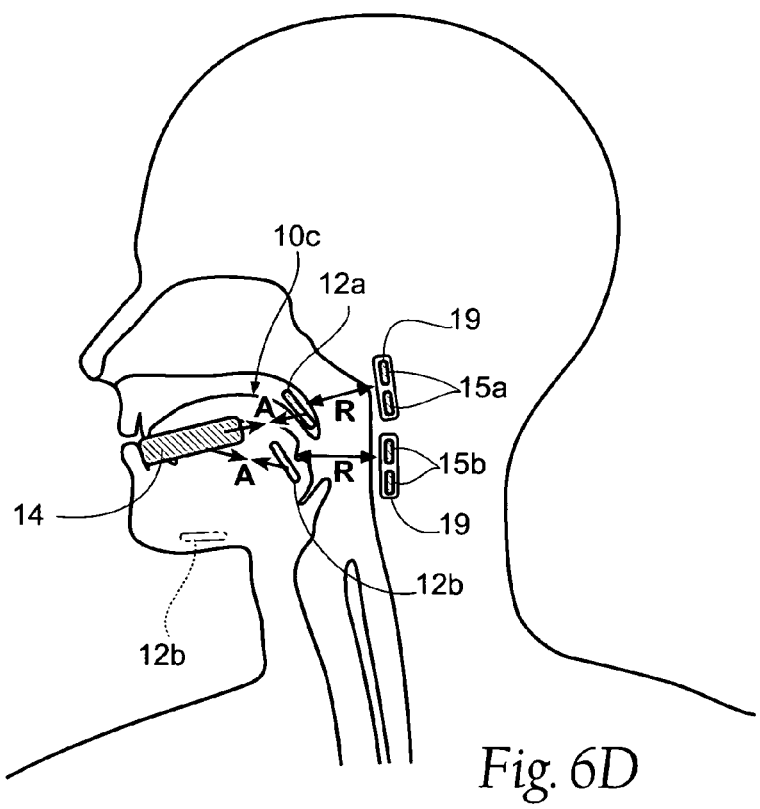

FIGS. 6C and 6D show alternative embodiments of the Combined System that provide a complementary magnetic force to further resist the collapse of the tongue and soft palate/uvula. In the representative embodiment shown in FIGS. 6C and 6D, the magnetic structure 12b is positioned in or on the tongue, while magnetic structure 12a is positioned in or on the soft palate/uvula, as previously described. More specifically, magnetic structure 12b can be positioned either in the anterior or in the posterior region of the tongue. In FIG. 6C, the magnetic structure 14 (also as previously described), which the magnetic structure 12a and 12b interacts with by attraction, is positioned outside the airway (e.g., on the chin), whereas in FIG. 6D, the magnetic structure 14 is positioned within the airway (e.g., in the oral cavity).

Furthermore, as shown in FIGS. 6C and 6D, to provide a complementary magnetic force for further resisting the collapse of the tongue and the soft palate/uvula, the Combined System includes a magnetic structure 15a and a magnetic structure 15b. The magnetic structure 15a is positioned in or on the posterior pharyngeal wall, generally opposite of magnetic structure 12a in or on the soft palate/uvula. The magnetic structure 15b is positioned in or on the posterior pharyngeal wall generally opposite to the magnetic structure 12b in or on the tongue. Each structure 15a and 15b carries at least one magnetic material 19 that, by magnetic interactions with the associated structure, respectively 12a and 12b, generates a magnetic force that includes at least one vector or component that magnetically repels the respective structure 12a and 12b in or on the mobile tissue of the soft palate/uvula or tongue away from the structure 15 in or on the relatively less mobile tissue of the pharyngeal wall. In the illustrated embodiment, the magnetic material 19 of the structure 15 has a polarity the same as the polarity of the magnetic structure, respectively 12a and 12b, it faces across the airway. The magnetic structures 15a and 15b thereby interact with the magnetic structures, respectively 12a and 12b across the airway by repulsion. The repelling magnetic interaction between the magnetic structure 15a in or on the pharyngeal wall and the magnetic structure 12a in or on the soft palate/uvula serves to stabilize the soft palate/uvula and resist collapse of the soft palate/uvula against the pharyngeal wall during sleep. Likewise, the repelling magnetic interaction between the magnetic structure 15b in or on the pharyngeal wall and the magnetic structure 12b in or on the tongue serves to stabilize the tongue and resist collapse of the tongue against the pharyngeal wall during sleep. The repelling magnetic interactions between structures 12a/12b and 15a/15b in the posterior airway complements the attracting magnetic interaction between the structures 12a/12b and 14 in the anterior airway, which likewise serves to resist posterior or other movements of either the soft palate/uvula and/or the tongue against the posterior pharyngeal wall. The complementary magnetic forces prevent, in whole or in part, the occurrence of the airway-occluding tissue condition shown in FIG. 3. The magnetic force between the first and second ferromagnetic structures 12 and 14, coupled with the magnetic force between ferromagnetic structures 12a/12b and 15a/15b, work together to keep the airway open (i.e., patent) during sleep.

V. Forces Required to Maintain a Patent Airway

Figure 36:
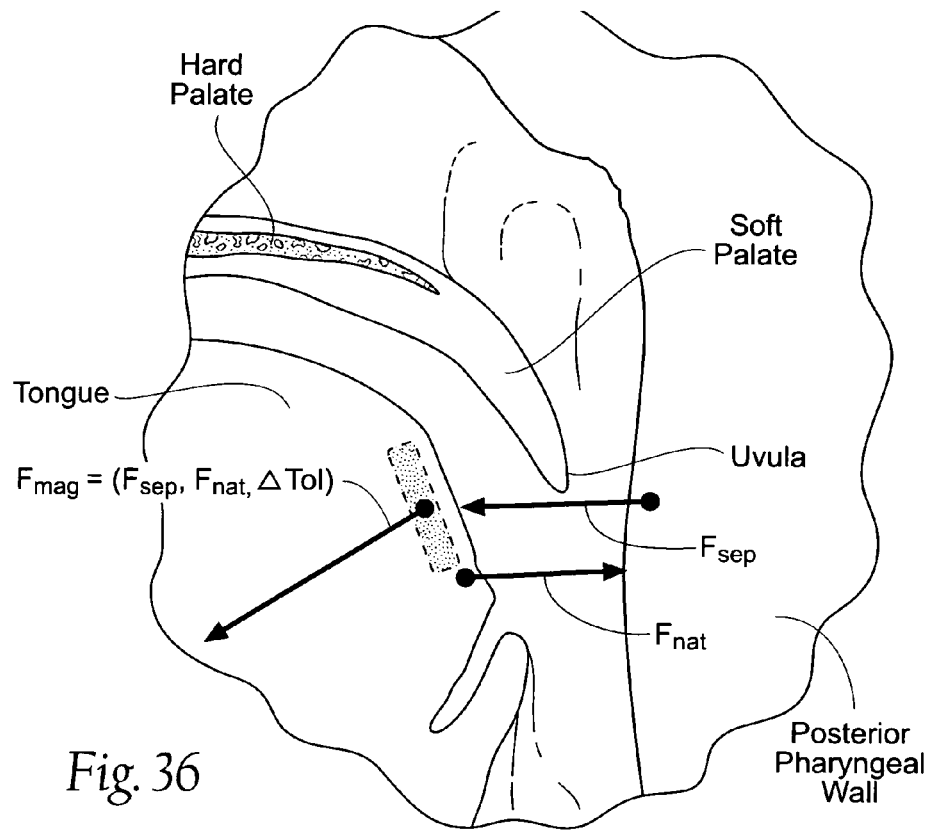
FIG. 36 is an anatomic sagittal view of the tongue, soft palate/uvula, and pharyngeal wall, showing the resolution of forces F-sep and F-nat to provide an optimal therapeutic force F-mag that, at night, resists collapse of the tongue against the pharyngeal wall during sleep, yet does not affect speech, swallowing or drinking during normal activities awake or asleep.
Figure 37:
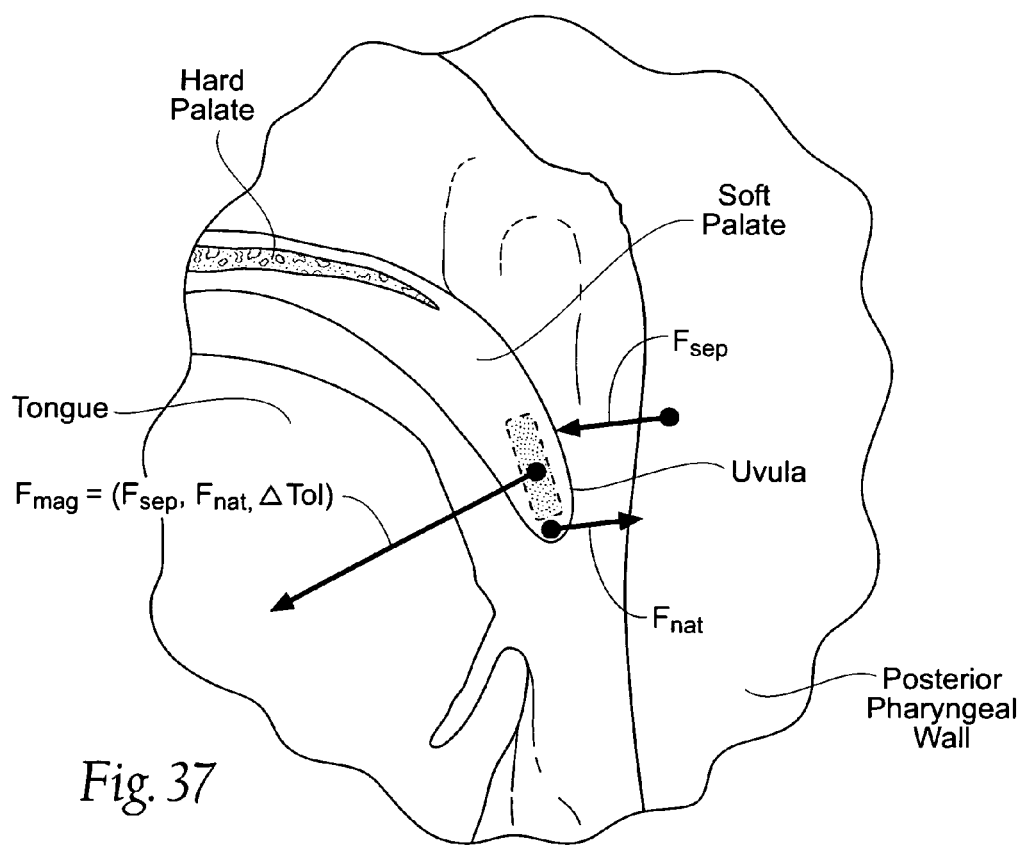
FIG. 37 is an anatomic sagittal view of the tongue, soft palate/uvula, and pharyngeal wall, showing the resolution of forces F-sep and F-nat to provide an optimal therapeutic force F-mag that, at night, resists collapse of the soft palate/uvula against the pharyngeal wall during sleep, yet does not affect speech, swallowing or drinking during normal activities awake or asleep.

As FIGS. 36 and 37 show in a diagrammatic way, for a given individual, that a magnitude can be assigned to a force required to maintain separation between tongue tissue (FIG. 36) or soft palate/uvula tissue (FIG. 37) from the posterior pharyngeal wall, to thereby resist the collapse of an airway during an apneic episode. This force, designated F-sep in FIGS. 36 and 37 can be obtained by physical measurement of a given individual, or it can based upon measurements taken during a cadaver study, or it can be selected empirically based upon general anatomic considerations for a population of individuals, or a combination of these and other considerations.

For a given individual, a magnitude can also be assigned to a counterbalancing force (designated F-nat in FIGS. 36 and 37), which represents the force exerted by natural muscular activity upon the tongue (FIG. 36) or the soft palate/uvula (FIG. 37), to enable swallowing, chewing, or speech during normal airway function. The force F-nat can be also obtained by physical measurement of a given individual, or it can be selected empirically based upon general anatomic considerations for a population of individuals, or a combination of these and other considerations.

As shown in FIGS. 36 and 37, the magnetic force (F-mag) that a given system 10 develops can be expressed as a function of F-sep and F-nat, or F-mag=f (F-sep, F-nat). The magnetic force can comprise an attracting force (i.e., a force in essentially an anterior-posterior direction between the tongue or soft palate/uvula and the attracting magnetic structure worn on the chin or neck or on teeth within the oral cavity), a repelling force (i.e., a force in essentially an anterior-posterior direction between repelling magnetic structures in the tongue and posterior pharyngeal wall), and/or a torquing force (i.e., a force or moment of a force that tends to rotate the tongue or soft palate/uvula about an axis), and/or decentering force (i.e., a force in essentially a lateral or side-to-side direction that tends to offset the tongue or soft palate/uvula left or right), or a combination of two or more of these forces. The magnetic force F-mag maintains a separation between the tongue and the posterior pharyngeal wall (FIG. 36), or between the uvula and the posterior pharyngeal wall (FIG. 37), or combinations thereof, depending upon the desired therapeutic effect.

The function desirably incorporates the premise that F-sep≦F-nat, such that F-nat can overcome F-sep to preserve normal airway function. In effect, F-nat is the upper limit for the amount of force used which, to achieve an effective OSA therapy, which F-sep should not exceed. The function also desirably incorporates the premise that F-mag≧F-sep, so that the desired separation between the tongue and the posterior pharyngeal wall is maintained. In the case of systems activated only during the night, F-nat will necessarily be larger in magnitude because the only activities that need to be able to continue during sleep are swallowing and coughing, which require more force than speaking.

The function resolves F-sep and F-nat to provide an optimal therapeutic force that, at night, resists collapse of the tongue or soft palate/uvula against the pharyngeal wall during sleep, yet does not affect speech, swallowing or drinking during normal activities when the system is activated.

The function also desirably includes a tolerance factor ΔTol, which takes into account that F-nat can increase with time after implantation, as an individual develops tolerance to F-mag. F-nat can thereby increase with time after implantation, as the individual trains himself or herself to exert more force during swallowing or speech in the presence of F-mag to maintain normal airway function. The nature of the tolerance factor ΔTol can be ascertained by physical measurement of a given individual, or it can be selected empirically based upon general anatomic considerations for a population of individuals, or a combination of these and other considerations.

Further, in arriving at the absolute magnitude of F-sep for the tongue (whether relative to the pharyngeal wall, or uvula, or both), it has been discovered that F-sep for the tongue can have two components. The first component is the desired therapeutic force F(z) that is developed in an anterior-to-posterior direction, which prevents the tongue from falling back upon the posterior pharyngeal wall or uvula. The second component is an undesired decentralizing side loading force F(y) that can be exerted due to magnetic force discontinuities at the edges of the tongue implant. It has been observed that, as the edges of a magnetic tongue implant start to misalign with the other magnetic structure (on the chin or neck or on the teeth or in the uvula), the magnets at the edges of the tongue implant may start to twist in an attempt to orient themselves to a more desired attracting arrangement. This can cause the tongue implant to twist or flip. The decentralizing side loading force F(y) is an outcome of these edge discontinuities, which moves the tongue laterally, i.e., to the side (the soft palate/uvula, being anatomically anchored on three of four sides, is significantly more resistant to a side loading force than the tongue, which is anchored essentially only on the posterior side).

A desired therapeutic force magnitude F(z) can, if the edge discontinuities are not moderated, undesirably move the tongue laterally. The magnitude of the edge discontinuities, i.e., the magnitude of F(y), can be titrated and controlled by the design of the other magnetic structure, e.g., by directing the magnetic fields of the posterior and middle regions of the structure at an angle relative to the direction of the magnetic fields of the anterior region, as shown in FIGS. 16A/B. Further, by stabilizing the tongue implant in the manners previously described, e.g., by the presence of a rudder as shown in FIGS. 28 to 35 or by the use of mobile magnets as shown in FIGS. 21 to 23, the destabilizing effects of F(y) can be also counteracted.

Figure 38:
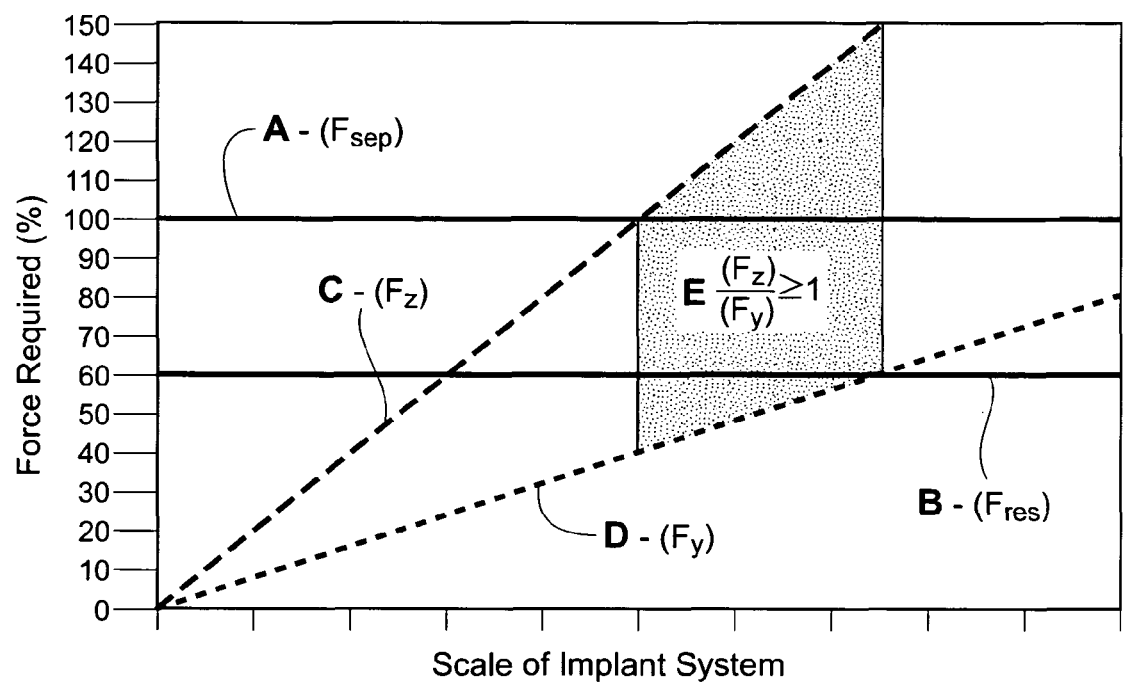
FIG. 38 is a chart executing an implant force scaling strategy.

An implant force scaling strategy like that shown in FIG. 38 can be based upon an appreciation of these considerations. In FIG. 38, the magnitude of a force applied in an anterior-posterior direction upon the tongue necessary to achieve the desired therapeutic effect (i.e., F-sep) is indicated at A. As indicated before, this is the force required to separate tongue tissue from the posterior pharyngeal wall or uvula, or both, to thereby resist the collapse of an airway during an apneic episode. The force F-sep (also shown in FIG. 36), can be obtained by physical measurement or selected empirically based upon general anatomic considerations for a population of individuals, or a combination of these and other considerations.

In FIG. 38, the magnitude of the resistance (F-res) of a given tongue decentered medially in response to an external side load is indicated at B. The specific magnitude of F-res can be obtained by physical measurement of a given individual, or it can be based upon cadaver studies, or it can be selected empirically based upon general anatomic considerations for a population of individuals, or a combination of these and other considerations. In FIG. 38, the magnitude of F-res (B) is expressed as a percentage of F-sep (A). That is, on the y-axis, F-sep (A) is expressed as 100% and F-res (B) is expressed as 60%. The particular relationship between F-sep and F-res can vary based upon anatomic considerations.

In FIG. 38, the magnitude of the anterior-to-posterior force F(z) generated by a given attracting magnetic structure (on the chin or neck or on the teeth or in the uvula, or combinations thereof) is indicated by C. As FIG. 38 shows by the slope of C, this magnitude of F(z) will vary as a function of distance between the attracting magnetic structure and the tongue implant, as well as a function of the particular structural characteristics and stabilization of the tongue implant itself.

In FIG. 38, the magnitude of the side load force F(y) generated by the given pharyngeal wall implant is indicated by D. The slope and magnitude of D will vary based upon the design of the pharyngeal wall implant or the uvula implant, particularly with respect to the moderation of edge discontinuities, as previously described. The slope and magnitude of D will also depend upon the particular structural characteristics and stabilization of the tongue implant itself.

For a given magnetic force system affecting the tongue, the magnitude of F(z) with respect to the magnitude of F(y) represents an Implant Scaling Factor (F-scale). F-scale can be expressed as a ratio of F(z) to F(y); that is F-scale=F(z)/F(y). The magnitude of F-scale for a given magnetic force system affecting the tongue indicates that the system is likely to achieve the desired therapeutic effect without decentering the tongue.

It has been discovered that, for a given magnetic force system affecting the tongue, an F-scale≧1 is desirable. For a given magnetic force system affecting the tongue, an F-scale<1 indicates that decentering of the tongue will occur, which offsets the desired therapeutic effect. An F-scale<1 indicates that the edge discontinuities of the attracting magnetic structure (on the chin or neck or on the teeth) should be reduced or moderated and/or means for stabilizing the tongue implant are warranted.

FIG. 38 also lends itself to an implant force scaling strategy. The intersections of C and D with A and B define an optimal operating region E for a magnetic force system affecting the tongue. In region E, F(z) is at or above the magnitude that achieves the desired therapeutic effect but where F(y) is not at the magnitude at which side loading (i.e., decentering of the tongue) will occur.

Experimentally, it has been determined that the force F-mag likely required to keep an airway open on a cadaver using a magnetic force system that affects the tongue is no more than 1000 g. It is believed that magnetic tongue implant systems require a force of about 2 to about 750 g to maintain a patent airway. More specifically, a force in the range of about 5 to about 600 g is believed to provide the desired therapeutic benefits in combination with control of edge discontinuities in the other magnetic structure on chin or neck or on the teeth and stabilization of the tongue implant itself.

It is also believed that F-mag for a magnetic force system that affects the palate should also be no more than 1000 g. More specifically, for a magnetic force system that affects the palate, it is believed that a force F-mag of about 3 to about 800 g will provide therapeutic benefits without adversely affecting normal functioning of the airway.

VI. Conclusion

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

The above-described embodiments of this invention are merely descriptive of its principles and are not to be limited. The scope of this invention instead shall be determined from the scope of the following claims, including their equivalents.

We claim:

1. A system comprising:
at least one ferromagnetic structure adapted to be implanted within a first region of a tissue,
at least one anchoring structure adapted to be implanted within a second region of the same tissue spaced from the at least one ferromagnetic structure, the at least one anchoring structure including an expandable structure having a collapsed position prior to implantation and an expanded position after being implanted within the tissue, and
at least one attachment element coupling the at least one anchoring structure to the at least one ferromagnetic structure to stabilize the at least one ferromagnetic structure in the first region of the tissue.

2. A system according to claim 1:
further including at least one additional ferromagnetic structure sized and configured for placement in a desired relationship with the at least one ferromagnetic structure to magnetically interact with the at least one ferromagnetic structure.

3. A method comprising:
providing a system as defined in claim 2, implanting the at least one ferromagnetic structure, the at least one anchoring structure, and the at least one attachment element in the tissue,
placing the at least one additional ferromagnetic structure in the desired relationship with the at least one ferromagnetic structure, and
stabilizing a desired tissue orientation by magnetic interactions between the at least one ferromagnetic structure and the at least one additional ferromagnetic structure.

4. A method for reducing or preventing sleep disordered breathing events comprising providing a system as defined in claim 2.

5. The system of claim 1 wherein the expandable structure of the at least one anchoring structure is an expandable umbrella-like structure; and wherein the expandable umbrella-like structure is adapted to collapse in order to facilitate implantation and to expand in situ at the implantation site after implantation.

6. The system of claim 1 wherein the at least one attachment element is at least one tether attached at one end to the at least one ferromagnetic structure and at the other end to a corresponding one of the at least one anchoring structure.

7. The system of claim 6 wherein the at least one tether is a plurality of tethers; wherein the at least one anchoring structure is a plurality of anchoring structures; wherein each of the tethers is attached at one end to the at least one ferromagnetic structure and at the other end to a corresponding one of the plurality of anchoring structures.

8. The system of claim 1 wherein the tissue is a tongue; wherein the first region in which the at least one ferromagnetic structure is implanted is an anterior region of the tongue; and wherein the second region in which the at least one anchoring structure is implanted is a posterior region of the tongue.

* * * * *